(12) United States Patent
Perner et al.

(10) Patent No.: US 7,998,993 B2
(45) Date of Patent: Aug. 16, 2011

(54) TRPV1 ANTAGONISTS

(75) Inventors: Richard J. Perner, Gurnee, IL (US);
John R. Koenig, Chicago, IL (US);
Stanley DiDomenico, Jr., Richmond, IL (US); Erol K. Bayburt, Gurnee, IL (US); Jerome F. Daanen, Racine, WI (US); Arthur Gomtsyan, Vernon Hills, IL (US); Michael E. Kort, Lake Bluff, IL (US); Philip R. Kym, Libertyville, IL (US); Robert G. Schmidt, Waukegan, IL (US); Anil Vasudevan, Union Grove, WI (US); Eric Voight, Pleasant Prairie, WI (US)

(73) Assignee: Abbott Laboratories, Abbott Park, IL (US)

( * ) Notice: Subject to any disclaimer, the term of this patent is extended or adjusted under 35 U.S.C. 154(b) by 15 days.

(21) Appl. No.: 12/256,931

(22) Filed: Oct. 23, 2008

(65) Prior Publication Data
US 2009/0124666 A1    May 14, 2009

Related U.S. Application Data

(60) Provisional application No. 60/982,490, filed on Oct. 25, 2007.

(51) Int. Cl.
*A61K 31/421* (2006.01)
*C07D 263/48* (2006.01)
(52) U.S. Cl. ........................ 514/377; 548/234
(58) Field of Classification Search ................. None
See application file for complete search history.

(56) References Cited

U.S. PATENT DOCUMENTS
5,151,440 A    9/1992  Gluchowski
2006/0281799 A1  12/2006  Gomtsyan et al.

FOREIGN PATENT DOCUMENTS
WO    WO 2006/122250    * 11/2006
WO    WO-2006122250 A3    11/2006

OTHER PUBLICATIONS

Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Wolff et al. Burger's Medicinal Chemistry and Drug Discovery. 5th ed. vol. 1: Principles and Practice (1995). pp. 975-977.*
Berge, S.M. et al., "Journal of Pharmaceutical Sciences, Pharmaceutical Salts," J Pharmaceutical Sciences, 1977, 1-19, vol. 66.
Caterina et al., "Impaired Nociception and Pain Sensation in Mice Lacking the Capsaicin Receptor," Science, 2000, 306-313, vol. 288.
Caterina et al., "The Vanilloid Receptor: A Molecular Gateway to the Pain Pathway," Annu Rev Neurosci, 2001, 487-517, vol. 24.
Caterina M.J. et al., "The Capsaicin Receptor: A Heat-Activated Ion Channel in the Pain Pathway," (Binary/Image), 1997, 816-824, vol. 389.
Cui M et al., "TRPV1 Receptors in the CNS Play a Key Role in Broad-Spectrum Analgesia of TRPV1 Antagonists," The Journal of Neuroscience, 2006, vol. 26 (37), pp. 9385-9393.
Davis et al., "Vanilloid receptor-1 is essential for inflammatory thermal hyperalgesia," (Binary/Image), 2000, 183-187, vol. 405.
Fowler, C. "Intravesical Treatment of Overactive Bladder," Urology, 2000, 60-64, vol. 55.
Greene, T.W. et al., "Protective Groups in Organic Synthesis", 1999, 3 rd Ed, 494-653.
Hayes et al., "Cloning and Functional Expression of a Human Orthologue of Rat Vanilloid Receptor-1," (Binary/Image), 2000, 205-215, vol. 88.
Marsch R, Foeller E, Rammes G, et al., "Reduced anxiety, conditioned fear, and hippocampal long-term potentiation in transient receptor potential vanilloid type 1 receptor-deficient mice," J Neurosci, 2007, 0832-09-01, 27/4.
Mezey, Eva et al., "Distribution of mRNA for vanilloid receptor subtype 1 (VR1), and VR1-like immunoreactivity, in the central nervous system of the rat and human," Neurobiology, 2000, vol. 97 (7), pp. 3655-3660.
Nolano et al., "Topical Capsaicin in Humans: Parallel Loss of Epidermal Nerve Fibers and Pain Sensation," (Binary/Image), 1999, 135-145, vol. 81.
Prescott et al., Methods in Cell Biology, 1976, vol. XIV, 33, Academic Press.
Roberts c. Jennifer et.al, "[3H]Resiniferatoxin autoradiography in the CNS of wild-type and TRPV1 null mice defines TRPV1 (VR-1) protein distribution," Brain Research, 2004, vol. 995, pp. 176-183.
Szabo T. et al., "Pharmacological characterization of vanilloid receptor located in the brain," Molecular Brain Research, 2002, vol. 98, pp. 51-57, Elsevier Science.
Tzavara ET, Li DL, Moutsimilli L, et al., "Endocannabinoids activate transient receptor potential vanilloid 1 receptors to reduce hyperdoaminergia-related hyperactivity: therapeutic implications," Biol Psychiatry, 2006, 508-15, 59/6.
Westaway S.M., "The potential of transient receptor potential vanilloid type 1 channel modulators for the treatment of pain, XP002452089," Journal of Medicinal Chemistry, vol. 50, pp. 2589-2596, 2007.

* cited by examiner

*Primary Examiner* — Rebecca Anderson
*Assistant Examiner* — Alicia L Otton
(74) *Attorney, Agent, or Firm* — Lisa V. Mueller; Polsinelli Shughart PC

(57) ABSTRACT

Compounds of formula (I)

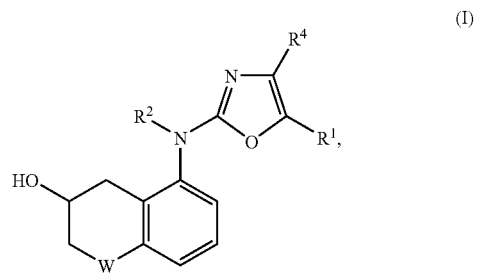

wherein $R^1$, $R^2$, $R^4$, and W are defined in the description are TRPV 1 antagonists with CNS penetration. Compositions comprising such compounds and methods for treating conditions and disorders using such compounds and compositions are also disclosed.

15 Claims, No Drawings

TRPV1 ANTAGONISTS

This application claims priority to U.S. Ser. No. 60/982,490, filed Oct. 25, 2007, and is incorporated herein by reference.

TECHNICAL FIELD

The present invention generally relates to oxazole containing compounds, compositions comprising such compounds, and methods of treating conditions and disorders using such compounds and compositions.

BACKGROUND

Nociceptors are primary sensory afferent (C and Aδ fibers) neurons that are activated by a wide variety of noxious stimuli including chemical, mechanical, thermal, and proton (pH<6) modalities. The lipophilic vanilloid, capsaicin, activates primary sensory fibers via a specific cell surface capsaicin receptor, cloned as the transient receptor potential vanilloid-1 (TRPV1). TRPV1 is also known as vanilloid receptor-1 (VR1). The intradermal administration of capsaicin is characterized by an initial burning or hot sensation followed by a prolonged period of analgesia. It is believed that the analgesic component of the TRPV1 receptor activation is mediated by a capsaicin-induced desensitization of the primary sensory afferent terminal. Thus, the long lasting anti-nociceptive effect of capsaicin has prompted the clinical use of capsaicin analogs as analgesic agents. Further, capsazepine, a capsaicin receptor antagonist can reduce inflammation-induced hyperalgesia in animal models. TRPV1 receptors are also localized on sensory afferents, which innervate the bladder. Capsaicin or resiniferatoxin has been shown to ameliorate incontinence symptoms upon injection into the bladder.

The TRPV1 receptor has been called a "polymodal detector" of noxious stimuli since it can be activated in several ways. The receptor channel is activated by capsaicin and other vanilloids, and thus is classified as a ligand-gated ion channel. TRPV1 receptor activation by capsaicin can be blocked by the competitive TRPV1 receptor antagonist, capsazepine. Protons (acidic pH) can also activate the TRPV1 channel. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knockout" mouse lacking the TRPV1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The TRPV1 (−/−) mice also did not show reduced sensitivity to nerve injury-induced mechanical or thermal nociception. However, the TRPV1 knockout mice were insensitive to the noxious effects of intradermal capsaicin, exposure to intense heat (50-55° C.), and failed to develop thermal hyperalgesia following the intradermal administration of carrageenan.

TRPV1 receptors have been found in both the peripheral nervous system and the central nervous system (CNS). In the brain, TRPV1 receptors have been identified in various regions known for their role in pain transmission or modulation (Merzey et al., Proc. Natl. Acad. Sci. USA 97:3655-3660 (2000); Szabo et al., Mol. Brain. Res. 98:51-57 (2002); Roberts et al., Brain Res. 995:176-183 (2004)). Using TRPV1 antagonists with similar in vitro potency but different CNS penetration, studies by Cui, M.; Honore, P. et al. J. Neuroscience 26:9385-9393 (2006) demonstrated that the CNS plays a differential role in the effect of TRPV1 antagonists in various types of pain. Employing a number of rodent models, these experiments showed that TRPV1 receptors in the CNS play an important role in pain mediated by central sensitization. Moreover, these findings demonstrated that significant CNS penetration is necessary for a TRPV1 antagonist to produce broad-spectrum analgesia.

Certain TRPV1 antagonists are discussed in U.S. Publication No. 2006/0281799 with unknown CNS penetration. Accordingly, the need exists to develop TRPV1 antagonists that exhibit good CNS penetration. Such antagonists may provide full efficacy across a wide array of pain states.

We herein describe series of TRPV1 antagonists with CNS penetration.

SUMMARY

The present invention generally provides oxazole containing compounds and pharmaceutical compositions and methods for the treatment of disorders using these compounds and pharmaceutical compositions.

One aspect of the invention is directed towards compounds of formula (I), or pharmaceutically acceptable salts, prodrugs, salts of prodrugs, or combinations thereof,

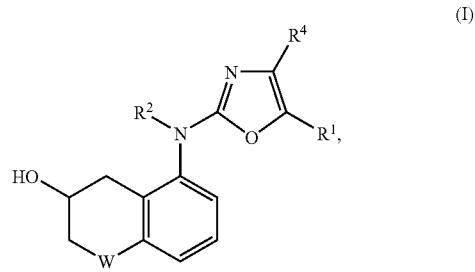

wherein
W is $CH_2$ or O;
$R^1$ is phenyl, a monocyclic heteroaryl, or a monocyclic cycloalkenyl, a monocyclic cycloalkyl, each of which is independently unsubstituted or substituted with 1, 2, 3, 4, or 5 substituents as represented by $R^3$, wherein each $R^3$ is independently alkyl, alkenyl, alkynyl, —$NO_2$, —CN, halogen, —$OR^a$, —$OC(O)R^a$, —$SR^a$, —$SF_5$, —$S(O)R^b$, —$S(O)_2R^b$, —$S(O)_2N(R^a)(R^c)$, —$N(R^a)(R^c)$, —$N(R^c)C(O)R^a$, —$N(R^c)S(O)_2R^b$, —$N(R^c)C(O)N(R^a)(R^c)$, —$N(R^c)S(O)_2N(R^a)(R^c)$, —$C(O)R^a$, —$C(O)O(R^a)$, —$C(O)N(R^a)(R^c)$, —$(CR^eR^f)_m$—CN, haloalkyl, or a monocyclic cycloalkyl that is optionally substituted with 1, 2, 3, or 4 substituents independently selected from the group consisting of alkyl, haloalkyl and halogen;

$R^a$, at each occurrence, is independently hydrogen, alkyl, or haloalkyl;

$R^b$, at each occurrence, is independently alkyl or haloalkyl;

$R^c$, at each occurrence, is independently hydrogen, alkyl or haloalkyl;

$R^e$ and $R^f$ are each independently hydrogen, alkyl, or haloalkyl;

m is 1, 2, or 3;

$R^2$ is hydrogen or alkyl; and $R^4$ is methyl, ethyl, $C_1$-$C_2$ haloalkyl, or —CN.

Another aspect of the inventions relates to a pharmaceutical composition comprising a compound of formula (I) or a pharmaceutically acceptable salt or solvate thereof, and one or more pharmaceutically acceptable carriers. Another aspect of the inventions relates to a pharmaceutical composition comprising a compound of formula (I) or a pharmaceutically acceptable salt or solvate thereof, one or more pharmaceutically acceptable carriers, and one or more analgesic agents, wherein the analgesic agent is a nonsteroidal anti-inflammatory drug (NSAID), or acetaminophen, or a combination thereof.

Yet other aspect provides methods for treating diseases or disorders as defined herein. Said methods comprise the step of administering therapeutically effective amount of a compound of formula (I), or a pharmaceutically acceptable salt thereof, or a pharmaceutical composition as described herein, to a subject in need thereof.

Further aspect of the invention provides the use of a compound of formula (I), or a pharmaceutically acceptable salt thereof, in the manufacture of a medicament for the treatment of disease or disorders as defined herein, with or without one or more pharmaceutically acceptable carrier, and alone, or in combination with acetaminophen, or in combination with one or more nonsteroidal anti-inflammatory drug (NSAID), or a combination thereof.

It is to be understood that both the foregoing general description and the following detailed description are exemplary, but are not restrictive, of the invention.

DETAILED DESCRIPTION

Compounds of formula (I) are disclosed in this invention,

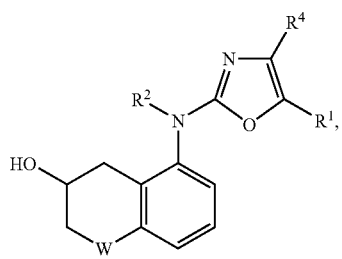

(I)

wherein $R^1$, $R^2$, $R^4$, and W are defined above in the Summary of the Invention and below in the Detailed Description. Preferably, compounds of the invention are TRPV1 antagonists that exhibit CNS penetration. Further, compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definition

As used in the specification and the appended claims, unless specified to the contrary, the following terms have the meaning indicated:

The term "alkenyl" as used herein, means a straight or branched chain hydrocarbon containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The term "$C_2$-$C_3$ alkenyl" means a straight or branched chain hydrocarbon containing from 2 or 3 carbons and containing at least one carbon-carbon double bond.

The term "alkyl" as used herein, means a straight or branched chain saturated hydrocarbon containing from 1 to 10 carbon atoms, for example, from 1 to 6 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, 3,3-dimethylbutyl, n-heptyl, n-octyl, n-nonyl, and n-decyl. The term "$C_1$-$C_3$ alkyl" as used herein, means a straight or branched chain saturated hydrocarbon containing 1, 2, or 3 carbon atoms. The term "$C_1$-$C_4$ alkyl" as used herein, means a straight or branched chain saturated hydrocarbon containing 1, 2, or 4 carbon atoms. The term "$C_1$-$C_2$ alkyl" as used herein, means methyl and ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "halo" or "halogen" as used herein, means —Cl, —Br, —I or —F.

The term "haloalkyl" as used herein, means at least one halogen (for example, one to six halogens), as defined herein, appended to the parent molecular moiety through an alkyl group, as defined herein. Representative examples of haloalkyl include, but are not limited to, chloromethyl, difluoromethyl, 2-fluoroethyl, trifluoromethyl, pentafluoroethyl, and 2-chloro-3-fluoropentyl. The term "$C_1$-$C_2$ haloalkyl" as used herein, means at least one halogen (for example, one to six halogens), as defined herein, appended to the parent molecular moiety through a $C_1$-$C_2$ alkyl group, as defined herein.

The term "monocyclic cycloalkenyl" as used herein, means an optionally substituted monocyclic ring system containing three-, four-, five-, six-, seven- or eight carbon atoms and zero heteroatoms. The three or four-membered ring systems have one double bond, the five- or six-membered ring systems have one or two double bonds, and the seven- or eight-membered ring systems have one, two or three double bonds. Representative examples of monocyclic cycloalkenyls include, but are not limited to, cyclohex-1-en-1-yl, 2-cyclohexen-1-yl, 3-cyclohexen-1-yl, 2,4-cyclohexadien-1-yl and 3-cyclopenten-1-yl.

The term "monocyclic cycloalkyl" as used herein, means an optionally substituted monocyclic carbocyclic ring system containing 3, 4, 5, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl.

The term "monocyclic heteroaryl" as used herein, means an optionally substituted 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three or four heteroatoms. Representative examples of monocyclic heteroaryls include, but are not limited to, furanyl (including furan-2-yl), imidazolyl, isoxazolyl, isothiazolyl, oxadiazolyl, oxazolyl, pyridinyl (including pyridine-3-yl, pyridine-2-yl), pyridazinyl, pyrimidinyl, pyrazinyl, pyrazolyl, pyrrolyl, tetrazolyl, thiadiazolyl, thiazolyl, thienyl (including thien-2-yl and thien-3-yl), triazolyl, and triazinyl. The monocyclic heteroaryl groups are connected to the parent molecular moiety through any substitutable carbon atom or any substitutable nitrogen atom contained within the groups. The nitrogen and sulfur heteroatoms of the rings may optionally be oxidized, and are contemplated within the scope of the invention.

b. Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In compounds of formula (I), $R^1$ is phenyl, a monocyclic heteroaryl, or a monocyclic cycloalkenyl, a monocyclic cycloalkyl, each of which is optionally substituted as described in the Summary.

For example, $R^1$ is optionally substituted phenyl. Particularly, $R^1$ is substituted phenyl. More particularly, $R^1$ is phenyl, substituted with 1, 2, or 3 substituents as represented by $R^3$. When $R^1$ is a substituted phenyl, it is preferred that at least one substituent is located at the fourth carbon atom of the phenyl ring relative to the point of attachment of the phenyl ring to the parent moiety. Thus, examples of compounds of the invention include, but are not limited to, those represented by formula (Ia)

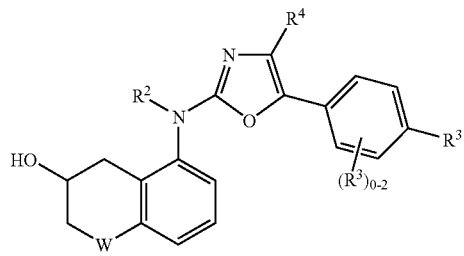

(Ia)

wherein W, $R^2$, $R^3$, and $R^4$ are as described in the Summary and the Detailed Description sections.

In certain embodiments, $R^1$ is optionally substituted monocyclic heteroaryl. Particularly, $R^1$ is monocyclic heteroaryl, optionally substituted with 1, 2, or 3 substituents as represented by $R^3$. Examples of the monocyclic heteroaryl include, but are not limited to, furanyl (including furan-2-yl), thienyl (including thien-2-yl and thien-3-yl) and pyridinyl (including pyridin-2-yl, pyridin-3-yl), each of which is optionally substituted.

In certain embodiments, $R^1$ is optionally substituted monocyclic cycloalkenyl. An example of the cycloalkenyl includes, but is not limited to, optionally substituted cyclohexenyl (e.g. cyclohex-1-en-yl).

Examples of $R^3$ include, but are not limited to, alkyl, alkenyl, —CN, halogen, —OR$^a$, —SF$_5$, —S(O)$_2$R$^b$, haloalkyl, —(CR$^e$R$^f$)$_m$—CN, and an optionally substituted cycloalkyl; wherein m, R$^a$, R$^b$, R$^e$, and R$^f$ are as described in the Summary. For example, R$^a$ and R$^b$, are each independently alkyl (e.g. methyl) or haloalkyl (e.g. trifluoromethyl). Each occurrence of R$^e$ and R$^f$ for example, are each independently hydrogen or alkyl (e.g. methyl). Particular examples of the substituents of $R^1$ include, but are not limited to, $C_1$-$C_4$ alkyl (e.g. methyl, ethyl, tert-butyl), $C_2$-$C_3$ alkenyl (e.g. 2-methyl-2-propenyl), —CN, halogen (e.g. F, Cl, Br), —OCH$_3$, —OCF$_3$, —SF$_5$, —S(O)$_2$(CF$_3$), trifluoromethyl, difluoromethyl, —C(CH$_3$)$_2$—CN, and an optionally substituted cyclopropyl Examples of compounds of formula (I) or (Ia) include those wherein $R^2$ is hydrogen or alkyl. In certain embodiments, $R^2$ is hydrogen or $C_1$-$C_3$ alkyl such as, but not limited to, methyl. In certain embodiments, $R^2$ is hydrogen.

$R^4$ has values as described generally in the Summary. In certain embodiments, $R^4$ is methyl or ethyl. In other embodiments, $R^4$ is $C_1$-$C_2$ haloalkyl such as, but not limited to, difluoromethyl. In yet other embodiments, $R^4$ is —CN. Examples of compounds of formula (I) and (Ia) include, but not limited to, those wherein $R^4$ is methyl, ethyl, —CN, or difluoromethyl.

It is appreciated that the present invention contemplates compounds of formula (I) with combinations of the above embodiments, including particular, more particular and preferred embodiments.

Compounds of the present invention contain one or more asymmetrically substituted carbon atoms in the cycloalkene ring of formula (I) and (Ia). For example, Compounds of formula (I) and (Ia) can have stereoisomers including, but not limited to, those shown below:

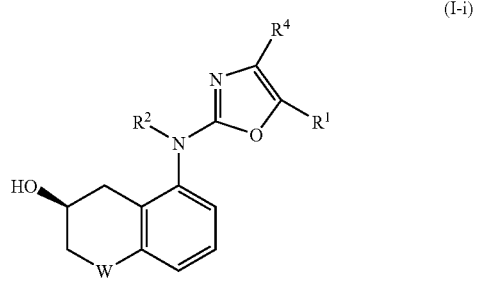

(I-i)

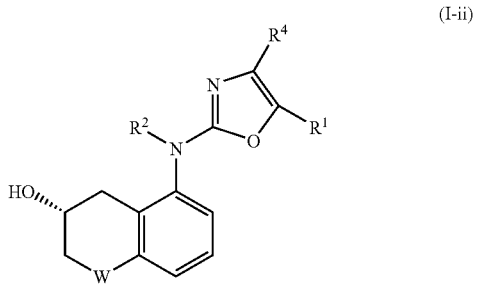

(I-ii)

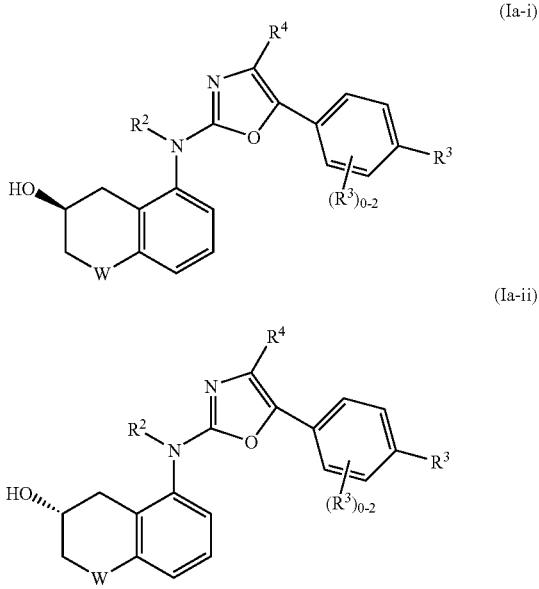

wherein $R^1$, $R^2$, $R^3$, $R^4$, and W are as disclosed in the Summary and the Detailed Description sections. It is understood that embodiments for $R^1$, $R^2$, $R^3$, $R^4$, and W, and combinations of embodiments, including particular, and more particular embodiments as described for formula (I), are also contemplated for compounds of formula (I-i), (I-ii), (Ia-i), and (Ia-ii). The present invention contemplates various individual stereoisomers (including enantiomers and diastereomers) and mixtures thereof. Individual stereoisomers of compounds of the present invention may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

The invention also contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers are included in the scope of the invention.

Accordingly, one aspect of the invention relates to a group of compounds of formula (I), (Ia), (I-i), (I-ii), (Ia-i), or (Ia-ii) wherein W is O or $CH_2$.

Another aspect of the invention is directed to a group of compounds of formula (I), (Ia), (I-i), (I-ii), (Ia-i), or (Ia-ii) wherein W is $CH_2$.

A further aspect of the invention relates to a group of compounds of formula (I), (Ia), (I-i), (I-ii), (Ia-i), or (Ia-ii) wherein W is O.

Within each one of the groups of compounds described in the preceding paragraphs, $R^1$, $R^2$, $R^3$, and $R^4$ are as disclosed in the Summary and in specific embodiments herein.

For example, within each of the foregoing compounds, examples of a subgroup include those having formula (I), (Ia), (I-i), (I-ii), (Ia-i), or (Ia-ii) wherein $R^1$ is optionally substituted phenyl and $R^2$ is hydrogen, and the optional substituents of the phenyl group have meanings as disclosed in the Summary and in specific embodiments herein. Particularly, the phenyl group is substituted, preferably with 1, 2, or 3 substituents as described herein above.

Examples of another subgroup include those having formula (I), (Ia), (I-i), (I-ii), (Ia-i), or (Ia-ii) wherein $R^1$ is an optionally substituted monocyclic heteroaryl and $R^2$ is hydrogen, and the optional substituents of the monocyclic heteroaryl have meanings as disclosed in the Summary and in specific embodiments herein. Furanyl (including furan-2-yl), thienyl (including thien-2-yl and thien-3-yl) and pyridinyl (including pyridin-2-yl, pyridin-3-yl), each of which is optionally substituted.

Examples of yet another subgroup include those having formula (I), (Ia), (I-i), (I-ii), (Ia-i), or (Ia-ii) wherein $R^1$ is optionally substituted monocyclic cycloalkenyl and $R^2$ is hydrogen. An example of the cycloalkenyl includes, but is not limited to, optionally substituted cyclohexenyl (e.g. cyclohex-1-en-yl).

Of all the examples of group and subgroup of compounds of formula (IT), (Ia), (I-i), (I-ii), (Ia-i), or (Ia-ii) discussed herein above, $R^3$ and $R^4$ have values as disclosed in the Summary and the Detailed Description. For example, $R^3$ is alkyl, alkenyl, —CN, halogen, —$OR^a$, —$SF_5$, —$S(O)_2R^b$, haloalkyl, —$(CR^eR^f)_m$—CN, and an optionally substituted cycloalkyl; wherein m, $R^a$, $R^b$, $R^e$, and $R^f$ are as described in the Summary. For example, $R^a$ and $R^b$, are each independently alkyl (e.g. methyl) or haloalkyl (e.g. trifluoromethyl). Each occurrence of $R^e$ and $R^f$, for example, are each independently hydrogen or alkyl (e.g. methyl). Particular examples of the substituents of $R^1$ include, but are not limited to, $C_1$-$C_4$ alkyl (e.g. methyl, ethyl, tert-butyl), $C_2$-$C_3$ alkenyl (e.g. 2-methyl-2-propenyl), —CN, halogen (e.g. F, Cl, Br), —$OCH_3$, —$OCF_3$, —$SF_5$, —$S(O)_2(CF_3)$, trifluoromethyl, difluoromethyl, —$C(CH_3)_2$—CN, and an optionally substituted cyclopropyl $R^4$, for example, is methyl, ethyl, —CN, or difluoromethyl. In certain embodiments, $R^4$ is methyl or ethyl. In other embodiments, $R^4$ is $C_1$-$C_2$ haloalkyl such as, but not limited to, difluoromethyl. In yet other embodiments, $R^4$ is —CN.

Exemplary compounds of the present invention include, but are not limited to:

8-({5-[3-fluoro-4-(trifluoromethyl)phenyl]-4-methyl-1,3-oxazol-2-yl}amino)-1,2,3,4-tetrahydronaphthalen-2-ol;

8-({5-[3,4-bis(trifluoromethyl)phenyl]-4-methyl-1,3-oxazol-2-yl}amino)-1,2,3,4-tetrahydronaphthalen-2-ol;

8-({5-[2,4-bis(trifluoromethyl)phenyl]-4-methyl-1,3-oxazol-2-yl}amino)-1,2,3,4-tetrahydronaphthalen-2-ol;

8-({5-[2-methoxy-4-(trifluoromethyl)phenyl]-4-methyl-1,3-oxazol-2-yl}amino)-1,2,3,4-tetrahydronaphthalen-2-ol;

8-({5-[2-fluoro-4-(trifluoromethyl)phenyl]-4-methyl-1,3-oxazol-2-yl}amino)-1,2,3,4-tetrahydronaphthalen-2-ol;

8-({5-[2,3-difluoro-4-(trifluoromethyl)phenyl]-4-methyl-1,3-oxazol-2-yl}amino)-1,2,3,4-tetrahydronaphthalen-2-ol;

8-[(4-methyl-5-thien-3-yl-1,3-oxazol-2-yl)amino]-1,2,3,4-tetrahydronaphthalen-2-ol;

8-[(4-methyl-5-thien-2-yl-1,3-oxazol-2-yl)amino]-1,2,3,4-tetrahydronaphthalen-2-ol;

8-({4-methyl-5-[4-(trifluoromethoxy)phenyl]-1,3-oxazol-2-yl}amino)-1,2,3,4-tetrahydronaphthalen-2-ol;

8-{[5-(4-tert-butylphenyl)-4-methyl-1,3-oxazol-2-yl]amino}-1,2,3,4-tetrahydronaphthalen-2-ol;
8-{[4-methyl-5-(4-methylphenyl)-1,3-oxazol-2-yl]amino}-1,2,3,4-tetrahydronaphthalen-2-ol;
8-({4-methyl-5-[4-(trifluoromethyl)phenyl]-1,3-oxazol-2-yl}amino)-1,2,3,4-tetrahydronaphthalen-2-ol;
8-{[5-(4-chlorophenyl)-4-methyl-1,3-oxazol-2-yl]amino}-1,2,3,4-tetrahydronaphthalen-2-ol;
8-{[5-(4-methoxyphenyl)-4-methyl-1,3-oxazol-2-yl]amino}-1,2,3,4-tetrahydronaphthalen-2-ol;
4-{2-[(7-hydroxy-5,6,7,8-tetrahydronaphthalen-1-yl)amino]-4-methyl-1,3-oxazol-5-yl}benzonitrile;
8-{[5-(4-bromophenyl)-4-methyl-1,3-oxazol-2-yl]amino}-1,2,3,4-tetrahydronaphthalen-2-ol;
8-{[5-(3,4-dichlorophenyl)-4-methyl-1,3-oxazol-2-yl]amino}-1,2,3,4-tetrahydronaphthalen-2-ol;
8-{[5-(4-fluorophenyl)-4-methyl-1,3-oxazol-2-yl]amino}-1,2,3,4-tetrahydronaphthalen-2-ol;
8-{[5-(4-chloro-2-methylphenyl)-4-methyl-1,3-oxazol-2-yl]amino}-1,2,3,4-tetrahydronaphthalen-2-ol;
8-{[5-(4-bromo-2-fluorophenyl)-4-methyl-1,3-oxazol-2-yl]amino}-1,2,3,4-tetrahydronaphthalen-2-ol;
(2R)-8-({4-methyl-5-[4-(trifluoromethyl)phenyl]-1,3-oxazol-2-yl}amino)-1,2,3,4-tetrahydronaphthalen-2-ol;
(2S)-8-({4-methyl-5-[4-(trifluoromethyl)phenyl]-1,3-oxazol-2-yl}amino)-1,2,3,4-tetrahydronaphthalen-2-ol;
8-({4-methyl-5-[6-(trifluoromethyl)pyridin-3-yl]-1,3-oxazol-2-yl}amino)-1,2,3,4-tetrahydronaphthalen-2-ol;
(2R)-8-({5-[2-fluoro-4-(trifluoromethyl)phenyl]-4-methyl-1,3-oxazol-2-yl}amino)-1,2,3,4-tetrahydronaphthalen-2-ol;
(2S)-8-({5-[2-fluoro-4-(trifluoromethyl)phenyl]-4-methyl-1,3-oxazol-2-yl}amino)-1,2,3,4-tetrahydronaphthalen-2-ol;
8-{[5-(4-bromo-3-fluorophenyl)-4-methyl-1,3-oxazol-2-yl]amino}-1,2,3,4-tetrahydronaphthalen-2-ol;
8-{[5-(3-fluoro-4-methylphenyl)-4-methyl-1,3-oxazol-2-yl]amino}-1,2,3,4-tetrahydronaphthalen-2-ol;
8-({4-methyl-5-[5-(trifluoromethyl)-2-furyl]-1,3-oxazol-2-yl}amino)-1,2,3,4-tetrahydronaphthalen-2-ol;
8-({5-[(4R)-4-isopropenylcyclohex-1-en-1-yl]-4-methyl-1,3-oxazol-2-yl}amino)-1,2,3,4-tetrahydronaphthalen-2-ol;
8-{[5-(5-ethylthien-2-yl)-4-methyl-1,3-oxazol-2-yl]amino}-1,2,3,4-tetrahydronaphthalen-2-ol;
(2R)-8-({4-methyl-5-[5-(trifluoromethyl)pyridin-2-yl]-1,3-oxazol-2-yl}amino)-1,2,3,4-tetrahydronaphthalen-2-ol;
2-(4-{2-[(7-hydroxy-5,6,7,8-tetrahydronaphthalen-1-yl)amino]-4-methyl-1,3-oxazol-5-yl}phenyl)-2-methylpropanenitrile;
8-{[5-(4-cyclopropyl-3-fluorophenyl)-4-methyl-1,3-oxazol-2-yl]amino}-1,2,3,4-tetrahydronaphthalen-2-ol;
8-{[5-(4-chloro-3-fluorophenyl)-4-methyl-1,3-oxazol-2-yl]amino}-1,2,3,4-tetrahydronaphthalen-2-ol;
8-({5-[4-(difluoromethyl)phenyl]-4-methyl-1,3-oxazol-2-yl}amino)-1,2,3,4-tetrahydronaphthalen-2-ol;
(2R)-8-({5-[4-(difluoromethyl)phenyl]-4-methyl-1,3-oxazol-2-yl}amino)-1,2,3,4-tetrahydronaphthalen-2-ol;
8-({4-methyl-5-[4-(pentafluoro-lambda-6-sulfanyl)phenyl]-1,3-oxazol-2-yl}amino)-1,2,3,4-tetrahydronaphthalen-2-ol;
(2R)-8-{[5-(4-chloro-3-fluorophenyl)-4-methyl-1,3-oxazol-2-yl]amino}-1,2,3,4-tetrahydronaphthalen-2-ol;
(2R)-8-{[5-(4-bromo-3-fluorophenyl)-4-methyl-1,3-oxazol-2-yl]amino}-1,2,3,4-tetrahydronaphthalen-2-ol;
(2R)-8-({4-ethyl-5-[4-(trifluoromethyl)phenyl]-1,3-oxazol-2-yl}amino)-1,2,3,4-tetrahydronaphthalen-2-ol;
8-{[5-(5-bromopyridin-2-yl)-4-ethyl-1,3-oxazol-2-yl]amino}-1,2,3,4-tetrahydronaphthalen-2-ol;
8-({5-[3-chloro-4-(trifluoromethyl)phenyl]-4-methyl-1,3-oxazol-2-yl}amino)-1,2,3,4-tetrahydronaphthalen-2-ol;
8-({4-ethyl-5-[2-fluoro-4-(trifluoromethyl)phenyl]-1,3-oxazol-2-yl}amino)-1,2,3,4-tetrahydronaphthalen-2-ol;
8-{[5-(4-bromophenyl)-4-ethyl-1,3-oxazol-2-yl]amino}-1,2,3,4-tetrahydronaphthalen-2-ol;
(2R)-8-({4-ethyl-5-[2-fluoro-4-(trifluoromethyl)phenyl]-1,3-oxazol-2-yl}amino)-1,2,3,4-tetrahydronaphthalen-2-ol;
(2S)-8-({4-ethyl-5-[2-fluoro-4-(trifluoromethyl)phenyl]-1,3-oxazol-2-yl}amino)-1,2,3,4-tetrahydronaphthalen-2-ol;
(2S)-8-({4-ethyl-5-[4-(trifluoromethyl)phenyl]-1,3-oxazol-2-yl}amino)-1,2,3,4-tetrahydronaphthalen-2-ol;
5-({4-methyl-5-[4-(trifluoromethyl)phenyl]-1,3-oxazol-2-yl}amino)chroman-3-ol;
(2S)-8-({4-(difluoromethyl)-5-[4-(trifluoromethyl)phenyl]-1,3-oxazol-2-yl}amino)-1,2,3,4-tetrahydronaphthalen-2-ol;
(2R)-8-({4-(difluoromethyl)-5-[4-(trifluoromethyl)phenyl]-1,3-oxazol-2-yl}amino)-1,2,3,4-tetrahydronaphthalen-2-ol;
(2R)-8-({5-[4-(difluoromethyl)phenyl]-4-ethyl-1,3-oxazol-2-yl}amino)-1,2,3,4-tetrahydronaphthalen-2-ol;
(2S)-8-({5-[4-(difluoromethyl)phenyl]-4-ethyl-1,3-oxazol-2-yl}amino)-1,2,3,4-tetrahydronaphthalen-2-ol;
2-{[(7R)-7-hydroxy-5,6,7,8-tetrahydronaphthalen-1-yl]amino}-5-[4-(trifluoromethyl)phenyl]-1,3-oxazole-4-carbonitrile;
(2R)-8-{[5-(5-bromopyridin-2-yl)-4-methyl-1,3-oxazol-2-yl]amino}-1,2,3,4-tetrahydronaphthalen-2-ol;
(2R)-8-({5-[2,3-difluoro-4-(trifluoromethyl)phenyl]-4-methyl-1,3-oxazol-2-yl}amino)-1,2,3,4-tetrahydronaphthalen-2-ol;
(2R)-8-{[5-(4-bromophenyl)-4-ethyl-1,3-oxazol-2-yl]amino}-1,2,3,4-tetrahydronaphthalen-2-ol; and
(2S)-8-{[5-(4-bromophenyl)-4-ethyl-1,3-oxazol-2-yl]amino}-1,2,3,4-tetrahydronaphthalen-2-ol;

c. Biological Data (i) In Vitro Data—Determination of Inhibition Potencies

Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 mg/l Na pyruvate, without phenol red), L-glutamine, hygromycin B, and Lipofectamine® were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methy lphenoxy]ethoxy]phenyl]-N-[2-[(acetyloxy)methoxy]-2-oxyethyl]-glycine, (acetyloxy)methyl ester) was purchased from Molecular Probes (Eugene, Oreg.).

The cDNAs for the human TRPV1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain Vol. 88 pages 205-215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hTRPV1 cDNA were transfected individually into 1321N1 human astrocytoma cells using Lipofectamine®. Forty-eight hours after transfection, the neomycin-resistant cells were selected with growth medium containing 800 μg/mL Geneticin (Gibco BRL). Surviving individual colonies were isolated and screened for TRPV1 receptor activity. Cells expressing recombinant homomeric TRPV1 receptors were maintained at 37° C. in D-MEM containing 4 mM L-glutamine, 300 μg/mL G418 (Cal-biochem) and 10% fetal bovine serum under a humidified 5% $CO_2$ atmosphere.

The functional activity of compounds at the TRPV1 receptor was determined with a $Ca^{2+}$ influx assay and measurement of intracellular $Ca^{2+}$ levels ($[Ca^{2+}]_i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 μM solution of the TRPV1 agonist capsaicin was also prepared in D-PBS. The fluorescent $Ca^{2+}$ chelating dye Fluo-4 AM was used as an indicator of the relative levels of $[Ca^{2+}]_i$ in a 96-well format using a Fluorescence Imaging Plate Reader (FLIPR)(Molecular Devices, Sunnyvale, Calif.). Cells were grown to confluency in 96-well black-walled tissue culture plates. Then, prior to the assay, the cells were loaded with 100 μL per well of Fluo-4 AM (2 μM, in D-PBS) for 1-2 hours at 23° C. Washing of the cells was performed to remove extracellular Fluo-4 AM (2×1 mL D-PBS per well), and afterward, the cells were placed in the reading chamber of the FLIPR instrument. 50 μL of the compound solutions were added to the cells at the 10 second time mark of the experimental run. Then, after a 3-minute time delay, 50 μL of the capsaicin solution was added at the, 190 seconds time mark (0.05 μM final concentration)(final volume=200 μL) to challenge the TRPV1 receptor. Time length of the experimental run was 240 seconds. Fluorescence readings were made at 1 to 5 second intervals over the course of the experimental run. The peak increase in relative fluorescence units (minus baseline) was calculated from the 190 seconds time mark to the end of the experimental run, and expressed as a percentage of the 0.05 μM capsaicin (control) response. Curve-fits of the data were solved using a four-parameter logistic Hill equation in GraphPad Prism® (GraphPad Software, Inc., San Diego, Calif.), and $IC_{50}$ values were calculated.

The results are shown in Table 1.

Certain compounds of the invention were tested in the assay described above and are effective TRPV1 antagonists with $IC_{50}$ values from about 10 μM to about 10 nM, for example, from about 1 μM to about 10 nM, and preferably, from about 200 nM to about 10 nM.

(ii) Pharmacokinetic Data

Groups of three fasted male Sprague-Dawley rats received a 30 μmol/kg (2 ml/kg) oral dose of the test compound, administered by gavage. The compounds were prepared as a solution in a 10% DMSO/poly(ethylene glycol)-400 (v/v). Blood and brain samples were obtained from each animal two hours after dosing.

Rat brain tissue was homogenized with two parts water (by weight). Test compound was selectively extracted from plasma and brain homogenate using liquid-liquid extraction with tert-butylmethylether. The compounds of interest were separated from co-extracted contaminants on a 50×3 mm, Luna CN column (Phenomenex), with an acetonitrile:0.1% aqueous trifluoroacetic acid mobile phase at a flow rate of 0.35 ml/min. Plasma and tissue concentrations were determined by HPLC-MS/MS on an API2000 with Turbo Ion Spray interface, with MRM detection in the positive ionization mode. To calibrate compound concentration, a separate portion of each tissue sample was spiked with a known quantity of test compound and analyzed simultaneously with the samples. The results are shown in Table 1.

TABLE 1

| Compound | $IC_{50}$ (nM) | [Plasma], (μg/mL) | [Brain], (μg/g) | [Brain]/ [Plasma] |
|---|---|---|---|---|
| A | 22 | 0.0 | 0.0 | 0 |
| 5 | 43 | 0.21 | 0.66 | 3.0 |
| 6 | 62 | 0.13 | 0.23 | 1.7 |
| 9 | 184 | 0.51 | 2.1 | 4.0 |
| 12 | 36 | 0.49 | 3.3 | 6.3 |
| 13 | 108 | 0.093 | 0.60 | 5.6 |
| 15 | 36 | 0.25 | 0.31 | 1.3 |
| 31* | 703 | 0.04 | 0.05 | 1.3 |
| 32* | 395 | 0.009 | 0.015 | 1.9 |
| 40* | 52 | 0.11 | 0.16 | 1.4 |
| 43* | 74 | 0.14 | 0.41 | 2.8 |
| 51* | 618 | 0.30 | 0.80 | 2.7 |
| 53* | 38 | 0.27 | 0.93 | 3.4 |

*denotes compound dosed at 10 μmol/kg PO

In Table 1, Compound A is 8-({5-[4-(trifluoromethyl)phenyl]-1,3-oxazol-2-yl}amino)-1,2,3,4-tetrahydronaphthalen-2-ol, a compound that is disclosed as Example 2 in the U.S. Patent Publication No. 2006/0281799.

As is apparent from the experimental results given in Table 1, compounds of the invention are superior to Compound A in CNS penetration, as demonstrated by the brain concentration levels and the brain:plasma ratio after oral administration, while comparable to Compound A in potency. These results suggest that compounds of the invention are of value as better therapeutic agents for the treatment of pain, particularly in pain mediated by central sensitization such as chronic inflammatory pain and osteoarthritic pain.

d. Methods of Using the Compounds

One embodiment of the present invention provides a method for treating a disorder that may be ameliorated by inhibiting vanilloid receptor subtype 1 (TRPV1) receptor in a host mammal in need of such treatment. The method comprises administering a therapeutically effective amount of a compound of formula (I) or a pharmaceutically acceptable salt thereof.

Another embodiment of the present invention provides a method for treating pain in a mammal in need of such treatment. This method comprises administering a therapeutically effective amount of a compound of formula (I) or a pharmaceutically acceptable salt thereof.

Yet another embodiment of the present invention provides a method of treating ischemia including acute cerebral ischemia, pain including chronic pain, neuropathic pain, nociceptive pain, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, visceral pain, cancer pain, dental pain, headache, migraine, carpal tunnel syndrome, fibromyalgia, neuritis, sciatica, pelvic hypersensitivity, pelvic pain, menstrual pain, bladder disease, such as incontinence and bladder overactivity, micturition disorder, renal colic; and cystitis; inflammation such as burns, rheumatoid arthritis and osteoarthritis; neurodegenerative disease such as stroke, post stroke pain and multiple sclerosis; pulmonary disease such as asthma, cough, chronic obstructive pulmonary disease (COPD) and bronchoconstriction; gastrointestinal disease such as gastroesophageal reflux disease (GERD), dysphagia, ulcer, irritable bowel syndrome (IBS), inflammatory bowel disease (IBD), colitis and Crohn's disease; ischemia such as cerebrovascular ischemia; emesis such as cancer chemotherapy-induced emesis, and obesity, in mammals, especially humans. For example, the compounds of the invention are useful for the treatment of pain, particularly nociceptive and inflammatory pain. This method comprises the step of administering a therapeutically effective amount of a compound of formula (I) or a pharmaceutically acceptable salt thereof, to a subject in need thereof.

Compounds of the present invention, including but not limited to those specified in the examples, can be used to treat pain as demonstrated by Nolano, M. et al., Pain 81:135 (1999); Caterina, M. and Julius, D., Annu. Rev. Neurosci. 24:487-517 (2001); Caterina, M. et al., Science 288:306-313 (2000); Caterina, M. et al., Nature 389:816-824 (1997); and Cui et al., J. of Neuroscience, 26:9385-9393 (2006).

Compounds of the present invention, including but not limited to those specified in the examples, can be used to treat bladder overactivity and/or urinary incontinence as demonstrated by Fowler, C. Urology 55:60 (2000).

Compounds of the present invention, including but not limited to those specified in the examples, can be used to treat inflammatory thermal hyperalgesia as demonstrated by Davis, J. et al., Nature 405:183-187 (2000).

Compounds of the present invention, including but not limited to those specified in the examples, can be used as for the treatment of anxiety-related disorders as demonstrated by Marsch, R. et al., J. Neuroscience 27:832-839 (2007).

Compounds of the present invention, including but not limited to those specified in the examples, can be used as for the treatment of disorders associated with hyperdopaminergia such as psychosis, attention deficit hyperactivity disorder and schizophrenia as demonstrated by Tzavara, E. et al., Biol. Psychiatry 59:508-515 (2006).

Compounds of the invention may be administered alone, or in combination with one or more other compounds of the invention, or in combination (i.e. co-administered) with one or more additional pharmaceutical agents. For example, a compound of formula (I) or a pharmaceutically acceptable salt or solvate thereof, may be administered in combination with one or more analgesic agents selected from the group consisting of nonsteroidal anti-inflammatory drug (NSAID) and acetaminophen, or a combination thereof. Examples of nonsteroidal anti-inflammatory drug (NSAID) include, but are not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. Combination therapy includes administration of a single pharmaceutical dosage formulation containing one or more of the compounds of invention and one or more additional pharmaceutical agents, as well as administration of the compounds of the invention and each additional pharmaceutical agent, each in its own separate pharmaceutical dosage formulation. For example, a compound of formula (I) and one or more additional pharmaceutical agent, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 μg/kg body weight to about 50 mg/kg body weight. More preferable doses can be in the range of from about 0.10 μg/kg body weight to about 3 mg/kg body weight. (Please verify the ranges) If desired, the effective daily dose can be divided into multiple doses for purposes of administration. Consequently, single dose compositions may contain such amounts or submultiples thereof to make up the daily dose.

e. Pharmaceutical Compositions

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising a compound of formula (I), or a pharmaceutically acceptable salt thereof, and one or more pharmaceutically acceptable carriers, alone or in combination with one or more nonsteroidal anti-inflammatory drug (NSAID).

The pharmaceutical compositions of the invention can be used for the treatment of the disorders as described herein in mammals including human.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of the present invention can be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66:1 et seq).

The compounds of the invention may contain either a basic or an acidic functionality, or both, and can be converted to a pharmaceutically acceptable salt, when desired, by using a suitable acid or base. The salts can be prepared in situ during the final isolation and purification of the compounds of the invention.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups W, $R^1$, $R^2$, $R^3$ and $R^4$ have the meanings as set forth in the summary section and Detailed description unless otherwise noted, can be synthesized as shown in Schemes 1-4.

As used in the descriptions of the schemes and the examples, certain abbreviations are intended to have the following meanings: BINAP for 2,2'-bis(diphenylphosphino)-1,1'-binaphthyl, BuOH for n-butanol, dppf for 1,1'-bis(diphenylphosphino)ferrocene, $Et_2O$ for diethyl ether, EtOH for ethanol, EtOAc for ethyl acetate, $Et_3N$ for triethyl amine, Et for ethyl, LAH for lithium aluminum hydride, mCPBA for 3-chloroperbenzoic acid, NaHMDS for sodium bis(trimethylsilyl)amide, MeOH for methanol, $Pd(PPh_3)_4$ for tetrakis(triphenylphosphine)palladium(0), Ph for phenyl, for TBS for tert-butyldimethylsilyl, THF for tetrahydrofuran, DMF for N,N-dimethylformamide, DMSO for dimethyl sulfoxide, and HPLC for high performance liquid chromatography.

Compounds of general formula (I) wherein $R^2$ is hydrogen can be prepared using general procedures as illustrated in Scheme 1.

the enantiomers of (1) wherein P is a hydrogen atom or a tert-butyldiphenylsilyl group are shown in Examples 24, 25, and 26.

Intermediates of formula (2) wherein $R^4$ is methyl or ethyl can be prepared as illustrated in Scheme 2.

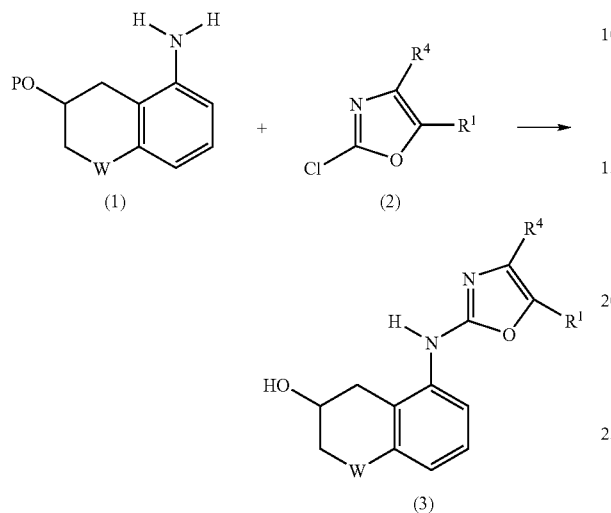

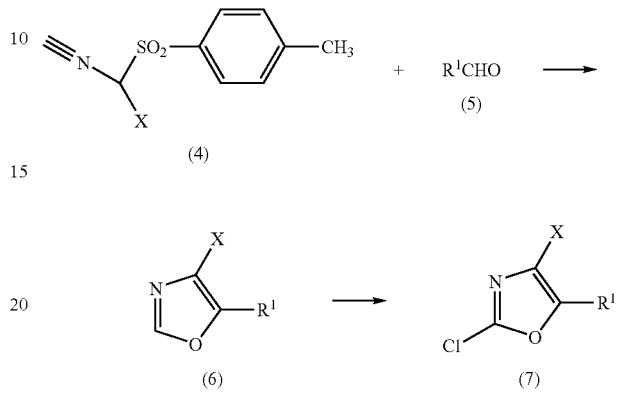

The reaction of producing compound (3) from compound (1) wherein P is a hydrogen atom or a hydroxy protecting group such as, but not limited to, TBS or tert-butyldiphenylsilyl, and (2) is generally conducted in a solvent such as n-butanol or isopropyl alcohol, at a temperature ranging from about 50° C. to about 120° C. Alternatively, coupling of (1) and (2) can be carried out in acetonitrile under microwave condition at a temperature ranging from about 100° C. to about 150° C. In preparing certain compounds of formula (3), the presence of a catalytic amount of acid such as, but not limited to, hydrochloric acid, trifluoroacetic acid, and p-toluenesulfonic acid is beneficial in selectively coupling the amino functionality of (1) to (2). It may sometimes be necessary to cool the reaction mixture after the coupling and then subject the reaction mixture to an acid such as, but not limited to, hydrochloric acid or hydrogen fluoride-triethylamine complex to facilitate complete removal of the hydroxy protecting group. Single enantiomers of (3) can be separated by chiral HPLC using a chiral column such as, but not limited to, a Chiralpak AD-H column and using methanol/$CO_2$ as eluant.

Alternatively, the single enantiomer of compounds of formula (3) can be prepared by coupling substantially pure single enantiomer of (1) with compound (2). Preparations of Compound (6) wherein X is methyl or ethyl when subjected to a base such as lithium bis(trimethylsilyl)amide to generate the corresponding anion, followed by reaction with hexachloroethane, provide compounds of formula (7). The reaction is generally conducted in a solvent such as tetrahydrofuran. Addition of the reagents is generally carried out at low temperature, for example, at about −78° C. The reaction mixture is subsequently stirred at about room temperature.

Compound (6) wherein X is methyl or ethyl can be obtained from the reaction of compound (4) with aldehyde (5) in the presence of a base such as potassium carbonate, and in a solvent such as methanol, at a temperature ranging from about 50° C. to about 100° C. Utilizing similar reaction conditions, compounds of formula (6) wherein X is hydrogen can be obtained from the reaction of aldehydes (5) with p-toluenesulfonylmethyl isocyanide. Compounds (6) wherein X is hydrogen can be transformed to compound (6) wherein X is methyl by stepwise reaction of (a) treatment with a base such as n-butyl lithium, followed by treatment with bromine; and (b) treating the product from step (a) with dimethylzinc in the presence of a palladium catalyst such as [1,1'-bis(diphenylphosphino)ferrocene]dichloropalladium(II). Step (a) is generally carried out in a solvent mixture such as tetrahydrofuran 1,3-dimethyl-3,4,5,6-tetrahydro-2(1H)-pyrimidinone, at a temperature ranging from about −78° C. to about room temperature. Step (b) is generally conducted in a solvent such as dioxane at a temperature ranging from about 50° C. to about 100° C.

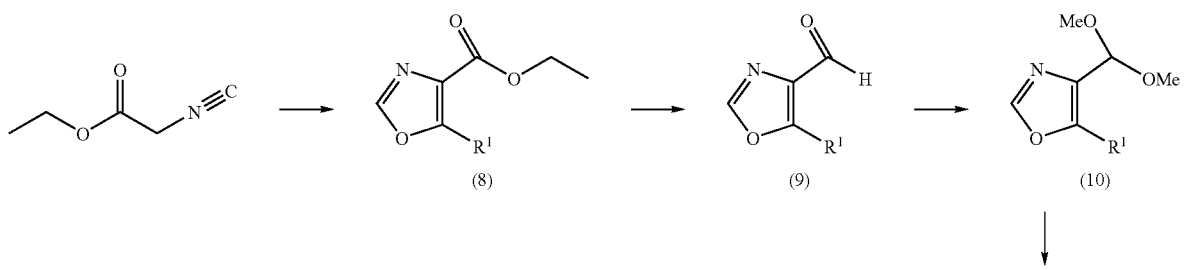

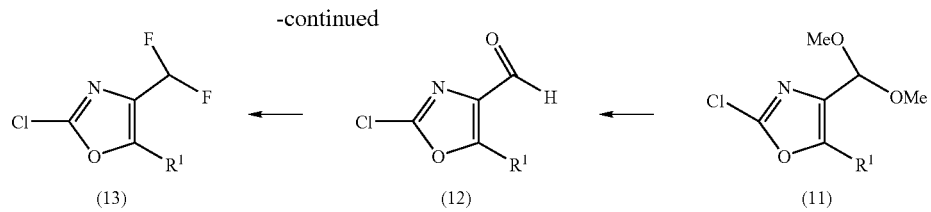

(13)   (12)   (11)

2-chloro-oxazoles of formula (13) can be prepared from chlorides of formula R¹C(O)Cl and ethyl-2-isocyanoacetate utilizing general procedures as illustrated in Scheme 3.

Treatment of R¹C(O)Cl with ethyl-2-isocyanoacetate at ambient temperature, in a solvent such as, but not limited to tetrahydrofuran, provides intermediates (8). Reduction of (8) with a reducing agent such as, but not limited to, diisobutylaluminum hydride under reaction conditions known to one skilled in the art, produces aldehydes of formula (9). Treatment of (9) with methoxytrimethylsilane and trimethylsilyltrifluoromethane sulfonate at a temperature ranging from about −78° C. to about room temperature, affords (10) which is subsequently chlorinated using reaction conditions as described in Scheme 2. When subjected to an acid such as, but not limited to, oxalic acid, (11) can be transformed to the corresponding aldehydes (12). Intermediates (13) can be obtained by reacting (12) with [bis(2-methoxyethyl)amino] sulfur trifluoride in a suitable solvent such as, but not limited to, dichloromethane, at about 0° C.

Scheme 4

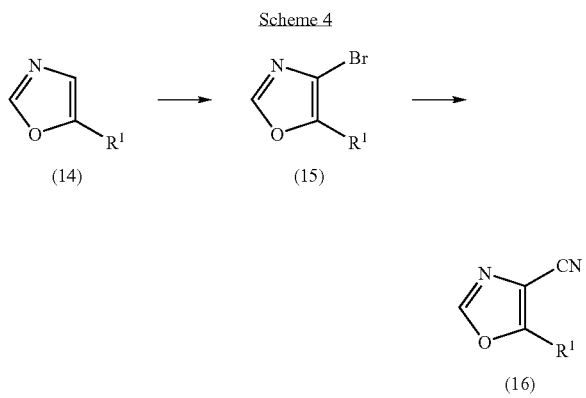

(14)   (15)

(16)

Oxazoles of formula (14), obtained from reactions as outlined in Scheme 2, when treated with a base such as n-butyl lithium, followed by treatment with bromine, produces intermediates (15). (15) can be converted to (16) by reaction with dicyanozinc and tetrakis(triphenylphosphine)palladium(0), at an elevated temperature ranging from about 80° C. to about 160° C. The reaction can also be facilitated with microwave irradiation.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

g) Examples

Example 1

8-({5-[3-fluoro-4-(trifluoromethyl)phenyl]-4-methyl-1,3-oxazol-2-yl}amino)-1,2,3,4-tetrahydronaphthalen-2-ol

Example 1A

7-{[tert-butyl(dimethyl)silyl]oxy}-5,6,7,8-tetrahydronaphthalen-1-amine

A mixture of 8-amino-2-naphthol (47.55 g, 298.7 mmol), Raney nickel (20.20 g), and 50% aq. NaOH (1.97 g) in ethanol (480 mL) in a sealed reactor was purged three times (3×40 psi $H_2$/vacuum cycles), then the reactor was pressurized with 1300 psi $H_2$ and heated at 85° C. for 7 hours. After this time, the catalyst was filtered off (Celite), and the filtrate was evaporated to afford a dark oil. The oil was dissolved in $CH_2Cl_2$ (600 mL) and was treated with imidazole (65.9 g, 969 mmol) and tert-butylchlorodimethylsilane (59.0 g, 392 mmol). The reaction mixture was stirred at room temperature for 18 hours, and washed with water and brine. The organic solution was dried over $Na_2SO_4$ and evaporated. The residue was chromatographed on silica gel (9:1 to 4:1 hexane-ethyl acetate, eluant) to afford the title compound as a dark purple oil, 44.22 g (49%). $^1$H NMR (300 MHz, DMSO-$d_6$) δ 6.76 (m, 1H), 6.40 (m, 1H), 6.27 (d, J=7.5 Hz, 1H), 4.68 (br, 2H), 4.07 (m, 1H), 2.57-2.79 (m, 3H), 2.22 (m, 1H), 1.81 (m, 1H), 1.58 (m, 1H), 0.87 (s, 9H), 0.08 (s, 6H). MS (ESI$^+$) m/z 278 (M+H)$^+$.

Example 1B

5-[3-fluoro-4-(trifluoromethyl)phenyl]-4-methyl-1,3-oxazole

A mixture of 3-fluoro-4-(trifluoromethyl)benzaldehyde (0.96 g, 5.0 mmol), 1-(1-isocyanoethylsulfonyl)-4-methylbenzene (1.05 g, 5.00 mmol), and potassium carbonate (0.898 g, 6.50 mmol) was heated to reflux for 2 hours in methanol (25 mL). After this time, the reaction mixture was cooled to room temperature and poured into water, then extracted with ether. Chromatography on silica gel (20 to 40% ethyl acetate-hexane, eluant) afforded the title compound as an off-white solid (1.01 g, 82% yield). $^1$H NMR (300 MHz, DMSO-$d_6$) δ 8.48 (s, 1H), 7.90 (m, 1H), 7.68 (m, 2H), 2.43 (s, 3H). MS (DCI$^+$) m/z 246 (M+H), 263 (M+NH$_4$).

Example 1C 2-chloro-5-[3-fluoro-4-(trifluoromethyl)phenyl]-4-methyl-1,3-oxazole A solution of Example 1B (1.01 g, 4.12 mmol) in tetrahydrofuran (20 mL) was cooled to −78° C., then lithium bis(trimethylsilyl)amide (1M in tetrahydrofuran, 4.6 mL, 4.6 mmol) was added slowly. The reaction was allowed to stir at −78° C. for 20 minutes, and then hexachloroethane (1.95 g, 8.23 mmol) was added all at once. The reaction was allowed to warm to room temperature, and stir overnight. After this time, the reaction mixture was poured into water and extracted with ether. The extracts were dried over $Na_2SO_4$, filtered, and concentrated. The residue was chromatographed on silica gel (eluant of 100% hexane, then gradient to 15% ethyl acetate-hexane) to yield the title compound as a white solid (780 mg, 68% yield). $^1$H NMR (300 MHz, DMSO-$d_6$) δ 7.91 (m, 1H), 7.66 (m, 2H), 2.42 (s, 3H).

Example 1D 8-({5-[3-fluoro-4-(trifluoromethyl)phenyl]-4-methyl-1,3-oxazol-2-yl}amino)-1,2,3,4-tetrahydronaphthalen-2-ol A mixture of Example 1C (0.78 g, 2.79 mmol) and Example 1A (0.774 g, 2.79 mmol) were heated to reflux in n-butanol (14 mL) for 2 hours, cooled to room temperature and concentrated in vacuo. The residue was chromatographed on silica gel (3 to 20% methanol-$CH_2Cl_2$, eluant) to afford the title compound as an off-white solid (485 mg, 43%). $^1$H NMR (300 MHz, DMSO-$d_6$) δ 9.29 (s, 1H), 7.81 (m, 1H), 7.53 (m, 1H), 7.43 (m, 2H), 7.11 (m, 1H), 6.88 (m, 1H), 4.81 (d, J=4.0 Hz, 1H), 3.93 (m, 1H), 2.83-2.97 (m, 2H), 2.72 (m, 1H), 2.57 (m, 1H), 2.34 (s, 3H), 1.85 (m, 1H), 1.61 (m, 1H). MS (ESI$^+$) m/z 407 (M+H), 429 (M+Na). Anal. Calcd. for $C_{21}H_{18}F_4N_2O_2$: C, 62.07; H, 4.46; N, 6.89. Found: C, 61.91; H, 4.45; N, 6.80.

Example 2

8-({5-[3,4-bis(trifluoromethyl)phenyl]-4-methyl-1,3-oxazol-2-yl}amino)-1,2,3,4-tetrahydronaphthalen-2-ol The title compound was prepared according to the procedure of Example 1, substituting 3,4-bis(trifluoromethyl)benzaldehyde for 3-fluoro-4-(trifluoromethyl)benzaldehyde used in Example 1B. $^1$H NMR (300 MHz, DMSO-$d_6$) δ 9.38 (s, 1H), 8.06 (m, 1H), 7.88-7.94 (m, 2H), 7.55 (m, 1H), 7.11 (m, 1H), 6.88 (m, 1H), 4.81 (d, J=4.0 Hz, 1H), 3.92 (m, 1H), 2.68-2.99 (m, 3H), 2.54 (m, 1H), 2.37 (s, 3H), 1.86 (m, 1H), 1.61 (m, 1H). MS (ESI$^+$) m/z 457 (M+H)$^+$. Anal. Calcd. for $C_{22}H_{18}F_6N_2O_2$: C, 57.90; H, 3.98; N, 6.14. Found: 57.85; H, 3.85; N, 5.95.

Example 3

8-({5-[2,4-bis(trifluoromethyl)phenyl]-4-methyl-1,3-oxazol-2-yl}amino)-1,2,3,4-tetrahydronaphthalen-2-ol

Example 3A

5-[2,4-bis(trifluoromethyl)phenyl]-4-methyl-1,3-oxazole

The title compound was prepared according to the procedure of Example 1B, substituting 2,4-bis(trifluoromethyl)benzaldehyde for 3-fluoro-4-(trifluoromethyl)benzaldehyde.

Example 3B

5-[2,4-bis(trifluoromethyl)phenyl]-2-chloro-4-methyl-1,3-oxazole

The title compound was prepared according to the procedure of Example IC, substituting Example 3A for Example 1B.

Example 3C 8-({5-[2,4-bis(trifluoromethyl)phenyl]-4-methyl-1,3-oxazol-2-yl}amino)-1,2,3,4-tetrahydronaphthalen-2-ol A solution of Example 3B (0.648 g, 1.97 mmol) and Example 1A in n-butanol (15 mL) was heated to reflux. After 2 hours the reaction mixture was cooled to room temperature and stirred for 1 h with 15 mL of aqueous 1N HCl. After this time, saturated NaHCO$_3$ was added to increase the basicity to pH 8-9, then the aqueous mixture was extracted with ethyl acetate. The solvent was evaporated and the residue was chromatographed on silica gel (3 to 6% methanol-CH$_2$Cl$_2$, eluant) to afford a tan solid that was then triturated to give the title compound as an off-white solid (307 mg, 34%). $^1$H NMR (300 MHz, DMSO-d$_6$) δ 9.14 (s, 1H), 8.11 (m, 2H), 7.84 (m, 1H), 7.40 (m, 1H), 7.09 (t, J=7.7 Hz, 1H), 6.87 (m, 1H), 4.80 (d, J=4.0 Hz, 1H), 3.91 (m, 1H), 2.68-2.97 (m, 3H), 2.12 (s, 3H), 2.11 (m, 1H), 1.88 (m, 1H), 1.60 (m, 1H). MS (ESI$^+$) m/z 457 (M+H)$^+$. Anal. Calcd. for C$_{22}$H$_{18}$F$_6$N$_2$O$_2$: C, 57.90; H, 3.98; N, 6.14. Found: C, 57.94; H, 4.13; N, 6.10.

Example 4

8-({5-[2-methoxy-4-(trifluoromethyl)phenyl]-4-methyl-1,3-oxazol-2-yl}amino)-1,2,3,4-tetrahydronaphthalen-2-ol The title compound was prepared according to the procedure of Example 3, substituting 2-methoxy-4-(trifluoromethyl)benzaldehyde for 2,4-bis(trifluoromethyl)benzaldehyde used in Example 3A. $^1$H NMR (300 MHz, DMSO-d$_6$) δ 9.03 (s, 1H), 7.53 (m, 2H), 7.37 (m, 2H), 7.09 (t, J=7.8 Hz, 1H), 6.83 (m, 1H), 4.80 (d, J=3.7 Hz, 1H), 3.99 (m, 1H), 3.92 (s, 3H), 2.69-2.95 (m, 3H), 2.08 (m, 1H), 2.07 (s, 3H), 1.84 (m, 1H), 1.62 (m, 1H). MS (ESI$^+$) m/z 419 (M+H)$^+$. Anal. Calcd. for C$_{22}$H$_{21}$F$_3$N$_2$O$_3$: C, 63.15; H, 5.06; N, 6.70. Found: C, 63.55; H, 4.84; N, 6.34.

Example 5

8-({5-[2-fluoro-4-(trifluoromethyl)phenyl]-4-methyl-1,3-oxazol-2-yl}amino)-1,2,3,4-tetrahydronaphthalen-2-ol

Example 5A

5-[2-fluoro-4-(trifluoromethyl)phenyl]-1,3-oxazole

The title compound was prepared according to the procedure of Example 1B, substituting 2-fluoro-4-(trifluoromethyl)benzaldehyde for 3-fluoro-4-(trifluoromethyl)benzaldehyde and substituting p-toluenesulfonylmethyl isocyanide for 1-(1-isocyanoethylsulfonyl)-4-methylbenzene. $^1$H NMR (300 MHz, DMSO-d$_6$) δ 8.66 (s, 1H), 8.02 (m, 1H), 7.91 (m, 1H), 7.75 (m, 2H). MS (DCI$^+$) m/z 232 (M+H)$^+$.

Example 5B 4-bromo-5-[2-fluoro-4-(trifluoromethyl)phenyl]-1,3-oxazole

A solution of Example 5A (6.46 g, 27.9 mmol) in tetrahydrofuran (48 mL) and 1,3-dimethyl-3,4,5,6-tetrahydro-2(1H)-pyrimidinone (36 mL) was cooled to −78° C., and then treated slowly with lithium bis(trimethylsilyl)amide (1M in tetrahydrofuran, 34 mL, 34 mmol). The reaction was stirred for 1 hour and then treated dropwise with bromine (1.43 ml, 27.9 mmol). The reaction stirred for another hour at −78° C., and then was poured into 900 mL ether and 270 mL 10% Na$_2$SO$_3$ solution. The phases were separated, and the organic layer was washed with brine, dried over Na$_2$SO$_4$, filtered, and evaporated. The crude material was purified by chromatography (5 to 20% ethyl acetate-hexane) to afford the title compound as a yellow oil (4.58 g, 53% yield). $^1$H NMR (300 MHz, DMSO-d$_6$) δ 8.74 (s, 1H), 8.02 (m, 2H), 7.81 (m, 1H). MS (DCI$^+$) m/z 312 (M+H)$^+$.

Example 5C

5-[2-fluoro-4-(trifluoromethyl)phenyl]-4-methyl-1,3-oxazole

A mixture of Example 5B (4.58 g, 14.8 mmol) and [1,1'-bis(diphenylphosphino)ferrocene]dichloropalladium (II), 1:1 complex with CH$_2$Cl$_2$ (0.362 g, 0.443 mmol) in dioxane (49 mL) was treated carefully with dimethyl zinc (2M in toluene, 14.8 mL, 29.6 mmol). The reaction was heated to reflux for 2 hours, then cooled to room temperature and carefully quenched with a few milliliters of methanol. The mixture was diluted with ether and washed twice with 1N HCl and once with brine. The organic phase was dried over Na$_2$SO$_4$ and evaporated, then chromatographed (5 to 15% ethyl acetate-hexane) to afford the title compound as an orange oil (2.82 g, 78% yield). $^1$H NMR (300 MHz, DMSO-d$_6$) δ 8.52 (s, 1H), 7.87 (m, 2H), 7.74 (m, 1H), 2.27 (s, 3H). MS (DCI$^+$) m/z 246 (M+H)$^+$.

Example 5D 2-chloro-5-[2-fluoro-4-(trifluoromethyl)phenyl]-4-methyl-1,3-oxazole The title compound was prepared according to the procedure of Example 1C, substituting Example 5C for Example 1B.

Example 5E 8-({5-[2-fluoro-4-(trifluoromethyl)phenyl]-4-methyl-1,3-oxazol-2-yl}amino)-1,2,3,4-tetrahydronaphthalen-2-ol A mixture of Example 5D (1.32 g, 4.72 mmol) and Example 1A (1.31 g, 4.72 mmol) in acetonitrile (16 mL) was heated at 150° C. in a microwave reactor for 20 minutes. The solution was cooled and concentrated, and the crude material was chromatographed on silica gel (1 to 20% methanol-CH$_2$Cl$_2$ eluant). The resulting crude product was further purified by trituration with 1:1 hexane-ether, which yielded 0.278 g (14% yield) of the title compound as an off-white solid. $^1$H NMR (300 MHz, DMSO-d$_6$) δ 9.23 (s, 1H), 7.64-7.76 (m, 3H), 7.51 (m, 1H), 7.10 (t, J=7.8 Hz, 1H), 6.87 (m, 1H), 4.79 (d, J=4.0 Hz, 1H), 3.91 (m, 1H), 2.67-2.98 (m, 3H), 2.52 (m, 1H), 2.18 (s, 3H), 1.86 (m, 1H), 1.61 (m, 1H). MS (ESI$^+$) m/z 407 (M+H)$^+$, 429 (M+Na)$^+$. Anal Calcd for C$_{21}$H$_{18}$F$_4$N$_2$O$_2$: C, 62.07; H, 4.46; N, 6.89. Found: C, 61.90; H, 4.37; N, 6.85.

Example 6

8-({5-[2,3-difluoro-4-(trifluoromethyl)phenyl]-4-methyl-1,3-oxazol-2-yl}amino)-1,2,3,4-tetrahydronaphthalen-2-ol The title compound was prepared according to the procedure of Example 5, substituting 2,3-difluoro-4-(trifluoromethyl)benzaldehyde for 2-fluoro-4-(trifluoromethyl)benzaldehyde used in Example 5A. $^1$H NMR (300 MHz, DMSO-d$_6$) δ 9.34 (s, 1H), 7.65 (m, 1H), 7.44-7.52 (m, 2H), 7.10 (t, J=7.8 Hz, 1H), 6.88 (m, 1H), 4.79 (d, J=4.1 Hz, 1H), 3.91 (m, 1H), 2.65-2.97 (m, 3H), 2.20 (s, 3H), 2.16 (m, 1H), 1.85 (m, 1H), 1.61 (m, 1H). MS (ESI$^+$) m/z 425 (M+H)$^+$. Anal Calcd for C$_{21}$H$_{17}$F$_5$N$_2$O$_2$: C, 59.44; H, 4.04; N, 6.60. Found: C, 59.52; H, 3.92; N, 6.52.

Example 7

8-[(4-methyl-5-thien-3-yl-1,3-oxazol-2-yl)amino]-1,2,3,4-tetrahydronaphthalen-2-ol

Example 7A 5-thien-3-yl-1,3-oxazole

The title compound was prepared according to the procedure of Example 5A, substituting thiophene-3-carbaldehyde for 2-fluoro-4-(trifluoromethyl)benzaldehyde.

Example 7B 4-bromo-5-thien-3-yl-1,3-oxazole

The title compound was prepared according to the procedure of Example 5B, substituting Example 7A for Example 5A.

Example 7C 4-methyl-5-thien-3-yl-1,3-oxazole

The title compound was prepared according to the procedure of Example 5C, substituting Example 7B for Example 5B.

Example 7D 2-chloro-4-methyl-5-thien-3-yl-1,3-oxazole

The title compound was prepared according to the procedure of Example 1C, substituting Example 7C for Example 1B.

Example 7E

8-[(4-methyl-5-thien-3-yl-1,3-oxazol-2-yl)amino]-1,2,3,4-tetrahydronaphthalen-2-ol A mixture of Example 7D (0.425 g, 2.13 mmol) and Example 1A (0.591 g, 2.13 mmol) in acetonitrile (10 mL) was heated at 150° C. in a microwave reactor for 20 minutes. The reaction mixture was cooled to room temperature and evaporated. The residue was taken up in tetrahydrofuran (36 mL) and stirred with 6N HCl (3.6 mL) for several hours. The mixture was evaporated and the pH of the aqueous residue was increased to pH 9 with saturated NaHCO$_3$ solution. The product was extracted with ethyl acetate, and the combined extracts were dried over Na$_2$SO$_4$ and evaporated. Chromatography on silica gel (3 to 20% methanol-CH$_2$Cl$_2$ eluant) afforded a solid, which was further purified by trituration with 1:1 ether-hexane to give the title compound (0.170 g, 24% yield). $^1$H NMR (300 MHz, DMSO-d$_6$) δ 8.92 (s, 1H), 7.66 (m, 1H), 7.58 (d, J=7.8 Hz, 1H), 7.45 (m, 1H), 7.29 (m, 1H), 7.08 (t, J=7.6 Hz, 1H), 6.82 (m, 1H), 4.78 (d, J=4.1 Hz, 1H), 3.92 (m, 1H), 2.63-2.99 (m, 3H), 2.45 (m, 1H), 2.21 (s, 3H), 1.85 (m, 1H), 1.63 (m, 1H). MS (ESI$^+$) m/z 327 (M+H)$^+$. Anal. Calcd for C$_{18}$H$_{18}$N$_2$O$_2$S.0.08 CH$_2$Cl$_2$:C, 65.17; H, 5.49; N, 8.41. Found: C, 65.17; H, 5.16; N, 8.34.

Example 8

8-[(4-methyl-5-thien-2-yl-1,3-oxazol-2-yl)amino]-1,2,3,4-tetrahydronaphthalen-2-ol The title compound was prepared according to the procedure of Example 7, substituting thiophene-2-carbaldehyde for thiophene-3-carbaldehyde used in Example 7A. $^1$H NMR (300 MHz, DMSO-d$_6$) δ 9.06 (s, 1H), 7.51 (m, 2H), 7.06-7.14 (m, 3H), 6.84 (m, 1H), 4.78 (d, J=4.1 Hz, 1H), 3.92 (m, 1H), 2.65-2.98 (m, 4H), 2.23 (s, 3H), 1.86 (m, 1H), 1.62 (m, 1H). MS (ESI$^+$) m/z 327 (M+H)$^+$, 349 (M+Na)$^+$. Anal Calcd for C$_{18}$H$_{18}$N$_2$O$_2$S.0.2 CH$_3$OH: C, 65.68; H, 5.69; N, 8.42. Found: C, 65.68; H, 5.34; N, 8.14.

Example 9

8-({4-methyl-5-[4-(trifluoromethoxy)phenyl]-1,3-oxazol-2-yl}amino)-1,2,3,4-tetrahydronaphthalen-2-ol The title compound was prepared according to the procedure of Example 7, substituting 4-(trifluoromethoxy)benzaldehyde for thiophene-3-carbaldehyde used in Example 7A. $^1$H NMR (300 MHz, DMSO-d$_6$) δ 9.08 (s, 1H), 7.53-7.61 (m, 3H), 7.43 (m, 2H), 7.10 (t, J=7.9 Hz, 1H), 6.85 (m, 1H), 4.80 (d, J=4.0 Hz, 1H), 3.92 (m, 1H), 2.70-2.97 (m, 3H), 2.28 (s, 3H), 2.27 (m, 1H), 1.87 (m, 1H), 1.61 (m, 1H). MS (ESI$^+$) m/z 405 (M+H)$^+$. Anal. Calcd for C$_{21}$H$_{19}$F$_3$N$_2$O$_3$.0.04 CH$_2$Cl$_2$: C, 61.97; H, 4.72; N, 6.87. Found: C, 61.95; H, 4.60; N, 6.78.

Example 10

8-{[5-(4-tert-butylphenyl)-4-methyl-1,3-oxazol-2-yl]amino}-1,2,3,4-tetrahydronaphthalen-2-ol The title compound was prepared according to the procedure of Example 7, substituting 4-tert-butylbenzaldehyde for thiophene-3-carbaldehyde used in Example 7A. $^1$H NMR (300 MHz, DMSO-d$_6$) δ 8.96 (s, 1H), 7.58 (m, 1H), 7.44 (m, 4H), 7.09 (t, J=7.8 Hz, 1H), 6.82 (m, 1H), 4.80 (d, J=3.7 Hz, 1H), 3.91 (m, 1H), 2.67-2.93 (m, 3H), 2.26 (s, 3H), 2.16 (m, 1H), 1.85 (m, 1H), 1.61 (m, 1H), 1.30 (s, 9H). MS (ESI$^+$) m/z 377 (M+H)$^+$. Anal. Calcd. for C$_{24}$H$_{28}$N$_2$O$_2$.0.07 CH$_2$Cl$_2$: C, 75.59; H, 7.42; N, 7.32. Found: C, 75.65; H, 7.45; N, 7.30.

Example 11

8-{[4-methyl-5-(4-methylphenyl)-1,3-oxazol-2-yl]amino}-1,2,3,4-tetrahydronaphthalen-2-ol The title compound was prepared according to the procedure of Example 7, substituting 4-methylbenzaldehyde for thiophene-3-carbaldehyde used in Example 7A. $^1$H NMR (300 MHz, DMSO-d$_6$) δ 8.93 (s, 1H), 7.59 (m, 1H), 7.38 (m, 2H), 7.25 (m, 2H), 7.09 (t, J=7.8 Hz, 1H), 6.82 (m, 1H), 4.79 (d, J=4.1 Hz, 1H), 3.91 (m, 1H), 2.66-2.97 (m, 3H), 2.32 (s, 3H), 2.27 (m, 1H), 2.26 (s, 3H), 1.87 (m, 1H), 1.60 (m, 1H). MS (ESI) m/z 335 (M+H)$^+$. Anal. Calcd for C$_{21}$H$_{22}$N$_2$O$_2$.0.07 CH$_2$Cl$_2$: C, 74.35; H, 6.56; N, 8.23. Found: C, 74.45; H, 6.18; N, 7.95.

Example 12

8-({4-methyl-5-[4-(trifluoromethyl)phenyl]-1,3-oxazol-2-yl}amino)-1,2,3,4-tetrahydronaphthalen-2-ol

Example 12A 4-methyl-5-[4-(trifluoromethyl)phenyl]-1,3-oxazole

A mixture of 4-(trifluoromethyl)benzaldehyde (3.45 mL, 25.8 mmol), 1-(1-isocyanoethylsulfonyl)-4-methylbenzene (5.40 g, 25.8 mmol), and $K_2CO_3$ (4.28 g, 31.0 mmol) in methanol (125 mL) was heated to reflux. After 2.5 hours the volatiles were evaporated, and the residue was partitioned between diethyl ether and $H_2O$. The aqueous phase was extracted with diethyl ether, and the combined organic extract was washed with brine, dried ($Na_2SO_4$), and concentrated in vacuo. The crude product was purified by flash chromatography (Analogix Intelliflash 280; 10% to 30% ethyl acetate/hexanes eluant; SF65-400 g column), which yielded 4.01 g (68% yield) of the title compound as a pale yellow solid. $^1$H NMR (300 MHz, DMSO-$d_6$) δ 8.44 (s, 1H), 7.85 (m, 4H), 2.42 (s, 3H). MS (DCI$^+$) m/z 228 (M+H)$^+$.

Example 12B 2-chloro-4-methyl-5-[4-(trifluoromethyl)phenyl]-1,3-oxazole

Lithium bis(trimethylsilyl)amide (1 M in tetrahydrofuran, 19.4 mL, 19.4 mmol) was added dropwise to a solution of Example 12A (4.0 g, 17.6 mmol) in tetrahydrofuran (80 mL) at −78° C. After stirring 30 min, solid hexachloroethane (8.34 g, 35.2 mmol) was added in one portion, and the reaction was allowed to gradually warm to ambient temperature. After 16 hours the reaction was quenched with half-saturated $NH_4Cl$ solution. The product was extracted with diethyl ether, and the combined organic layer was washed with brine, dried ($MgSO_4$), filtered, and concentrated in vacuo. The residue was purified by flash chromatography (Analogix Intelliflash 280; 0% to 25% ethyl acetate/hexanes; SF65-600 g column; loading with hexane/$CH_2Cl_2$) to yield 4.69 g of the title compound as a white solid. $^1$H NMR (300 MHz, DMSO-$d_6$) δ 7.87 (m, 2H), 7.82 (m, 2H), 2.40 (s, 3H). MS (DCI$^+$) m/z 262 (M+H)$^+$.

Example 12C 8-({4-methyl-5-[4-(trifluoromethyl)phenyl]-1,3-oxazol-2-yl}amino)-1,2,3,4-tetrahydronaphthalen-2-ol A solution of Example 1A (1.08 g, 3.89 mmol) and Example 12B (1.02 g, 3.89 mmol) in 15 mL n-butanol was heated to reflux for 1.5 hours. The reaction mixture was cooled to ambient temperature and partitioned between ethyl acetate and saturated aqueous $NaHCO_3$ solution. The separated organic phase was washed with brine, dried ($Na_2SO_4$), filtered, and concentrated at the rotary evaporator to give a dark oil. Hexanes was added to the residue, and the resulting solid was collected by suction filtration, washed with hexanes and dried under vacuum. The result was 0.89 g of the title compound as a white solid. The reaction was performed again in an identical manner using a solution of Example 1A (3.12 g, 11.2 mmol) and Example 12B (2.94 g, 11.2 mmol) in 55 mL n-butanol. After the aqueous work-up described above and concentration of the solvents, hexane was added to precipitate the product. The result was 2.52 g that was combined with the material from the first reaction to afford a total of 3.41 g (58% yield) of the title compound as a white solid. $^1$H NMR (300 MHz, DMSO-$d_6$) δ 9.20 (s, 1H), 7.78 (m, 2H), 7.66 (m, 2H), 7.55 (m, 1H), 7.11 (t, J=7.8 Hz, 1H), 6.87 (m, 1H), 4.80 (d, J=3.7 Hz, 1H), 3.92 (m, 1H), 2.68-2.98 (m, 3H), 2.51 (m, 1H+DMSO), 2.33 (s, 3H), 1.87 (m, 1H), 1.61 (m, 1H). MS (ESI) m/z 389 (M+H)$^+$. Anal. Calcd for $C_{21}H_{19}F_3N_2O_2$: C, 64.94; H, 4.93; N, 7.21. Found: C, 64.54; H, 4.55; N, 6.96.

Example 13

8-{[5-(4-chlorophenyl)-4-methyl-1,3-oxazol-2-yl]amino}-1,2,3,4-tetrahydronaphthalen-2-ol

Example 13A 5-(4-chlorophenyl)-1,3-oxazole

The title compound was prepared according to the procedure of Example 5A, substituting 4-chlorobenzaldehyde for 2-fluoro-4-(trifluoromethyl)benzaldehyde.

Example 13B 4-bromo-5-(4-chlorophenyl)-1,3-oxazole

The title compound was prepared according to the procedure of Example 5B, substituting Example 13A for Example 5A.

Example 13C 5-(4-chlorophenyl)-4-methyl-1,3-oxazole

The title compound was prepared according to the procedure of Example 5C, substituting Example 13B for Example 5B.

Example 13D 2-chloro-5-(4-chlorophenyl)-4-methyl-1,3-oxazole

The title compound was prepared according to the procedure of Example 1C, substituting Example 13C for Example 1B.

Example 13E

8-{[5-(4-chlorophenyl)-4-methyl-1,3-oxazol-2-yl]amino}-1,2,3,4-tetrahydronaphthalen-2-ol A mixture of Example 13D (540 mg, 2.37 mmol) and Example 1A (657 mg, 2.37 mmol) in acetonitrile (6 mL) was heated in a microwave reactor at 150° C. for 20 minutes. The reaction was cooled and the solvent was evaporated. The residue was dissolved in tetrahydrofuran (20 mL) and 10 mL 6N HCl and the mixture was stirred several hours at ambient temperature. The mixture was then diluted with ethyl acetate, and the organic phase was washed with water, brine, dried over $Na_2SO_4$, filtered, and evaporated. The crude product was chromatographed on silica gel using methanol/$CH_2Cl_2$ as eluent (2% to 20%) that gave a solid that was further purified by trituration to afford 143 mg (17% yield) of the title compound as a white solid. $^1$H NMR (300 MHz, DMSO-$d_6$) δ 9.05 (s, 1H) 7.56 (d, J=7.12 Hz, 1H), 7.48 (s, 4H), 7.10 (t, J=7.80 Hz, 1H), 6.84 (d, J=7.12 Hz, 1H), 4.79 (d, J=3.73 Hz, 1H), 3.92 (bs, 1H), 2.97 (m, 2H), 2.68 (m, 1H), 2.26 (s, 3H), 1.87 (bs, 1H), 1.61 (bs, 1H). MS (ESI+) m/z 354 (M+H)+.

Example 14

8-{[5-(4-methoxyphenyl)-4-methyl-1,3-oxazol-2-yl]amino}-1,2,3,4-tetrahydronaphthalen-2-ol

Example 14A 5-(4-methoxyphenyl)-1,3-oxazole

The title compound was prepared according to the procedure of Example 5A, substituting 4-methoxybenzaldehyde for 2-fluoro-4-(trifluoromethyl)benzaldehyde.

Example 14B 4-bromo-5-(4-methoxyphenyl)-1,3-oxazole

The title compound was prepared according to the procedure of Example 5B, substituting Example 14A for Example 5A.

Example 14C 5-(4-methoxyphenyl)-4-methyl-1,3-oxazole

The title compound was prepared according to the procedure of Example 5C, substituting Example 14B for Example 5B.

Example 14D 2-chloro-5-(4-methoxyphenyl)-4-methyl-1,3-oxazole

The title compound was prepared according to the procedure of Example IC, substituting Example 14C for Example 1B.

Example 14E

8-{[5-(4-methoxyphenyl)-4-methyl-1,3-oxazol-2-yl]amino}-1,2,3,4-tetrahydronaphthalen-2-ol A mixture of Example 14D (0.840 g, 3.76 mmol) and Example 1A (1.04 g, 3.76 mmol) in acetonitrile (19 mL) was heated in a microwave reactor at 150° C. for 20 minutes. Two drops of aqueous concentrated HCl were added and the reaction was reheated in the microwave to 150° C. for 20 min. The volatiles were evaporated and the crude material was dissolved in tetrahydrofuran (20 mL), followed by addition of 10 mL 6N HCl. The mixture was stirred overnight at ambient temperature, then diluted with ethyl acetate. The organic phase was washed with water, brine, dried over $Na_2SO_4$, and concentrated in vacuo. The crude product was purified by chromatography on silica gel using methanol/$CH_2Cl_2$ as eluent (2% to 20%), followed by triturating with diethyl ether to afford 122 mg (9% yield) of the title compound. $^1$H NMR (300 MHz, DMSO-$d_6$) δ 8.89 (s, 1H), 7.60 (d, J=7.93 Hz, 1H), 7.42 (d, J=9.12 Hz, 2H), 7.04 (m, 3H), 6.81 (d, J=7.54 Hz, 1H), 4.80 (d, J=3.97 Hz, 1H), 3.92 (bs, 1H), 3.78 (s, 3H), 2.90 (m, 2H), 2.75 (m, 1H), 2.22 (s, 3H), 1.87 (bs, 1H), 1.62 (bs, 1H). MS (ESI) m/z 350 (M+H)+.

Example 15

4-{2-[(7-hydroxy-5,6,7,8-tetrahydronaphthalen-1-yl)amino]-4-methyl-1,3-oxazol-5-yl}benzonitrile

Example 15A 4-(4-methyl-1,3-oxazol-5-yl)benzonitrile

4-Formylbenzonitrile (1.61 g, 12.3 mmol), 1-(1-isocyanoethylsulfonyl)-4-methylbenzene (2.58 g, 12.3 mmol), and potassium carbonate (3.39 g, 24.5 mmol) in methanol (60 mL) was heated to reflux overnight. The reaction mixture was cooled and the volatiles evaporated. The residue was partitioned between water and ethyl acetate. The organic phase was washed with water and brine, dried over $Na_2SO_4$, filtered, and evaporated. The solid was chromatographed on silica gel, eluting with 10% to 50% ethyl acetate:hexanes to afford 1.70 g (75% yield) of the title compound as a white solid.

Example 15B 4-(2-chloro-4-methyl-1,3-oxazol-5-yl)benzonitrile

A solution of Example 15A (1.70 g, 9.23 mmol) in tetrahydrofuran (37 ml) was cooled to −78° C., followed by addition of lithium bis(trimethylsilyl)amide (1M, in tetrahydrofuran, 10.2 mL, 10.2 mmol). After 30 min hexchloroethane (4.37 g, 18.5 mmol) was added as a solid in one portion. The reaction was stirred overnight being allowed to warm to room temperature, and then quenched with brine, and diluted with ethyl acetate. Water was added and the product was extracted with ethyl acetate. The organic phase was washed with brine, dried over $Na_2SO_4$, filtered, and evaporated. The crude product was purified on silica gel eluting the column with 3 column volumes of hexanes, then 10 to 40% ethyl acetate/hexanes to give 1.65 g (82% yield)) of the title compound as a white solid.

Example 15C

4-{2-[(7-hydroxy-5,6,7,8-tetrahydronaphthalen-1-yl)amino]-4-methyl-1,3-oxazol-5-yl}benzonitrile A solution of Example 15B (1.36 g, 6.22 mmol) and Example 1A (1.73 g, 6.22 mmol) in 2-propanol (63 mL) was heated to reflux overnight. The reaction was cooled and the solvent evaporated. The residue was triturated with 1:1:1 hexanes:ether: $CH_2Cl_2$, followed by recrystallization from ethyl acetate and collection of the solid by filtration. The mother liquor was evaporated and the resulting solid was recrystallized from ethyl acetate. All of the solids were combined and triturated with ether and collected by filtration to give 0.986 g (46% yield) of the title compound as a light gray cotton like material. $^1$H NMR (300 MHz, DMSO-$d_6$) δ 9.27 (s, 1H), 7.86 (dJ=8.47, 2H), 7.60 (d, J=8.48 Hz, 2H), 7.52 (d, J=6.78 Hz, 1H), 7.11 (t, J=7.80 Hz, 1H), 6.88 (d, J=6.78 Hz, 1H), 4.81 (d, J=3.73 Hz, 1H), 3.92 (bs, 1H), 2.91 (m, 2H), 2.74 (m, 1H), 2.33 (s, 3H), 1.88 (bs, 1H), 1.62 (bs, 1H). MS (ESI) m/z 346 (M+H)+.

Example 16

8-{[5-(4-bromophenyl)-4-methyl-1,3-oxazol-2-yl]amino}-1,2,3,4-tetrahydronaphthalen-2-ol

Example 16A 5-(4-bromophenyl)-4-methyl-1,3-oxazole

The title compound was prepared according to the procedure of Example 15A, substituting 4-bromobenzaldehyde for 4-formylbenzonitrile.

Example 16B 5-(4-bromophenyl)-2-chloro-4-methyl-1,3-oxazole

The title compound was prepared according to the procedure of Example 15B, substituting Example 16A for Example 15A.

Example 16C

8-{[5-(4-bromophenyl)-4-methyl-1,3-oxazol-2-yl]amino}-1,2,3,4-tetrahydronaphthalen-2-ol The title compound was prepared according to the procedure of Example 13E, substituting Example 16B for Example 13D. $^1$H NMR (300 MHz, DMSO-$d_6$) δ 9.06 (s, 1H), 7.62 (d, J=7.93 Hz, 2H), 7.41 (d, J=7.92 Hz, 2H), 7.10 (t, J=7.73 Hz, 1H), 6.84 (d, J=7.54 Hz, 1H), 4.80 (d, J=3.97 Hz, 1H), 3.91 (bs, 1H), 2.91 (m, 2H), 2.75 (m, 2H), 2.26 (s, 3H), 1.86 (bs, 1H), 1.61 (bs, 1H). MS (ESI) m/z 346 (M+H)$^+$.

Example 17

8-{[5-(3,4-dichlorophenyl)-4-methyl-1,3-oxazol-2-yl]amino}-1,2,3,4-tetrahydronaphthalen-2-ol

Example 17A 5-(3,4-dichlorophenyl)-4-methyl-1,3-oxazole

The title compound was prepared according to the procedure of Example 15A, substituting 3,4-dichlorobenzaldehyde for 4-formylbenzonitrile.

Example 17B 2-chloro-5-(3,4-dichlorophenyl)-4-methyl-1,3-oxazole

The title compound was prepared according to the procedure of Example 15B, substituting Example 17A for Example 15A.

Example 17C

8-{[5-(3,4-dichlorophenyl)-4-methyl-1,3-oxazol-2-yl]amino}-1,2,3,4-tetrahydronaphthalen-2-ol The title compound was prepared according to the procedure of Example 13E, substituting Example 17B for Example 13D. $^1$H NMR (300 MHz, CDCl$_3$) δ 7.71 (d, J=7.46 Hz, 1H), 7.56 (s, 1H), 7.46 (d, J=8.48 Hz, 1H), 7.29-7.33 (m, 1H), 7.18 (d, J=7.80 Hz, 1H), 6.93 (d, J=7.12 Hz, 1H), 4.25 (s, 1H), 3.00 (m, 2H), 2.86 (m, 1H), 2.62 (m, 1H), 2.39 (s, 3H), 2.06 (bs, 3H), 1.83 (bs, 1H). MS (ESI) m/z 388 (M+H)$^+$.

Example 18

8-{[5-(4-fluorophenyl)-4-methyl-1,3-oxazol-2-yl]amino}-1,2,3,4-tetrahydronaphthalen-2-ol

Example 18A 5-(4-fluorophenyl)-4-methyl-1,3-oxazole

The title compound was prepared according to the procedure of Example 15A, substituting 4-fluorobenzaldehyde for 4-formylbenzonitrile.

Example 18B 2-chloro-5-(4-fluorophenyl)-4-methyl-1,3-oxazole

The title compound was prepared according to the procedure of Example 15B, substituting Example 18A for Example 15A.

Example 18C

8-{[5-(4-fluorophenyl)-4-methyl-1,3-oxazol-2-yl]amino}-1,2,3,4-tetrahydronaphthalen-2-ol A mixture of Example 18B (500 mg, 2.36 mmol) and Example 1A (656 mg, 2.36 mmol) in n-butanol (12 mL) was heated to reflux for 1 hour. The reaction was cooled to room temperature, followed by addition of 12 mL 1M HCl and continued stirring for less than 1 hour. The mixture was diluted with water and ethyl acetate, and the organic phase was washed with water, dried, filtered, and evaporated. The crude product was triturated with CH$_2$Cl$_2$ (with sonication), and the solid was collected by filtration and washed with diethyl ether to give 192 mg (24% yield) of the title compound as a white solid. $^1$H NMR (300 MHz, DMSO-$d_6$) δ 8.98 (s, 1H), 7.53 (m, 3H), 7.28 (d, J=7.78 Hz, 2H), 7.09 (t, J=7.80 Hz, 1H), 6.83 (d, J=7.46 Hz, 1H), 4.79 (d, J=4.07 Hz, 1H), 3.92 (bs, 1H), 2.90 (m, 2H), 2.75 (m, 1H), 2.25 (s, 3H), 1.87 (bs, 1H), 1.61 (bs, 1H). MS (ESI) m/z 338 (M+H)$^+$.

Example 19

8-{[5-(4-chloro-2-methylphenyl)-4-methyl-1,3-oxazol-2-yl]amino}-1,2,3,4-tetrahydronaphthalen-2-ol

Example 19A 5-(4-chloro-2-methylphenyl)-4-methyl-1,3-oxazole

The title compound was prepared according to the procedure of Example 15A, substituting 4-chloro-2-methylbenzaldehyde for 4-formylbenzonitrile.

Example 19B 2-chloro-5-(4-chloro-2-methylphenyl)-4-methyl-1,3-oxazole

The title compound was prepared according to the procedure of Example 15B, substituting Example 19A for Example 15A.

Example 19C

8-{[5-(4-chloro-2-methylphenyl)-4-methyl-1,3-oxazol-2-yl]amino}-1,2,3,4-tetrahydronaphthalen-2-ol A mixture of Example 1A (516 mg, 1.86 mmol), Example 19B (450 mg, 1.86 mmol), and 1 drop aqueous concentrated HCl in n-butanol (9.3 mL) was heated to reflux for 2 hours. The reaction was cooled and concentrated, and the residue was partitioned between water and ethyl acetate. The organic phase was washed with water and brine, dried over $Na_2SO_4$, filtered and evaporated. The crude product was purified by chromatography on silica gel eluting first with 1% to 10% methanol $CH_2Cl_2$, then rechromatographed with 50% to 100% ethyl acetate:hexane to afford 225 mg (33% yield) of the title compound. $^1$H NMR (300 MHz, DMSO-$d_6$) δ 8.91 (s, 1H), 7.60 (d, J=7.80 Hz, 1H), 7.40 (s, 1H), 7.33 (s, 2H), 7.08 (t, J=7.80 Hz, 1H), 6.81 (d, J=6.78 Hz, 1H), 4.80 (d, J=4.07 Hz, 1H), 3.92 (bs, 1H), 2.89 (m, 2H), 2.74 (m, 1H), 2.32 (s, 3H), 2.04 (s, 3H), 1.86 (bs, 1H), 1.61 (bs, 1H). MS (ESI) m/z 368 (M+H)$^+$.

Example 20

8-{[5-(4-bromo-2-fluorophenyl)-4-methyl-1,3-oxazol-2-yl]amino}-1,2,3,4-tetrahydronaphthalen-2-ol

Example 20A

5-(4-bromo-2-fluorophenyl)-4-methyl-1,3-oxazole

The title compound was prepared according to the procedure of Example 15A, substituting 4-bromo-2-fluorobenzaldehyde for 4-formylbenzonitrile.

Example 20B

5-(4-bromo-2-fluorophenyl)-2-chloro-4-methyl-1,3-oxazole

The title compound was prepared according to the procedure of Example 15B, substituting Example 20A for Example 15A.

Example 20C

8-{[5-(4-bromo-2-fluorophenyl)-4-methyl-1,3-oxazol-2-yl]amino}-1,2,3,4-tetrahydronaphthalen-2-ol A mixture of Example 20B (200 mg, 0.688 mmol) and Example 1A (191 mg, 0.688 mmol) in n-butanol (10 mL) was heated to reflux. After 1.5 hours 1 drop aqueous concentrated HCl was added and the solution stirred an additional 1.5 hour. The reaction was cooled to room temperature, and two drops of 6M HCl were added and stirring was continued 15 minutes. The n-butanol was evaporated and the residue was partitioned between water and ethyl acetate. The organic layer was washed with water and brine, dried over $Na_2SO_4$, filtered, and evaporated. The crude product was triturated and sonicated ethyl acetate, and the resulting solid collected by filtration to give 52 mg (18% yield) of the title compound. $^1$H NMR (300 MHz, DMSO-$d_6$) δ 9.10 (s, 1H), 7.67 (d, J=10.31 Hz, 1H), 7.46 (m, 3H), 7.09 (t, J=7.93 Hz, 1H), 6.85 (d, J=7.54 Hz, 1H), 4.80 (d, J=3.97 Hz, 1H), 3.91 (bs, 1H), 2.89 (m, 2H), 2.75 (m, 1H), 2.11 (s, 3H), 1.87 (bs, 1H), 1.60 (bs, 1H). MS (ESI) m/z 416 (M+H)$^+$.

Example 21

(2R)-8-({4-methyl-5-[4-(trifluoromethyl)phenyl]-1,3-oxazol-2-yl}amino)-1,2,3,4-tetrahydronaphthalen-2-ol Method A Example 12C (3.3 g) was dissolved in ethanol (17 mg/mL after sonication), loaded on a Chiralpak AD-H (3 cm ID×25 cm) preparative chiral HPLC column (4.5 mL/injection), and eluted with 40% methanol in supercritical $CO_2$ (120 bar) under supercritical fluid chromatography (SFC) conditions at 40° C. with a flow rate of 40 gram/min. The early eluting peak was collected and the solvent evaporated to afford 1.46 g (44% yield) of the title compound as a pale gray solid. Analytical chiral HPLC (Chiralpak AD-H 4.6×25 mm, 30% ethanol in supercritical $CO_2$ (200 bar), 40° C., 3 mL/min) showed the isolated material to have 98.9% ee. $^1$H NMR (300 MHz, DMSO-$d_6$) δ 9.20 (s, 1H), 7.78 (m, 2H), 7.66 (m, 2H), 7.55 (m, 1H), 7.11 (t, 1H), 6.86 (m, 1H), 4.81 (d, 1H), 3.92 (m, 1H), 2.68-2.98 (m, 3H), 2.50 (m, 1H+DMSO), 2.33 (s, 3H), 1.87 (m, 1H), 1.61 (m, 1H). MS (ESI$^+$) m/z 389 (M+H)$^+$. Anal. Calcd for $C_{21}H_{19}F_3N_2O_2$: C, 64.94; H, 4.93; N, 7.21. Found: C, 64.70; H, 4.96; N, 7.17. $[α]_D$=+6.3° (c=0.6, methanol).

Method B

A solution of Example 24E (133 mg, 0.815 mmol) and Example 12B (213 mg, 0.815 mmol) in n-butanol (3 mL) was heated to 110° C. for 1 hour. The reaction mixture was cooled to ambient temperature, diluted with ethyl acetate, and quenched with aqueous saturated $NaHCO_3$ solution. The separated organic phase was washed with brine, dried ($Na_2SO_4$), filtered, and concentrated in vacuo to about 2 mL. Hexanes was added to precipitate the product, which was collected by vacuum filtration, washed with hexanes, and dried under vacuum at 50° C. for 3 hours to afford 162 mg (51% yield) of the title compound as a pale pink solid. $^1$H NMR (300 MHz, DMSO-$d_6$) δ 9.22 (s, 1H), 7.78 (m, 2H), 7.66 (m, 2H), 7.56 (m, 1H), 7.11 (t, 1H), 6.87 (m, 1H), 4.83 (d, 1H), 3.92 (m, 1H), 2.68-2.98 (m, 3H), 2.50 (m, 1H+DMSO), 2.33 (s, 3H), 1.87 (m, 1H), 1.61 (m, 1H). MS (ESI$^+$) m/z 389 (M+H)$^+$. $[α]_D$=+4.0° (c=1.2, methanol).

Method C

A mixture of Example 26F (71 mg, 0.18 mmol) and Example 12B (50 mg, 0.19 mmol) was heated to reflux in n-butanol (1 mL) for 2 hours, and cooled to room temperature. The solvent was evaporated in vacuo, and the residue was dissolved in 4 mL tetrahydrofuran and treated with hydrogen fluoride-triethylamine complex (1.0 mL). The reaction mixture was heated at 45° C. for 4 hours, after which time the reaction mixture was diluted with ethyl acetate, and washed with water and brine. The solvent was evaporated and the crude product chromatographed on silica gel (1 to 5% methanol-$CH_2Cl_2$) that afforded a solid, which was further purified by trituration with hexanes to give 33 mg (48% yield) of the title compound as an off-white solid. Analytical chiral HPLC (Chiralcel OJ 4.6×25 mm, 20% isopropanol/hexane, 23° C., 0.5 mL/min) showed the isolated material to have>98% ee. $^1$H NMR (300 MHz, DMSO-$d_6$) δ 9.19 (s, 1H), 7.77 (m, 2H), 7.66 (m, 2H), 7.55 (m, 1H), 7.11 (t, J=7.8 Hz, 1H), 6.86 (m, 1H), 4.80 (d, J=3.7 Hz, 1H), 3.92 (m, 1H), 2.68-2.98 (m, 3H), 2.50 (m, 1H+DMSO), 2.33 (s, 3H), 1.87 (m, 1H), 1.61 (m, 1H). MS (ESI$^+$) m/z 389 (M+H)$^+$.

Example 22

(2S)-8-({4-methyl-5-[4-(trifluoromethyl)phenyl]-1,3-oxazol-2-yl}amino)-1,2,3,4-tetrahydronaphthalen-2-ol Method A Example 12C (3.3 g) was dissolved in ethanol (17 mg/mL after sonication), loaded on a Chiralpak AD-H (3 cm ID×25 cm) preparative chiral HPLC column (4.5 mL/injection), and eluted with 40% methanol in supercritical $CO_2$ (120 bar) under supercritical fluid chromatography (SFC) conditions at 40° C. with a flow rate of 40 gram/min. The late eluting peak was collected and the solvent evaporated to afford 1.55 g (47% yield) of the title compound as a pale gray solid. Analytical chiral HPLC (Chiralpak AD-H 4.6×25 mm, 30% ethanol in supercritical $CO_2$ (200 bar), 40° C., 3 mL/min) showed the isolated material to have 98.9% ee. $^1$H NMR (300 MHz, DMSO-$d_6$) δ 9.19 (s, 1H), 7.77 (m, 2H), 7.66 (m, 2H), 7.55 (m, 1H), 7.11 (t, 1H), 6.86 (m, 1H), 4.80 (d, 1H), 3.92 (m, 1H), 2.68-2.98 (m, 3H), 2.33 (s, 3H), 2.50 (m, 1H+DMSO), 1.87 (m, 1H), 1.61 (m, 1H). MS (ESI$^+$) m/z 389 (M+H)$^+$. Anal. Calcd for $C_{21}H_{19}F_3N_2O_2$: C, 64.94; H, 4.93; N, 7.21. Found: C, 64.13; H, 4.91; N, 7.10. $[\alpha]_D$=−5.7° (c=0.8, methanol).

Method B

A solution of Example 25B (145 mg, 0.888 mmol) and Example 12B (232 mg, 0.888 mmol) in n-butanol (3 mL) was heated to 110° C. After 1.5 hours the reaction mixture was cooled, diluted with ethyl acetate, and washed with aq saturated $NaHCO_3$ and brine, dried over $Na_2SO_4$, and filtered. The solution was concentrated at reduced pressure to about 3-4 mL and then hexanes was added to precipitate the product, which was collected by vacuum filtration, washed with hexanes and air-dried to afford 209 mg (61% yield) of the title compound as a pale pink solid. Analytical chiral HPLC (Chiralcel OJ 4.6×25 mm, 20% isopropanol/hexane, 23° C., 0.5 mL/min) showed the isolated material to have>98% ee. $^1$H NMR (300 MHz, DMSO-$d_6$) δ 9.19 (s, 1H), 7.78 (m, 2H), 7.66 (m, 2H), 7.55 (m, 1H), 7.11 (t, J=7.8 Hz, 1H), 6.86 (m, 1H), 4.81 (d, J=3.7 Hz, 1H), 3.92 (m, 1H), 2.68-2.98 (m, 3H), 2.33 (s, 3H), 2.50 (m, 1H+DMSO), 1.87 (m, 1H), 1.61 (m, 1H). MS (ESI$^+$) m/z 389 (M+H)$^+$.

Example 23

8-({4-methyl-5-[6-(trifluoromethyl)pyridin-3-yl]-1,3-oxazol-2-yl}amino)-1,2,3,4-tetrahydronaphthalen-2-ol

Example 23A 5-(4-methyl-1,3-oxazol-5-yl)-2-(trifluoromethyl)pyridine 6-(trifluoromethyl)nicotinaldehyde (7 g, 40 mmol), 1-(1-isocyanoethylsulfonyl)-4-methylbenzene (8.41 g, 40.0 mmol) and $K_2CO_3$ (6.63 g, 48.0 mmol) were heated to reflux in methanol (200 mL) overnight. The solution was cooled and the solvents removed in vacuo. The orange semi-solid was partitioned between water and ethyl acetate. The organic phase was washed with water and brine, dried over $Na_2SO_4$, filtered, and the solvents removed in vacuo. The crude product was purified by column chromatography with 10% to 45% ethyl acetate/hexanes as eluent to afford 8.06 g (88% yield) of the title compound as a yellow solid. $^1$H NMR (300 MHz, CDCl$_3$): δ 9.01 (d, J=2.03 Hz, 1H), 8.08 (dd, J=7.97, 1.86 Hz, 1H), 7.93 (s, 1H), 7.77 (d, J=8.48 Hz, 1H), 2.51 (s, 3H,). MS (ESI$^+$) m/z 229 (M+H)$^+$.

Example 23B 5-(2-chloro-4-methyl-1,3-oxazol-5-yl)-2-(trifluoromethyl)pyridine Example 23A (8.05 g, 35.3 mmol) was dissolved in tetrahydrofuran (118 mL) and cooled to −78° C. Lithium bis(trimethylsilyl)amide (1 M in tetrahydrofuran, 38.8 mL, 38.8 mmol) was added dropwise, and the resulting solution stirred ½ hour at −78° C. Hexachloroethane (9.19 g, 38.8 mmol) was then added in one portion. The mixture was stirred overnight while warming to room temperature. The reaction mixture was diluted with water and extracted with ethyl acetate. The organic phase was washed with water, brine, dried over $Na_2SO_4$, filtered, and the solvents removed in vacuo. The resulting solid was chromatographed on a $SiO_2$ column using two column volumes of hexane, followed by 10%-40% ethyl acetate/hexanes to afford 7.89 g (85% yield) of the title compound as a yellow solid. $^1$H NMR (300 MHz, CDCl$_3$): δ 8.95 (d, J=2.03 Hz, 1H) 8.03 (dd, J=8.14, 1.70 Hz, 1H), 7.77 (d, J=7.46 Hz, 1H,), 2.47 (s, 3H,). MS (DCI) m/z 263 (M+H)$^+$.

Example 23C 8-({4-methyl-5-[6-(trifluoromethyl)pyridin-3-yl]-1,3-oxazol-2-yl}amino)-1,2,3,4-tetrahydronaphthalen-2-ol A solution of Example 1A (506 mg, 1.82 mmol) and Example 23B (479 mg, 1.82 mmol) in n-butanol (18 mL) was heated to 110° C. for 1.5 hour. The reaction mixture was cooled to ambient temperature, aqueous 1 M HCl (6 mL) was added, and stirring was continued 1 hour. The reaction was then diluted with water, basified with saturated aq $NaHCO_3$ solution, and the product was extracted with ethyl acetate. The organic phase was washed with water, brine, dried over $Na_2SO_4$, and evaporated. The crude product was chromatographed on silica gel eluting with 2% to 30% methanol/$CH_2Cl_2$ to give a pale purple solid that was triturated with 1:1 diethyl ether:hexanes. The resulting solid was filtered and air dried. 100 mg of this material was further purified by preparative HPLC on a Waters Sunfire C18 5 μM 30 mm×70 mm column. Samples were injected in 2.5 mL DMSO:methanol (1:1). A gradient of acetonitrile (A) and 0.1% trifluoroacetic acid in $H_2O$(B) was used at a flow rate of 50 mL/min (0-0.5 min 10% A, 0.5-12 min linear gradient 10%-95% A, 12-15 min 95% A, 15-17 min linear gradient 95-10% A) to afford 73 mg of the title compound as a tan solid. $^1$H NMR (300 MHz, DMSO-$d_6$) δ: 9.34 (s, 1H), 8.86 (d, J=2.03 Hz, 1H), 8.01-8.06 (m, 1H), 7.90-7.94 (m, 1H), 7.53 (d, J=7.80 Hz, 1H) 7.12 (t, J=7.80 Hz, 1H), 6.88 (d, J=7.80 Hz, 1H), 3.91 (m, 1H), 2.96 (m, 1H), 2.86 (m, 1H), 2.69-2.80 (m, 1H) 2.35 (s, 3H), 1.85-1.91 (m, 1H), 1.55-1.68 (m, 1H). MS (ESI$^+$) m/z 390 (M+H)$^+$.

Example 24

(2R)-8-amino-1,2,3,4-tetrahydronaphthalen-2-ol

Example 24A 8-amino-1,2,3,4-tetrahydronaphthalen-2-ol

Ethanol (1 liter) was added to 8-amino-2-naphthol (100 g, 0.61 mol), Raney nickel (40 g water wet), and sodium hydroxide (4.0 g 8 mol % aqueous) in a stirred reactor. The reactor was sealed and sparged with hydrogen. The reaction mixture was stirred for 13 hours at 85° C. and then an additional 8 hours at 100° C. The mixture was then filtered through a pad of Celite. The resulting solution was treated with Darco G-60 (35 grams) and heated to reflux for 1 hour, then cooled to ambient temperature and stirred an additional 3 hours. This mixture was filtered through Celite (350 grams), and the pad washed with ethyl acetate (1.5 liters). The solvent was removed in vacuo and methyl tert-butyl ether (1 liter) was added. This was heated for 15 minutes at 50° C., stirred for one hour at ambient temperature, filtered, and the solvent removed in vacuo. Approximately half of the resulting crude solid was purified by chromatography on silica gel using 2% to 30% methanol/methylene chloride as eluent, which gave 37 g of the title compound as a light brown solid. $^1$H NMR (300 MHz, CDCl$_3$) δ 6.96 (t, J=7.63 Hz, 1H), 6.55 (dd, J=10.68, 7.63 Hz, 2H), 4.14-4.24 (m, 1H), 2.80-2.95 (m, 3H), 2.38 (dd, J=16.11, 7.63 Hz, 1H), 1.96-2.09 (m, 1H), 1.70-1.85 (m, 1H).

Example 24B

Benzyl 7-hydroxy-5,6,7,8-tetrahydronaphthalen-1-ylcarbamate

A solution of benzyl chloroformate (5.84 mL, 41.1 mmol) in 5 mL CH$_2$Cl$_2$ was added dropwise via addition funnel to Example 24A (3.05 g, 18.7 mmol) and Hunig's base (8.14 mL, 46.7 mmol) in dichloromethane (55 mL) at ambient temperature. After 18 hr IN (aq) NaOH solution (50 mL) was added and the reaction was stirred vigorously for 15 min. The separated organic layer was washed with brine, dried (Na$_2$SO$_4$), filtered, and concentrated in vacuo. The crude product was triturated with diethyl ether and the solid collected by suction filtration. The result was 3.37 g (61% yield) of the title compound as a brown solid. $^1$H NMR (300 MHz, DMSO-d$_6$) δ 8.82 (s, 1H), 7.30-7.45 (m, 5H), 7.14 (m, 1H), 7.05 (t, 1H), 6.90 (m, 1H), 5.12, (s, 2H), 4.77 (d, 1H), 3.87 (m, 1H), 2.86 (m, 2H), 2.71 (m, 1H), 2.43 (m, 1H), 1.84 (m, 1H), 1.58 (m, 1H). MS (APCI$^+$) m/z 298 (M+H)$^+$.

Example 24C

8-{[(benzyloxy)carbonyl]amino}-1,2,3,4-tetrahydronaphthalen-2-yl (2R)-methoxy(phenyl)acetate A mixture of Example 24B (1.03 g, 3.46 mmol), (R)-2-methoxy-2-phenylacetic acid (0.633 g, 3.81 mmol), 1,3-dicyclohexylcarbodiimide (1.14 g, 5.54 mmol), and 4-dimethylaminopyridine (0.846 g, 6.93 mmol) in dichloromethane (35 mL) was stirred at ambient temperature for 18 hr. The reaction mixture was diluted with CH$_2$Cl$_2$ and washed with saturated aqueous NH$_4$Cl solution, brine, dried (Na$_2$SO$_4$), filtered, and concentrated in vacuo. The crude product was placed on a silica gel column and eluted with 30% ethyl acetate/hexanes to afford 1.38 g (89% yield) of the title compound as a colorless syrup. MS (ESI$^+$) m/z 446 (M+H)$^+$, 463 (M+NH$_4$).

Example 24D (2R)-8-amino-1,2,3,4-tetrahydronaphthalen-2-yl (2R)-methoxy(phenyl)acetate Ethanol (20 mL) was added to a hydrogenation reaction vessel containing Example 24C (1.30 g, 2.92 mmol) and 0.2 g of 20% Pd(OH)$_2$/C. The reactor was sealed under 25 psi H$_2$, and the reaction was allowed to proceed at ambient temperature for 25 min. The catalyst was filtered and washed well with ethanol. The filtrate was concentrated in vacuo, and the residue (0.76 g) was loaded on a silica gel column and eluted (Analogix Intelliflash 280; 20% to 40% ethyl acetate/hexanes eluant, 0-35 min, 37 mL/min; SF25-60 g column). The fractions that eluted from approximately 19-24 min were combined, and concentrated to afford 0.315 g (35% yield) of the title compound as a thick, pale brown oil. $^1$H NMR (300 MHz, DMSO-d$_6$) δ 7.37 (m, 5H), 6.80 (t, 1H), 6.43 (m, 1H), 6.31 (m, 1H), 5.17, (m, 1H), 4.90 (s, 1H), 4.73 (bs, 2H), 3.32 (s, 3H), 2.70 (m, 3H), 2.31 (m, 1H), 1.85 (m, 2H). MS (DCI$^+$) m/z 312 (M+H)$^+$.

Example 24E (2R)-8-amino-1,2,3,4-tetrahydronaphthalen-2-ol

Method A

A mixture of Example 24D (3.05 g, 9.80 mmol) in tetrahydrofuran (40 mL) and lithium hydroxide (1 M aq, 30 mL, 30.0 mmol) was stirred vigorously at ambient temperature. After 1.5 hours the reaction mixture was partitioned between 100 mL ethyl acetate:H$_2$O (1:1). The separated organic phase was washed with aq saturated NaHCO$_3$ and brine, dried over Na$_2$SO$_4$, and filtered. The solvent was removed at the rotary evaporator to yield 1.31 g (82% yield) of the title compound as a tan solid. $^1$H NMR (300 MHz, DMSO-d$_6$) δ 6.76 (t, 1H), 6.41 (d, 1H), 6.28 (d, 1H), 4.74, (d, 1H), 4.65 (bs, 2H), 3.90 (m, 1H), 2.52-2.79 (m, 3H), 2.16 (m, 1H), 1.83 (m, 1H), 1.55 (m, 1H). MS (DCI$^+$) m/z 164 (M+H)$^+$, 181 (M+NH$_4$)+.

Method B

Example 24A was dissolved in ethanol, loaded on a Chiralpak AD-H (4.6 mm ID×250 mm) chiral HPLC column (0.1 mL/injection), and eluted with 12% ethanol+1% isopropylamine in supercritical CO$_2$ (200 bar) under supercritical fluid chromatography (SFC) conditions at 40° C. with a flow rate of 3 mL/min. The earlier eluting peak was collected and the solvent evaporated to afford the title compound as an off-white solid in >99% ee.

Example 25

(2S)-8-amino-1,2,3,4-tetrahydronaphthalen-2-ol

Example 25A (2S)-8-amino-1,2,3,4-tetrahydronaphthalen-2-yl (2R)-methoxy(phenyl)acetate Ethanol (20 mL) was added to a hydrogenation reaction vessel containing Example 24C (1.30 g, 2.92 mmol) and 0.2 g of 20% Pd(OH)$_2$/C. The reactor was sealed under 25 psi H$_2$, and the reaction was allowed to proceed at ambient temperature for 25 min. The catalyst was filtered and washed well with EtOH. The filtrate was concentrated in vacuo, and the residue (0.76 g) was loaded on a silica gel column and eluted (Analogix Intelliflash 280; 20% to 40% ethyl acetate/hexanes eluant, 0-35 min, 37 mL/min; SF25-60 g column). The fractions that eluted from approximately 25-31 min were combined to afford 0.308 g (34% yield) of the title compound as a thick, pale brown oil. $^1$H NMR (300 MHz, DMSO-d$_6$) δ 7.37 (m, 5H), 6.79 (t, 1H), 6.44 (m, 1H), 6.26 (m, 1H), 5.20, (m, 1H), 4.89 (s, 1H), 4.77 (bs, 2H), 3.32 (s, 3H), 2.78 (m, 1H), 2.35-2.5 (m, 3H), 1.71 (m, 2H). MS (DCI$^+$) m/z 312 (M+H)$^+$.

Example 25B

(2S)-8-amino-1,2,3,4-tetrahydronaphthalen-2-ol

Method A

A mixture of Example 25A (300 mg, 0.963 mmol) in tetrahydrofuran (4 mL) and aqueous lithium hydroxide (1 M aq, 3 mL, 3.00 mmol) was stirred at ambient temperature for 1.5 hour. The reaction was diluted with ethyl acetate and poured into aqueous saturated NaHCO$_3$ solution. The separated organic phase was washed with brine, dried over Na$_2$SO$_4$, and concentrated in vacuo. The result was 145 mg (92% yield) of the title compound as a tan solid. $^1$H NMR (300 MHz, DMSO-d$_6$) δ 6.76 (t, 1H), 6.41 (d, 1H), 6.28 (d, 1H), 4.74, (d, 1H), 4.66 (bs, 2H), 3.90 (m, 1H), 2.52-2.79 (m, 3H), 2.17 (m, 1H), 1.83 (m, 1H), 1.55 (m, 1H). MS (DCI$^+$) m/z 164 (M+H)$^+$, 181 (M+NH$_4$)+.

Method B

Example 24A was dissolved in ethanol, loaded on a Chiralpak AD-H (4.6 mm ID×250 mm) chiral HPLC column (0.1 mL/injection), and eluted with 12% ethanol+1% isopropylamine in supercritical CO$_2$ (200 bar) under supercritical fluid chromatography (SFC) conditions at 40° C. with a flow rate of 3 mL/min. The later eluting peak was collected and the solvent evaporated to afford the title compound as an off-white solid in >99% ee.

Example 26

7-{[tert-butyl(diphenyl)silyl]oxy}-5,6,7,8-tetrahydronaphthalen-1-amine

Example 26A

(2R)-8-methoxy-1,2,3,4-tetrahydronaphthalen-2-ol

N-((1R,2R)-2-amino-1,2-diphenylethyl)-4-methylbenzenesulfonamide (0.333 g, 0.908 mmol) and benzene ruthenium(II) chloride dimer (0.113 g, 0.226 mmol) in 80 mL isopropanol were stirred at 80° C. for 30 minutes, then cooled to room temperature. A solution of 8-methoxy-2-tetralone (4.0 g, 23 mmol) in isopropanol (400 mL) was added, followed by potassium hydroxide (0.038M in isopropanol, 120 mL, 4.56 mmol). The reaction mixture was stirred at 50° C. for 1.5 hours, at which time the starting material had been consumed. The isopropanol was evaporated, the residue was taken up in ethyl acetate and washed with water and brine. The organic layer was dried over Na$_2$SO$_4$, filtered, and concentrated. The residue was chromatographed on silica gel (15 to 30% ethyl acetate-hexane, eluant) to afford 3.0 g (74% yield) of the title compound as a fluffy off-white solid. Analytical chiral HPLC (Chiralcel OJ 4.6×25 mm, 20% isopropanol/hexane, 23° C., 0.5 mL/min) showed the isolated material to be >98% ee. $^1$H NMR (300 MHz, DMSO-d$_6$) δ 7.04 (t, J=7.8 Hz, 1H), 6.68 (m, 2H), 4.72 (d, J=3.7 Hz, 1H), 3.87 (m, 1H), 3.74 (s, 3H), 2.57-2.91 (m, 3H), 2.33 (m, 1H), 1.81 (m, 1H), 1.59 (m, 1H). MS (DCI$^+$) m/z 196 (M+NH$_4$)+.

Example 26B tert-butyl {[(2R)-8-methoxy-1,2,3,4-tetrahydronaphthalen-2-yl]oxy}diphenylsilane Example 26A (3 g, 16.8 mmol), tert-butylchlorodiphenylsilane (4.4 mL, 17 mmol), and imidazole (3.44 g, 50.5 mmol) were stirred overnight in CH$_2$Cl$_2$ (70 mL) at room temperature. The mixture was diluted with more CH$_2$Cl$_2$ and washed with water and brine. The organic phase was dried (Na$_2$SO$_4$), evaporated, and the residue chromatographed on silica gel (1 to 5% ethyl acetate-hexane, eluant) to afford 6.40 g (91% yield) of the title compound as a colorless oil. $^1$H NMR (300 MHz, DMSO-d$_6$) δ 7.60 (m, 4H), 7.41 (m, 6H), 7.04 (t, J=8.0 Hz, 1H), 6.67 (m, 2H), 4.14 (m, 1H), 3.70 (s, 3H), 2.68-2.91 (m, 2H), 2.52-2.61 (m, 2H), 1.72 (m, 2H), 0.99 (s, 9H). MS (DCI$^+$) m/z 434 (M+NH$_4$)+.

Example 26C

(7R)-7-{[tert-butyl(diphenyl)silyl]oxy}-5,6,7,8-tetrahydronaphthalen-1-ol

A solution of Example 26B (0.9 g, 2.2 mmol) in N-methylmorpholine (7 mL) was treated with potassium carbonate (0.3 g, 2.2 mmol) and thiophenol (0.23 mL, 2.24 mmol), and the mixture was heated to reflux for 2 hours. The reaction mixture was cooled to room temperature and then diluted with ethyl acetate and water. The aqueous layer was extracted three times with ethyl acetate, and the combined organic extract was washed three times with water and once with brine, dried over Na$_2$SO$_4$, filtered and concentrated. The residue was chromatographed on silica gel (5 to 20% ethyl acetate-hexane, eluant) to afford 0.45 g (52% yield) of the title compound as a colorless oil. $^1$H NMR (300 MHz, DMSO-d$_6$) δ 9.11 (br, 1H), 7.64 (m, 4H), 7.41 (m, 6H), 6.85 (t, J=7.6 Hz, 1H), 6.45-6.56 (m, 2H), 4.06 (m, 1H), 2.70-2.86 (m, 2H), 2.45-2.54 (m, 2H), 1.73 (m, 2H), 0.97 (s, 9H). MS (DCI$^+$) m/z 403 (M+H)$^+$, 420 (M+NH$_4$)+.

Example 26D

(7R)-7-{[tert-butyl(diphenyl)silyl]oxy}-5,6,7,8-tetrahydronaphthalen-1-yl trifluoroacetate A solution of Example 26C (190 mg, 0.472 mmol) in dichloromethane (3 mL) was treated with triethylamine (0.48 mL, 3.44 mmol) and a small amount of 4-(dimethylamino)pyridine, and cooled to −10° C. At this temperature, trifluoroacetic anhydride (0.14 mL, 0.83 mmol) was slowly added, and the reaction was stirred at −10° C. for 1 hour, and at room temperature for 2 hours. The mixture was poured into ice and treated with conc. NH$_4$OH (about 1 mL), and the organic layer was separated and washed with water, dried (Na$_2$SO$_4$), filtered and concentrated. The crude product was chromatographed on silica gel (1 to 5% ethyl acetate-hexane, eluant) to afford 143 mg (57% yield) of the title compound as a pale yellow oil. $^1$H NMR (300 MHz, DMSO-d$_6$) δ 7.07-7.62 (m, 13H), 4.22 (m, 1H), 2.59-2.84 (m, 4H), 1.72-1.90 (m, 2H), 0.97 (s, 9H). MS (DCI$^+$) m/z 552 (M+NH$_4$)+.

Example 26E

N-((7R)-7-{[tert-butyl(diphenyl)silyl]oxy}-5,6,7,8-tetrahydronaphthalen-1-yl)-N-(diphenylmethylene)amine A mixture of Example 26D (291 mg, 0.544 mmol), benzophenone imine (0.18 mL, 1.1 mmol), cesium carbonate (390 mg, 1.20 mmol), tris(dibenzylideneacetone)dipalladium(0) (14 mg, 0.015 mmol), and 2,2'-bis(diphenylphosphino)-1,1'-binaphthyl (22 mg, 0.035 mmol) in dimethoxyethane (2.2 mL) was heated at 150° C. for 25 minutes in a microwave reactor. The mixture was cooled to room temperature, and the solution was pipetted away from the residual solid and concentrated. Chromatography of the resulting residue on silica gel (1 to 5% ethyl acetate-hexane, eluant) afforded 263 mg (85% yield) of the title compound as a sticky yellow oil/foam. $^1$H NMR (300 MHz, DMSO-$d_6$) δ 7.19-7.74 (m, 18H), 6.92 (m, 2H), 6.77 (m, 1H), 6.60 (m, 1H), 6.18 (m, 1H), 4.12 (m, 1H), 2.53-2.62 (m, 3H), 2.38 (m, 1H), 1.84 (m, 1H), 1.72 (m, 1H), 0.99 (s, 9H). MS (DCI$^+$) m/z 566 (M+H)+.

Example 26F (7R)-{[tert-butyl(diphenyl)silyl]oxy}-5,6,7,8-tetrahydronaphthalen-1-amine A solution of Example 26E (105 mg, 0.186 mmol) in tetrahydrofuran (5.3 mL) was treated with aqueous hydrochloric acid (2M, 0.21 mL, 0.42 mmol), and the reaction stirred at room temperature for 10 minutes before being quenched with saturated NaHCO$_3$ solution. Extraction with ethyl acetate, followed by drying with Na$_2$SO$_4$, filtered, and concentrated. The crude residue was chromatographed on silica gel (3 to 10% ethyl acetate-hexane, eluant) to afford 53 mg (71% yield) of the title compound as a colorless oil. $^1$H NMR (300 MHz, DMSO-$d_6$) δ 7.64 (m, 4H), 7.42 (m, 6H), 6.73 (m, 1H), 6.40 (d, J=7.5 Hz, 1H), 6.24 (d, J=7.1 Hz, 1H), 4.64 (br, 2H), 4.07 (m, 1H), 2.55-2.79 (m, 3H), 2.26 (m, 1H), 1.57-1.76 (m, 2H), 1.02 (s, 9H). MS (DCI$^+$) m/z 402 (M+H)$^+$.

Example 27

(2R)-8-({5-[2-fluoro-4-(trifluoromethyl)phenyl]-4-methyl-1,3-oxazol-2-yl}amino)-1,2,3,4-tetrahydronaphthalen-2-ol Example 27A 5-(2-fluoro-4-(trifluoromethyl)phenyl)-4-methyl-1,3-oxazole The title compound was prepared according to the procedure of Example 12A, substituting 2-fluoro-4-(trifluoromethyl)benzaldehyde for 4-(trifluoromethyl)benzaldehyde.

Example 27B 2-chloro-5-(2-fluoro-4-(trifluoromethyl)phenyl)-4-methyl-1,3-oxazole The title compound was prepared according to the procedure of Example 12B, substituting Example 27A for Example 12A.

Example 27C (2R)-8-({5-[2-fluoro-4-(trifluoromethyl)phenyl]-4-methyl-1,3-oxazol-2-yl}amino)-1,2,3,4-tetrahydronaphthalen-2-ol Example 27B (6.34 g, 22.7 mmol) and Example 24E (3.7 g, 23 mmol) were dissolved in n-butanol (227 mL) and heated at 110° C. for 4 hours. Two drops aqueous concentrated HCl were added and heating was continued 2 hours additional, after which the solvent was evaporated in vacuo. The resulting solid was chromatographed (SiO$_2$, 5% to 40% methanol/methylene chloride as eluent) to give a solid that was triturated with hexanes:ethyl ether (1:1), collected by filtration and air-dried to afford 5.00 g (54% yield) of the title compound as a gray solid. $^1$H NMR (300 MHz, CD$_3$OD) δ: 7.69 (t, J=7.73 Hz, 1H), 7.51-7.57 (m, 2H), 7.38 (d, J=7.93 Hz, 1H), 7.14 (t, J=7.73 Hz, 1H), 6.96 (d, J=7.54 Hz, 1H), 4.02-4.11 (m, 1H), 2.94-3.09 (m, 2H), 2.79-2.90 (m, 1H), 2.60 (dd, J=16.46, 7.73 Hz, 1H), 2.17-2.20 (m, 3H), 1.98-2.08 (m, 1H), 1.69-1.82 (m, 1H,). MS (ESI$^+$) m/z 407 (M+H)$^+$.

Example 28

(2S)-8-({5-[2-fluoro-4-(trifluoromethyl)phenyl]-4-methyl-1,3-oxazol-2-yl}amino)-1,2,3,4-tetrahydronaphthalen-2-ol Example 27B (3.67 g, 13.1 mmol) and Example 25B (2.14 g, 13.1 mmol) were dissolved in n-butanol (227 mL), followed by addition of 2 drops aqueous concentrated HCl. The reaction was heated at 110° C. for 2 hours, after which the solvent was evaporated in vacuo. The resulting solid was chromatographed (SiO$_2$, 5% to 40% methanol:methylene chloride as eluent) to give a solid that was triturated with hexanes:ethyl ether (1:1), and filtered and air-dried to afford 2.84 g (53% yield) of the title compound as a gray solid. $^1$H NMR (300 MHz, CD$_3$OD) δ: 7.69 (t, J=7.73 Hz, 1H), 7.51-7.57 (m, 2H), 7.38 (d, J=7.93 Hz, 1H), 7.14 (t, J=7.73 Hz, 1H), 6.96 (d, J=7.54 Hz, 1H), 4.02-4.11 (m, 1H), 2.94-3.09 (m, 2H), 2.79-2.90 (m, 1H), 2.60 (dd, J=16.46, 7.73 Hz, 1H), 2.17-2.20 (m, 3H), 1.98-2.08 (m, 1H), 1.69-1.82 (m, 1H,). MS (ESI$^+$) m/z 407 (M+H)$^+$.

Example 29

8-{[5-(4-bromo-3-fluorophenyl)-4-methyl-1,3-oxazol-2-yl]amino}-1,2,3,4-tetrahydronaphthalen-2-ol Example 29A 5-(4-bromo-3-fluorophenyl)-4-methyloxazole A mixture of 4-bromo-3-fluorobenzaldehyde (1.02 g, 5.0 mmol), 1-(1-isocyanoethylsulfonyl)-4-methylbenzene (1.05 g, 5.0 mmol), and K$_2$CO$_3$ (0.83 g, 6.0 mmol) in methanol (20 mL) was heated to reflux. After 2.5 hr the mixture was cooled to ambient temperature and the volatiles evaporated. The residue was partitioned between Et$_2$O and H$_2$O. The separated aqueous phase was extracted with Et$_2$O, and the combined organic extract was washed with brine, dried (Na$_2$SO$_4$), filtered, and concentrated in vacuo. Flash chromatography (Analogix® Intelliflash 280™; 10% to 20% EtOAc/hexanes eluant; SF25-80 g column) yielded 1.04 g (81%) of the title compound as a white solid. $^1$H NMR (300 MHz, DMSO-$d_6$) δ 8.41 (s, 1H), 7.83 (dd, J=8.3, 7.5 1H), 7.57 (dd, J=10.1, 2.0 1H), 7.42 (dd, J=8.5, 2.0 1H), 2.38 (s, 3H). MS (DCI$^+$) m/z 256/258 (M+H).

Example 29B 5-(4-bromo-3-fluorophenyl)-2-chloro-4-methyloxazole

LiHMDS (1 M in THF, 4.4 mL, 4.4 mmol) was added dropwise via syringe to a solution of Example 29A (1.03 g, 4.02 mmol) in THF (20 mL) at −78° C. After 30 min solid hexachloroethane (1.90 g, 8.04 mmol) was added in one portion and the reaction mixture was allowed to gradually warm to ambient temperature over 16 hr. The reaction was diluted with Et$_2$O and quenched with half-saturated aqueous NH$_4$Cl solution. The separated aqueous phase was extracted with Et$_2$O, and the combined organic layer was washed with brine, dried (Na$_2$SO$_4$), filtered, and concentrated in vacuo.

Flash chromatography (Analogix® Intelliflash 280™; 0% to 15% EtOAc/hexanes eluant; SF25-120 g column) afforded 1.07 g (92%) of the title compound as a white solid. $^1$H NMR (300 MHz, DMSO-$d_6$) δ 7.84 (dd, J=8.4, 7.4 1H), 7.57 (dd, J=9.9, 2.0 1H), 7.39 (dd, J=8.5, 2.0 1H), 2.36 (s, 3H). MS (DCI$^+$) m/z 290/292 (M+H).

Example 29C 8-(5-(4-bromo-3-fluorophenyl)-4-methyloxazol-2-ylamino)-1,2,3,4-tetrahydronaphthalen-2-ol A solution of Example 1A (191 mg, 0.688 mmol) and Example 29B (220 mg, 0.757 mmol) in BuOH (3 mL) was heated at 120° C. for 1 hr. The reaction was cooled to ambient temperature, diluted with EtOAc, washed with aqueous saturated NaHCO$_3$ solution and brine, dried over Na$_2$SO$_4$, and filtered. The solution was concentrated to approximately 5 mL, followed by addition of hexanes. The resulting precipitate was collected by filtration, washed with EtOAc, CH$_2$Cl$_2$ and Et$_2$O, and air-dried. The result was 176 mg (61%) of the title compound as a light grey solid. $^1$H NMR (300 MHz, DMSO-$d_6$) δ 9.14 (s, 1H), 7.75 (dd, J=8.4, 7.6 1H), 7.55 (d, J=7.2, 1H), 7.35 (dd, J=10.4, 2.0 1H), 7.25 (dd, J=8.4, 2.0 1H), 7.10 (t, J=7.8, 1H), 6.85 (d, J=7.4, 1H), 4.81 (d, J=3.9, 1H), 3.99-3.84 (m, 1H), 2.99-2.81 (m, 2H), 2.79-2.66 (m, 1H), 2.55-2.42 (m, 1H), 2.28 (s, 3H), 1.85 (m, 1H), 1.61 (m, 1H). MS (ESI$^+$) m/z 417/419 (M+H).

Example 30

8-{[5-(3-fluoro-4-methylphenyl)-4-methyl-1,3-oxazol-2-yl]amino}-1,2,3,4-tetrahydronaphthalen-2-ol Example 30A 5-(3-fluoro-4-methylphenyl)-4-methyloxazole A mixture of 3-fluoro-4-methylbenzaldehyde (1.38 g, 10.0 mmol), 1-(1-isocyanoethylsulfonyl)-4-methylbenzene (2.09 g, 10.0 mmol), and K$_2$CO$_3$ (1.66 g, 12.0 mmol) in 50 mL methanol was heated at reflux 3 hr, then cooled to room temperature and stirred overnight. The reaction mixture was concentrated and the residue taken up in 25 mL H$_2$O and 25 mL Et$_2$O. The water layer was extracted with Et$_2$O, and the organic layers were combined, washed with brine, dried over MgSO$_4$, filtered, and concentrated in vacuo. The residue was chromatographed on silica gel (Analogix® SF40-115 g column) with 15% EtOAc/hexanes to yield 1.56 g (82%) of the title compound. $^1$H NMR (300 MHz, DMSO-$d_6$) δ 8.34 (s, 1H), 7.45-7.30 (m, 3H), 2.36 (s, 3H), 2.27 (d, J=1.9, 3H).

Example 30B 2-chloro-5-(3-fluoro-4-methylphenyl)-4-methyloxazole

A solution of Example 30A (1.56 g, 8.16 mmol) in THF (36 mL) was cooled to −78° C., followed by dropwise addition of LiHMDS (1 M in THF, 10.2 mL, 10.2 mmol). The reaction was stirred 30 min and then hexachloroethane (3.86 g, 16.3 mmol) was added in one portion. The reaction was allowed to slowly warm to room temperature and stir over the weekend. The reaction was then quenched with 50 mL of 1:1 water: saturated aqueous NH$_4$Cl solution, and extracted with Et$_2$O (2×). The combined organic layer was dried with MgSO$_4$, filtered, and concentrated in vacuo. The residue was chromatographed on silica gel (Analogix® SF40-80 g column) eluting with 7% EtOAc/hexanes to yield 1.71 g (93%) of the title compound. $^1$H NMR (300 MHz, DMSO-$d_6$) δ 7.43 (dd, J=11.9, 4.4 1H), 7.35-7.29 (m, 2H), 2.34 (s, 3H), 2.27 (d, J=1.9, 3H). MS (DCI$^+$) m/z 226 (M+H).

Example 30C 8-(5-(3-fluoro-4-methylphenyl)-4-methyloxazol-2-ylamino)-1,2,3,4-tetrahydronaphthalen-2-ol A mixture of Example 1A (400 mg, 1.44 mmol) and Example 30B (325 mg, 1.44 mmol) in BuOH (14 mL) was heated at 110° C. for 2 hr, 10 min. The reaction was cooled to ambient temperature, followed by addition of 10 mL 1M HCl. The mixture was stirred approximately 0.5 hour. Water was added, the layers were separated, and the organic mixture was diluted with EtOAc. The separated organic layer was washed with saturated NaHCO$_3$ solution, water and brine, dried over Na$_2$SO$_4$, filtered, and concentrated in vacuo. The crude product was triturated with Et$_2$O, and the resulting solid was collected by filtration to yield 224 mg (44%) of the title compound as an off-white solid. $^1$H NMR (300 MHz, DMSO-$d_6$) δ 9.01 (s, 1H), 7.58 (d, J=7.3, 1H), 7.34 (t, J=8.1, 1H), 7.24-7.13 (m, 2H), 7.09 (t, J=7.8, 1H), 6.84 (d, J=7.5, 1H), 4.80 (d, J=4.0, 1H), 3.98-3.86 (m, 1H), 2.99-2.80 (m, 2H), 2.80-2.65 (m, 1H), 2.55-2.42 (m, 1H), 2.26 (s, 3H), 2.24 (d, J=1.4, 3H), 1.93-1.80 (m, 1H), 1.68-1.52 (m, 1H). MS (ESI$^+$) m/z 353 (M+H).

Example 31

8-({4-methyl-5-[5-(trifluoromethyl)-2-furyl]-1,3-oxazol-2-yl}amino)-1,2,3,4-tetrahydronaphthalen-2-ol Example 31A 4-methyl-5-(5-(trifluoromethyl)furan-2-yl)oxazole A mixture of 1-(1-isocyanoethylsulfonyl)-4-methylbenzene (0.893 g, 4.27 mmol), 5-(trifluoromethyl)furan-2-carbaldehyde (0.70 g, 4.3 mmol), and K$_2$CO$_3$ (1.18 g, 8.53 mmol) in MeOH (25 mL) was heated to reflux. After 2.5 hr the reaction mixture was cooled to ambient temperature and stirred overnight. The reaction mixture was extracted with EtOAc (2×200 mL) and washed with water (2×200 mL), then washed with brine and dried over Na$_2$SO$_4$, filtered, and concentrated to an orange solid. The crude product was chromatographed on silica gel (Analogix® SF25-40G column, 0%-25% EtOAc/hexanes, 30 mL/min) to yield 709 mg (77%) of the title compound as a light yellow solid. $^1$H NMR (300 MHz, MeOH-$d_4$) δ 8.19 (s, 1H), 7.12 (m, 1H), 6.80 (dd, J=3.7, 0.6 1H), 2.41 (s, 3H). MS (DCI$^+$) m/z 218 (M+H).

Example 31B 2-chloro-4-methyl-5-(5-(trifluoromethyl)furan-2-yl)oxazole

To a solution of Example 31A (0.62 g, 2.8 mmol) in THF (20 mL) at −78° C. was added LiHMDS (1 M in THF, 3.4 mL, 3.4 mmol) dropwise over a period of 6-8 min. After 30 min hexachloroethane (1.35 g, 5.68 mmol) was added at once as a solid and the mixture was left to stir overnight warming to ambient temperature. The mixture was diluted with Et$_2$O and washed with aqueous NH$_4$Cl solution and water. The organic layer was separated and concentrated in vacuo, and the residue chromatographed on silica gel with EtOAc/hexanes (0%-20%) to yield 0.6 g (84%) of the title compound as a white solid. $^1$H NMR (300 MHz, DMSO-$d_6$) δ 7.46 (m, 1H), 7.04 (d, J=3.4, 1H), 2.33 (s, 3H).

Example 31C 8-(4-methyl-5-(5-(trifluoromethyl)furan-2-yl)oxazol-2-ylamino)-1,2,3,4-tetrahydronaphthalen-2-ol A mixture of Example 31B (200 mg, 0.795 mmol) and Example 1A (221 mg, 0.795 mmol) in BuOH (5 mL) was heated at reflux for 2 h. The reaction was cooled to room temperature, diluted with EtOAc, and washed 3× with NaHCO$_3$ solution and water, washed with brine and dried over Na$_2$SO$_4$, filtered, and concentrated in vacuo. The residue was treated with approximately 25 mL hexane, causing precipitation of a pale-grey solid. This solid was collected by filtration and air-dried to yield 81 mg (27%) of the title compound $^1$H NMR (300 MHz, DMSO-$d_6$) δ 9.32 (s, 1H), 7.52 (d, J=7.2, 1H), 7.35 (dd, J=3.7, 1.3 1H), 7.10 (t, J=7.8, 1H), 6.87 (d, J=7.5, 1H), 6.65 (d, J=3.6, 1H), 4.78 (d, J=4.0, 1H), 3.90 (m, 1H), 2.97-2.80 (m, 2H), 2.79-2.66 (m, 1H), 2.53-2.43 (m, 1H), 2.23 (s, 3H), 1.92-1.80 (m, 1H), 1.67-1.53 (m, 1H). MS (ESI$^+$) m/z 379 (M+H).

Example 32

8-({5-[(4R)-4-isopropenylcyclohex-1-en-1-yl]-4-methyl-1,3-oxazol-2-yl}amino)-1,2,3,4-tetrahydronaphthalen-2-ol

Example 32A (R)-4-methyl-5-(4-(prop-1-en-2-yl)cyclohex-1-enyl)oxazole

A mixture of (R)-4-(prop-1-en-2-yl)cyclohex-1-enecarbaldehyde (0.574 g, 3.82 mmol), 1-(1-isocyanoethylsulfonyl)-4-methylbenzene (0.80 g, 3.82 mmol), and K$_2$CO$_3$ (1.06 g, 7.65 mmol) in MeOH (25 mL) was heated at reflux for 2 h. The reaction mixture was cooled to ambient temperature, concentrated in vacuo, and diluted with EtOAc. The organic solution was washed with water, separated, and concentrated in vacuo. The residue was chromatographed on silica gel with EtOAc/hexanes (0%-35%) to isolate 0.54 g (70%) of the title compound as an oil. $^1$H NMR (300 MHz, DMSO-$d_6$) δ 8.12 (s, 1H), 6.15-6.06 (m, 1H), 4.74 (s, 2H), 2.47-2.25 (m, 3H), 2.24-2.00 (m, 5H), 1.94-1.82 (m, 1H), 1.74 (s, 3H), 1.59-1.40 (m, 1H). MS (DCI$^+$) m/z 204 (M+H).

Example 32B (R)-2-chloro-4-methyl-5-(4-(prop-1-en-2-yl)cyclohex-1-enyl)oxazole To a solution of Example 32A (0.55 g, 2.7 mmol) in THF (20 mL) at −78° C. was added LiHMDS (1 M in THF, 3.25 mL, 3.25 mmol) dropwise over a period of 6-8 min. After 30 min hexachloroethane (1.28 g, 5.41 mmol) was added at once as a solid and the mixture was left to stir overnight warming to ambient temperature. The mixture was diluted with Et$_2$O and washed with aqueous NH$_4$Cl solution and water. The organic layer was separated and concentrated in vacuo, and the residue chromatographed on silica gel with EtOAc/hexanes (0%-20%) to yield 0.47 g (73%) of the title compound as an oil. $^1$H NMR (300 MHz, DMSO-$d_6$) δ 6.11 (m, 1H), 4.74 (m, 2H), 2.48-2.24 (m, 3H), 2.23-2.00 (m, 5H), 1.92-1.82 (m, 1H), 1.73 (s, 3H), 1.57-1.41 (m, 1H). MS (ESI$^+$) m/z 238 (M+H).

Example 32C 8-(4-methyl-5-((R)-4-(prop-1-en-2-yl)cyclohex-1-enyl)oxazol-2-ylamino)-1,2,3,4-tetrahydronaphthalen-2-ol A mixture of Example 32B (300 mg, 1.26 mmol) and Example 1A (350 mg, 1.26 mmol) in BuOH (12 mL) was heated to 110° C. After 3.5 hours, the reaction mixture was cooled to room temperature and 10 mL 1N HCl was added. The mixture was stirred for 30 minutes, and then diluted with water. The alcohol layer was separated, diluted with EtOAc, and washed with saturated NaHCO$_3$ solution, water and brine, dried over Na$_2$SO$_4$, filtered, and concentrated in vacuo. The residue was chromatographed on silica gel (Analogix® 25×60 column) with MeOH/CH$_2$Cl$_2$ (2% to 25%) as eluant to yield an oil, that was triturated with Et$_2$O to give a solid which was collected by filtration. The result was 163 mg (35%) of the title compound as a tan solid. $^1$H NMR (300 MHz, DMSO-$d_6$) δ 8.75 (s, 1H), 7.53 (d, J=7.9, 1H), 7.06 (t, J=7.8, 1H), 6.79 (d, J=7.3, 1H), 5.90 (m, 1H), 4.79 (d, J=3.9, 1H), 4.74 (s, 2H), 3.89 (m, 1H), 2.94-2.79 (m, 2H), 2.78-2.63 (m, 1H), 2.53-1.98 (m, 9H), 1.93-1.80 (m, 2H), 1.74 (s, 3H), 1.69-1.54 (m, 1H), 1.54-1.39 (m, 1H). MS (ESI$^+$) m/z 365 (M+H).

Example 33

8-{[5-(5-ethylthien-2-yl)-4-methyl-1,3-oxazol-2-yl]amino}-1,2,3,4-tetrahydronaphthalen-2-ol

Example 33A 5-(5-ethylthiophen-2-yl)-4-methyloxazole

A mixture of 5-ethylthiophene-2-carbaldehyde (0.670 g, 4.78 mmol), 1-(1-isocyanoethylsulfonyl)-4-methylbenzene (1.0 g, 4.8 mmol), and K$_2$CO$_3$ (0.859 g, 6.21 mmol) in MeOH (16 mL) was heated at reflux for 2 h, then cooled to room temperature and allowed to stand overnight. The mixture was poured into water and extracted with Et$_2$O, and the combined extracts were concentrated in vacuo. The residue was chromatographed on silica gel (Analogix® SF40-115 column, 15% to 30% EtOAc/hexanes eluant, 18 minutes) to afford 0.94 g (102%) of the title compound. $^1$H NMR (300 MHz, DMSO-$d_6$) δ 8.26 (s, 1H), 7.15 (d, J=3.6, 1H), 6.91 (dt, J=3.7, 1.0 1H), 2.85 (qd, J=7.5, 0.8 2H), 2.29 (s, 3H), 1.26 (t, J=7.5, 3H). MS (DCI$^+$) m/z 194 (M+H).

Example 33B 2-chloro-5-(5-ethylthiophen-2-yl)-4-methyloxazole

A solution of Example 33A (0.94 g, 4.8 mmol) in THF (20 mL) was cooled to −78° C., then treated slowly with LiHMDS (1M in THF, 6.3 mL, 6.3 mmol). The reaction was stirred at −78° C. for 20 min and then treated all at once with solid hexachloroethane (2.31 g, 9.75 mmol). The flask was removed from the cold bath, and the reaction mixture was allowed to stir overnight at room temperature. After this time, it was poured into water and extracted with Et$_2$O. The combined Et$_2$O extracts were concentrated in vacuo, and the residue was chromatographed on silica gel (Analogix® SF25-60 column; 100% hexane for 10 minutes, then 0% to 15% EtOAc/hexanes over 10 minutes) to afford 0.673 g (61%) of the title compound as a bright yellow oil. $^1$H NMR (300 MHz, DMSO-$d_6$) δ 7.17 (d, J=3.6, 1H), 6.93 (dt, J=3.7, 1.0 1H), 2.86 (qd, J=7.6, 1.0 2H), 2.27 (s, 3H), 1.26 (t, J=7.5, 3H). MS (DCI$^+$) m/z 228 (M+H).

Example 33C 8-(5-(5-ethylthiophen-2-yl)-4-methyloxazol-2-ylamino)-1,2,3,4-tetrahydronaphthalen-2-ol A mixture of Example 33B (82 mg, 0.36 mmol) and Example 1A (100 mg, 0.36 mmol) was heated in BuOH (2.4 mL) for 2 h at 120° C. The reaction was then cooled to room temperature and allowed to stand overnight. The reaction mixture was then stirred with 2.4 mL of 1N HCl for 1 h, and then diluted with EtOAc. The reaction mixture was washed with saturated NaHCO$_3$ solution (3×), water and brine, dried over Na$_2$SO$_4$, filtered, and concentrated in vacuo. The residue (containing residual BuOH) was triturated with hexane, resulting in a pale tan solid that was collected by filtration and air-dried. The result was 26 mg (20%) of the title compound. $^1$H NMR (300 MHz, DMSO-$d_6$) δ 9.02 (s, 1H), 7.54 (d, J=7.8, 1H), 7.08 (t, J=7.7, 1H), 6.91 (d, J=3.6, 1H), 6.86-6.79 (m, 2H), 4.79 (d, J=3.9, 1H), 3.90 (m, 1H), 2.97-2.64 (m, 5H), 2.53-2.42 (m, 1H), 2.17 (s, 3H), 1.92-1.79 (m, 1H), 1.67-1.51 (m, 1H), 1.25 (t, J=7.5, 3H). MS (ESI$^+$) m/z 355 (M+H).

Example 34

(2R)-8-({4-methyl-5-[5-(trifluoromethyl)pyridin-2-yl]-1,3-oxazol-2-yl}amino)-1,2,3,4-tetrahydronaphthalen-2-ol Example 34A Methyl 5-(trifluoromethyl)picolinate A solution of 2-bromo-5-(trifluoromethyl)pyridine (9 g, 40 mmol) in MeOH (130 mL) was added to Pd-dppf (0.813 g, 0.996 mmol) and Et$_3$N (11 mL, 80 mmol) in a 250 mL pressure bottle. The mixture was pressurized with carbon monoxide (60 psi), and stirred 3 hr at 80° C. The reaction was cooled to ambient temperature, filtered, and the solvents evaporated at reduced pressure. The residue was partitioned between water and ethyl acetate. The separated organic layer was washed with water and brine, dried (Na$_2$SO$_4$), filtered, and concentrated in vacuo. The crude product was chromatographed on silica gel (Analogix® 40×240 column, 10%-40% EtOAc/hexanes eluant) to afford 8.52 g (104%) of the title compound as a white solid. $^1$H NMR (300 MHz, CDCl$_3$) δ 9.01 (m, 1H), 8.28 (d, J=8.1, 1H), 8.12 (dd, J=2.1, 8.2, 1H), 4.06 (s, 3H). MS (ESI$^+$) m/z 206 (M+H).

Example 34B (5-(trifluoromethyl)pyridin-2-yl)methanol

NaBH$_4$ (0.369 g, 9.75 mmol) was added to Example 34A (1 g, 5 mmol) in EtOH (40 mL). The suspension was heated at reflux overnight. The reaction was cooled to ambient temperature and quenched with saturated NH$_4$Cl solution. The mixture was diluted with water and extracted with EtOAc. The separated organic layer was washed with water and brine, dried (Na$_2$SO$_4$), filtered, and concentrated in vacuo. The crude product was chromatographed on silica gel (Analogix® 25×40 column, 30%-50% EtOAc/hexanes eluant) to afford 0.62 g (72%) of the title compound as a colorless oil. $^1$H NMR (300 MHz, CDCl$_3$) δ 8.84 (s, 1H), 7.94 (dd, J=8.3, 2.1 1H), 7.43 (dd, J=8.2, 0.6 1H), 4.85 (d, J=5.2, 2H), 3.46 (t, J=5.3, 1H).

Example 34C 5-(trifluoromethyl)picolinaldehyde

A solution of Example 34B (3.89 g, 22.0 mmol) in CH$_2$Cl$_2$ (10 mL) was added to a deoxygenated solution of Dess-Martin periodinane (1,1,1-tris(acetyloxy)-1,1-dihydro-1,2-benziodoxol-3-(1H)-one, 10.3 g, 24.2 mmol) in CH$_2$Cl$_2$ (73 mL) in one portion. The reaction was stirred under nitrogen at ambient temperature for about 20 minutes after which a solid formed. The reaction was diluted with 50 mL CH$_2$Cl$_2$ and carefully quenched with approximately 30 mL of saturated NaHCO$_3$ solution. The undissolved solid was filtered, and the filtrate was transferred to a separatory funnel. The aqueous phase was extracted with CH$_2$Cl$_2$, and the combined organic layer was washed with brine, dried over Na$_2$SO$_4$, filtered, and evaporated at reduced pressure to 50 mL. This solution was then loaded on silica gel (Analogix® 40×150 column) and eluted with 25% to 50% EtOAc/hexanes. The result was 2.86 g (74%) of the title compound as a clear oil, which solidified on standing. $^1$H NMR (300 MHz, CDCl$_3$) δ 10.15 (s, 1H), 9.06 (m, 1H), 8.15 (m, 1H), 8.09 (d, J=8.1, 1H).

Example 34D 4-methyl-5-(5-(trifluoromethyl)pyridin-2-yl)oxazole

A mixture of 1-(1-isocyanoethylsulfonyl)-4-methylbenzene (3.20 g, 15.3 mmol), Example 34C (2.68 g, 15.3 mmol), and K$_2$CO$_3$ (2.54 g, 18.4 mmol) in MeOH (77 mL) was heated at reflux for 2.5 hr. The volatiles were evaporated at reduced pressure, the residue diluted with water, and the product extracted with Et$_2$O. The combined extract was washed with brine, dried over Na$_2$SO$_4$, filtered, and concentrated in vacuo. The crude product was purified by chromatography on silica gel (Analogix® 40×115 column, loaded as an Et$_2$O solution, 30% to 60% EtOAc/hexanes eluant) which yielded 3.37 g (97%) of the title compound as a white solid. $^1$H NMR (300 MHz, CDCl$_3$) δ 8.90 (m, 1H), 7.98 (dd, J=8.4, 2.2 1H), 7.91 (s, 1H), 7.76 (d, J=8.4, 1H), 2.67 (s, 3H). MS (ESI$^+$) m/z 229 (M+H).

Example 34E 2-chloro-4-methyl-5-(5-(trifluoromethyl)pyridin-2-yl)oxazole

A solution of Example 34D (3.37 g, 14.8 mmol) in THF (50 mL) was cooled to −78° C., followed by addition of LiHMDS (1M in THF, 16.3 ml, 16.3 mmol). After 0.5 hr at −78° C., hexachloroethane (3.50 g, 14.8 mmol) was added in one portion. The reaction was allowed to stir overnight with gradual warming to room temperature. The reaction was quenched with water and extracted with EtOAc. The combined organic extract was washed with water and brine, and then filtered through celite filter aid. The filtrate was dried over Na$_2$SO$_4$, filtered, and concentrated in vacuo. The residue was dissolved in minimal toluene and place on silica gel (Analogix® 25×115 column) and eluted with 2 column lengths of hexanes, then 5% to 50% EtOAc/hexanes. The result was 2.20 g (57%) of the title compound as a yellow solid. $^1$H NMR (300 MHz, CDCl$_3$) δ 8.88 (m, 1H), 8.00-7.93 (m, 1H), 7.72-7.66 (m, 1H), 2.63 (s, 3H). MS (DCI$^+$) m/z 263 (M+H).

Example 34F (R)-8-(4-methyl-5-(5-(trifluoromethyl)pyridin-2-yl) oxazol-2-ylamino)-1,2,3,4-tetrahydronaphthalen-2-ol Example 24E (1.24 g, 7.62 mmol) and Example 34E (2.20 g, 8.38 mmol) were taken up in isopropanol (31 mL), followed by addition of 2 drops of trifluoroacetic acid. The reaction was heated at reflux for 3 hr. The solution was cooled to ambient temperature and concentrated in vacuo, and the residue was dissolved in CH$_2$Cl$_2$/EtOAc. The organic solution was washed with saturated NaHCO$_3$ solution, water and brine, dried over Na$_2$SO$_4$, filtered, and concentrated in vacuo. The crude product was triturated with 1:1 Et$_2$O:hexanes and collected by filtration, then triturated again with CH$_2$Cl$_2$/EtOAc/MeOH. The resulting solid was collected by filtration and dried under vacuum to yield 1.82 g (61%) of the title compound as a very pale yellow solid. $^1$H NMR (300 MHz, CH$_3$OH-d$_4$) δ 8.79 (m, 1H), 8.03 (dd, J=8.5, 2.2 1H), 7.59 (d, J=8.5, 1H), 7.39 (d, J=7.8, 1H), 7.16 (t, J=7.8, 1H), 6.99 (d, J=7.7, 1H), 4.07 (m, 1H), 3.11-2.93 (m, 2H), 2.92-2.78 (m, 1H), 2.61 (dd, J=16.7, 7.9 1H), 2.51 (s, 3H), 2.09-1.97 (m, 1H), 1.84-1.69 (m, 1H). MS (ESI$^+$) m/z 390 (M+H).

Example 35

2-(4-{2-[(7-hydroxy-5,6,7,8-tetrahydronaphthalen-1-yl)amino]-4-methyl-1,3-oxazol-5-yl}phenyl)-2-methylpropanenitrile Example 35A 4-(2-cyanopropan-2-yl)benzonitrile KHMDS (0.5 M in toluene, 99 mL, 49 mmol) was added dropwise via addition funnel to a solution of 4-fluorobenzonitrile (4.0 g, 33.0 mmol) and isobutyronitrile (12 mL, 132 mmol) in toluene (20 mL) at ambient temperature. Upon complete addition the reaction mixture was heated to 60° C. After 2 hr the reaction mixture was cooled to ambient temperature and poured into 1 N aq HCl. The product was extracted with EtOAc, and the combined organic extract was washed with brine, dried (Na$_2$SO$_4$), filtered, and concentrated in vacuo. The residue was triturated with 20% EtOAc/hexanes resulting in a yellow solid that was collected by suction filtration, washed with Et$_2$O, and air-dried. The result was 1.84 g product as a yellow solid. The filtrate was concentrated and purified by flash chromatography (Analogix® Intelliflash 280™; 30% EtOAc/hexanes eluant, loading w/CH$_2$Cl$_2$/MeOH; SF40-115 g column) which afforded an additional 1.66 g product as a white solid. The two batches of material were combined to afford 3.50 g (62%) of the title compound. $^1$H NMR (300 MHz, DMSO-d$_6$) δ 7.95-7.89 (m, 2H), 7.77-7.71 (m, 2H), 1.71 (s, 6H). MS (DCI$^+$) m/z 188 (M+NH$_4$).

Example 35B 2-(4-formylphenyl)-2-methylpropanenitrile

A suspension of lithium tris(dihexylamino)aluminum hydride, prepared according to Cha, J. S., et al; Org. Prep. Proc. Int. 1992, 24(3), 331-334, (21.2 g, 36 mmol) in THF (20 mL) was added via syringe to a solution of Example 35A (3.50 g, 20.6 mmol) in THF (50 mL) at 0° C. The reaction was allowed to proceed for 8 hr at 0° C., and then carefully quenched by addition of 3 N aq HCl(100 mL). The mixture was diluted with EtOAc, and the separated aqueous phase was extracted with EtOAc. The combined organic layer was washed with brine causing a white precipitate to form, which was filtered off. The filtrate was dried over Na$_2$SO$_4$, filtered, and concentrated in vacuo. The resulting yellow solid was triturated with hexanes and filtered. The filtrate was concentrated in vacuo, and the residue was purified by flash chromatography (Analogix® Intelliflash 280; 5% to 25% EtOAc/hexanes eluant; SF40-115 g column) to yield 2.24 g (63%) of the title compound as a pale yellow oil. $^1$H NMR (300 MHz, DMSO-d$_6$) δ 10.03 (s, 1H), 8.00-7.93 (m, 2H), 7.80-7.74 (m, 2H), 1.73 (s, 6H). MS (DCI$^+$) m/z 173 (M$^+$).

Example 35C 2-methyl-2-(4-(4-methyloxazol-5-yl)phenyl)propanenitrile

A mixture of Example 35B (2.24 g, 12.9 mmol), 1-(1-isocyanoethylsulfonyl)-4-methylbenzene (2.71 g, 12.9 mmol), and K$_2$CO$_3$ (2.15 g, 15.5 mmol) in MeOH (60 mL) was heated at reflux for 2 hr. The reaction was cooled to ambient temperature, and the volatiles removed at reduced pressure. The residue was partitioned between H$_2$O and Et$_2$O. The separated aqueous phase was extracted with Et$_2$O, and the combined organic layer was washed with brine, dried (Na$_2$SO$_4$), filtered, and concentrated in vacuo. Flash chromatography (Analogix® Intelliflash 280™; 15% to 40% EtOAc/hexanes eluant; SF40-150 g column) yielded 2.35 g (80%) of the title compound as a colorless oil. $^1$H NMR (300 MHz, DMSO-d$_6$) δ 8.35 (s, 1H), 7.71-7.61 (m, 4H), 2.37 (s, 3H), 1.71 (s, 6H). MS (DCI$^+$) m/z 227 (M+H).

Example 35D 2-(4-(2-chloro-4-methyloxazol-5-yl)phenyl)-2-methylpropanenitrile

To a solution of Example 35C (2.35 g, 10.4 mmol) in THF (50 mL) at −78° C. was added LiHMDS (1.0 M in THF, 11.4 ml, 11.4 mmol) slowly via syringe. The solution was stirred 45 min, and then solid hexachloroethane (3.69 g, 15.6 mmol) was added in one portion. The reaction was allowed to proceed for 16 hr, gradually warming to ambient temperature. The reaction was quenched with half-saturated aq NH$_4$Cl solution, and the product was extracted with Et$_2$O. The combined organic extract was washed with brine, dried (Na$_2$SO$_4$), filtered, and concentrated in vacuo. Flash chromatography (Analogix® Intelliflash 280™; 0% to 20% EtOAc/hexanes eluant; SF40-150 g column) yielded 2.52 g (93%) of the title compound as a colorless oil. $^1$H NMR (300 MHz, DMSO-d$_6$) δ 7.66 (s, 4H), 2.36 (s, 3H), 1.71 (s, 6H). MS (DCI$^+$) m/z 261 (M+H).

Example 35E 2-(4-(2-(7-hydroxy-5,6,7,8-tetrahydronaphthalen-1-ylamino)-4-methyloxazol-5-yl)phenyl)-2-methylpropanenitrile Example 24A (277 mg, 1.70 mmol) and Example 35D (442 mg, 1.70 mmol) were combined in BuOH (7 mL) and heated to 110° C. After 1 hr the solution was cooled, diluted with EtOAc, and poured into saturated aq NaHCO$_3$ solution. The separated organic layer was washed with brine, dried (Na$_2$SO$_4$), filtered, and concentrated in vacuo. Hexane was added to the residue, and the resulting solid was collected by vacuum filtration and air-dried. The result was 494 mg (75%) of the title compound as a pale pink solid. $^1$H NMR (300 MHz, DMSO-d$_6$) δ 9.04 (s, 1H), 7.61-7.49 (m, 5H), 7.09 (t, J=7.8, 1H), 6.84 (d, J=7.4, 1H), 4.80 (d, J=4.0, 1H), 3.92 (m, 1H), 3.00-2.81 (m, 2H), 2.80-2.65 (m, 1H), 2.56-2.44 (m, 1H), 2.28 (s, 3H), 1.93-1.81 (m, 1H), 1.70 (s, 6H), 1.69-1.53 (m, 1H). MS (ESI$^+$) m/z 388 (M+H).

Example 36

8-{[5-(4-cyclopropyl-3-fluorophenyl)-4-methyl-1,3-oxazol-2-yl]amino}-1,2,3,4-tetrahydronaphthalen-2-ol Example 36A 5-(4-bromo-3-fluorophenyl)-4-methyloxazole A mixture of 1-(1-isocyanoethylsulfonyl)-4-methylbenzene (1.67 g, 7.97 mmol), 4-bromo-3-fluorobenzaldehyde (1.62 g, 7.97 mmol), and K$_2$CO$_3$ (2.20 g, 15.9 mmol) in MeOH (40 mL) was heated to reflux. After 1.5 hr additional 1-(1-isocyanoethylsulfonyl)-4-methylbenzene (106 mg, 0.51 mmol) was added and the reaction mixture was again heated at reflux for 1.5 hr. The reaction was cooled to ambient temperature, water (200 mL) was added and the product was extracted with EtOAc (200 mL). The organic layer was washed with brine and dried over Na$_2$SO$_4$, filtered, and concentrated in vacuo. The residue was chromatographed on silica gel (Analogix® SF25-40G column, 0%-30% EtOAc/hexanes, 30 mL/min), which yielded 1.86 g (91%) of the title compound as an orange solid. $^1$H NMR (300 MHz, CH$_3$OH-d$_4$) δ 8.18 (s, 1H), 7.73 (dd, J=8.4, 7.3 1H), 7.49 (dd, J=9.9, 2.0 1H), 7.41 (dd, J=8.3, 1.8 1H), 2.42 (s, 3H). MS (DCI$^+$) m/z 256/258 (M+H).

Example 36B 5-(4-cyclopropyl-3-fluorophenyl)-4-methyloxazole

A mixture of Example 36A (870 mg, 3.40 mmol), Pd(OAc)$_2$ (38.1 mg, 0.170 mmol), tricyclohexylphosphine (95 mg, 0.34 mmol), K$_3$PO$_4$ (2524 mg, 11.9 mmol), and cyclopropylboronic acid (379 mg, 4.42 mmol) in toluene (16 mL) and water (0.8 mL) was heated in a microwave reactor at 100° C. for 1.5 hr. A second, identical reaction was performed. The two reactions were combined, and then filtered, rinsed with EtOAc, and concentrated to an orange oil. The crude product was chromatographed on silica gel (Analogix® SF25-40G column, 0%-25% EtOAc/hexanes, 30 mL/min), which yielded 1.37 g (93%) of the title compound as yellow crystals. $^1$H NMR (300 MHz, CH$_3$OH-d$_4$) δ 8.13 (s, 1H), 7.35 (dd, J=8.1, 1.8 1H), 7.29 (dd, J=11.4, 1.8 1H), 7.06 (t, J=8.0, 1H), 2.39 (s, 3H), 2.17-2.05 (m, 1H), 1.03 (dd, J=8.5, 6.4, 4.3 2H), 0.81-0.73 (m, 2H). MS (DCI$^+$) m/z 218 (M+H).

Example 36C 2-chloro-5-(4-cyclopropyl-3-fluorophenyl)-4-methyloxazole

Example 36B (1.25 g, 5.75 mmol) was dissolved in THF (30 mL) and cooled to −75° C. for 10 min, followed by addition of LiHMDS (1.0 M in THF, 7.6 mL, 7.6 mmol) in portions. The orange solution was stirred at −75° C. for 25 min. Hexachloroethane (2.74 g, 11.6 mmol) was added and the reaction mixture was stirred overnight at ambient temperature. Saturated NH$_4$Cl solution (200 mL) was added and the product was extracted with 1:1 EtOAc:hexanes (2×200 mL). The combined organic layer was washed with brine and dried over Na$_2$SO$_4$, filtered, and concentrated to a yellow oil. Chromatography on silica gel (Analogix® SF25-40G column with 0%-20% EtOAc/hexanes, 30 mL/min) yielded 1.40 g (97%) of the title compound as light yellow crystals. $^1$H NMR (300 MHz, CH$_3$OH-d$_4$) δ 7.30 (dd, J=8.1, 1.8 1H), 7.24 (dd, J=11.3, 1.7 1H), 7.06 (t, J=8.0, 1H), 2.36 (s, 3H), 2.17-2.05 (m, 1H), 1.03 (dd, J=8.5, 6.5, 4.3 2H), 0.81-0.73 (m, 2H). MS (DCI$^+$) m/z 252 (M+H).

Example 36D 8-(5-(4-cyclopropyl-3-fluorophenyl)-4-methyloxazol-2-ylamino)-1,2,3,4-tetrahydronaphthalen-2-ol A mixture of Example 36C (200 mg, 0.795 mmol) and Example 24A (130 mg, 0.795 mmol) in BuOH (8 mL) was heated at 110° C. for 3.5 hr. One drop of concentrated aqueous HCl was added and heating was continued 0.5 hr. The reaction was cooled to ambient temperature and concentrated in vacuo. The crude product was purified by chromatography on silica gel (Analogix® 45×115 column, 5% to 40% MeOH/CH$_2$Cl$_2$) which yielded 132 mg (44%) of the title compound as a light tan solid. $^1$H NMR (300 MHz, DMSO-d$_6$) δ 9.01 (s, 1H), 7.57 (d, J=7.9, 1H), 7.23-7.00 (m, 4H), 6.83 (d, J=7.5, 1H), 4.79 (d, J=3.9, 1H), 3.98-3.85 (m, 1H), 2.99-2.81 (m, 2H), 2.80-2.66 (m, 1H), 2.54-2.42 (m, 1H), 2.25 (s, 3H), 2.10-1.98 (m, 1H), 1.92-1.80 (m, 1H), 1.69-1.52 (m, 1H), 0.98 (dd, J=8.4, 6.4, 4.2 2H), 0.77-0.70 (m, 2H). MS (ESI$^+$) m/z 379 (M+H).

Example 37

8-{[5-(4-chloro-3-fluorophenyl)-4-methyl-1,3-oxazol-2-yl]amino}-1,2,3,4-tetrahydronaphthalen-2-ol Example 37A 5-(4-chloro-3-fluorophenyl)-4-methyloxazole A mixture of 1-(1-isocyanoethylsulfonyl)-4-methylbenzene (1.56 g, 7.44 mmol), 4-chloro-3-fluorobenzaldehyde (1.18 g, 7.44 mmol), and K$_2$CO$_3$ (2.06 g, 14.9 mmol) in MeOH (35 mL) was heated to reflux. After 1.5 hr water (200 mL) was added and the product was extracted with EtOAc (200 mL). The organic layer was washed with brine and dried over Na$_2$SO$_4$, filtered, and concentrated to an orange oil. Chromatography on silica gel (Analogix® SF25-40G, 0%-30% EtOAc/hexanes, 30 mL/min) afforded 1.35 g (86%) of the title compound as a yellow solid. $^1$H NMR (300 MHz, CH$_3$OH-d$_4$) δ 8.18 (s, 1H), 7.62-7.55 (m, 1H), 7.52 (dd, J=1.9, 10.3, 1H), 7.49-7.44 (m, 1H), 2.42 (s, 3H). MS (DCI$^+$) m/z 212 (M+H).

Example 37B 2-chloro-5-(4-chloro-3-fluorophenyl)-4-methyloxazole

Example 37A (1.22 g, 5.78 mmol) was dissolved in THF (30 mL) and cooled to −75° C. for 10 min. LiHMDS (1.0 M in THF, 7.8 mL, 7.8 mmol) was added in portions, and the reaction mixture was stirred at −75° C. for 25 min. Hexachloroethane (2.77 g, 11.7 mmol) was then added and the reaction stirred overnight at ambient temperature. Saturated NH$_4$Cl solution (200 mL) was added and the product was extracted with 1:1 EtOAc:hexanes (2×200 mL). The combined organic layer was washed with water, washed with brine and dried over Na$_2$SO$_4$, filtered, and concentrated to a yellow slurry. The crude product was purified by chromatography on silica gel (Analogix® SF25-40G column, 0%-20% EtOAc/hexanes, 30 mL/min) which yielded 1.29 g (91%) of the title compound as an off-white solid. $^1$H NMR (300 MHz, CH$_3$OH-d$_4$) δ 7.63-7.56 (m, 1H), 7.48 (dd, J=10.2, 2.0 1H), 7.44-7.39 (m, 1H), 2.38 (s, 3H). MS (DCI$^+$) m/z 246 (M+H).

Example 37C 8-(5-(4-chloro-3-fluorophenyl)-4-methyloxazol-2-ylamino)-1,2,3,4-tetrahydronaphthalen-2-ol Example 24A (400 mg, 2.45 mmol) and Example 37B (603 mg, 2.45 mmol) were taken up in BuOH (25 mL) and the mixture was heated at reflux for 1.5 hr. The reaction was cooled to ambient temperature and concentrated to a purple oil. Hexane (~60 mL) and BuOH(~5 mL) were added, and the mixture was stirred overnight. The resulting gray solid was collected by filtration, rinsed with hexane, and air dried. This material was triturated with 1:1 Et$_2$O:hexane, collected by filtration and rinsed with 1:1 Et$_2$O:hexane, and vacuum dried overnight to afford product that was contaminated with BuOH. This material was then chromatographed on silica gel (Analogix® SF25-40G column, 0%-50% MeOH/CH$_2$Cl$_2$, 30 mL/min) to yield a purple foam that was triturated with Et$_2$O, then collected by filtration and rinsed with Et$_2$O, and vacuum dried overnight. The result was 530 mg, (58%) of the title compound as a gray powder. $^1$H NMR (300 MHz, DMSO-d$_6$) δ 9.22 (s, 1H), 7.64 (t, J=8.2, 1H), 7.55 (d, J=7.9, 1H), 7.39 (dd, J=10.9, 2.0 1H), 7.32 (dd, J=8.6, 1.9 1H), 7.1 1 (t, J=7.8, 1H), 6.86 (d, J=7.5, 1H), 3.91 (m, 1H), 2.99-2.65 (m, 3H), 2.54-2.40 (m, 1H), 2.28 (s, 3H), 1.93-1.79 (m, 1H), 1.67-1.53 (m, 1H). MS (ESI$^+$) m/z 373 (M+H).

Example 38

8-({5-[4-(difluoromethyl)phenyl]-4-methyl-1,3-oxazol-2-yl}amino)-1,2,3,4-tetrahydronaphthalen-2-ol Example 38A Methyl 4-(difluoromethyl)benzoate A solution of 4-(difluoromethyl)benzoic acid (5.47 g, 31.8 mmol) in MeOH (100 mL) was treated with concentrated aq HCl (0.5 mL, 6.0 mmol), and the reaction mixture was heated to reflux. After 24 hr the solution was cooled to ambient temperature and concentrated in vacuo. The residue was taken up in Et$_2$O and washed with saturated aqueous NaHCO$_3$ solution and brine, dried over MgSO$_4$, filtered, and concentrated in vacuo. The result was 5.82 g (98%) of the title compound as a white solid. $^1$H NMR (300 MHz, DMSO-d$_6$) δ 8.13-8.06 (m, 2H), 7.76-7.69 (m, 2H), 7.14 (t, J=55.5, 1H), 3.89 (s, 3H).

Example 38B (4-(difluoromethyl)phenyl)methanol

A solution of LAH (1.0 M in THF, 31 mL, 31 mmol) was added dropwise to a solution of Example 38A (5.82 g, 31.3 mmol) in THF (100 mL) at 0° C. The reaction was stirred for 1 hr, then quenched by careful addition of solid Na$_2$SO$_4$.10H$_2$O. The mixture was warmed to ambient temperature and stirred 30 min. Celite filter aid was added and the mixture was filtered. The filtrate was concentrated in vacuo to yield 4.02 g (81%) of the title compound as a colorless oil. $^1$H NMR (300 MHz, DMSO-d$_6$) δ 7.52 (d, J=8.2, 2H), 7.48-7.41 (m, 2H), 7.00 (t, J=56.0, 1H), 5.30 (t, J=5.7, 1H), 4.55 (d, J=5.4, 2H).

Example 38C 4-(difluoromethyl)benzaldehyde

Solid pyridinium chlorochromate (8.22 g, 38.1 mmol) was added slowly to a mixture of Example 38B (4.02 g, 25.4 mmol) and celite filter aid (8.5 g) in CH$_2$Cl$_2$ (125 mL) at ambient temperature. The reaction was allowed to proceed for 30 min, and then filtered. The filtrate was concentrated in vacuo to give a black oil. Flash chromatography (Analogix® Intelliflash 280™; 15% EtOAc/hexanes eluant; SF40-115 g column) yielded 3.68 g (93%) of the title compound as a colorless oil. $^1$HNMR (300 MHz, DMSO-d$_6$) δ 10.09 (s, 1H), 8.08-8.02 (m, 2H), 7.84-7.76 (m, 2H), 7.18 (t, J=55.5, 1H).

Example 38D 5-(4-(difluoromethyl)phenyl)-4-methyloxazole

A mixture of Example 38C (3.68 g, 23.6 mmol), 1-(1-isocyanoethylsulfonyl)-4-methylbenzene (4.93 g, 23.6 mmol), and K$_2$CO$_3$ (3.26 g, 23.6 mmol) in MeOH (110 mL) was heated to reflux. After 1 hr the reaction mixture was cooled to ambient temperature and the volatiles evaporated at reduced pressure. The residue was partitioned between Et$_2$O and H$_2$O. The separated aqueous phase was extracted with Et$_2$O, and the combined organic extract was washed with brine, dried (Na$_2$SO$_4$), filtered, and concentrated in vacuo. Flash chromatography (Analogix® Intelliflash 280™; 5% to 25% EtOAc/hexanes eluant; SF40-150 g column) afforded 4.39 g (89%) of the title compound as a white solid. $^1$H NMR (300 MHz, DMSO-d$_6$) δ 8.40 (s, 1H), 7.80-7.73 (m, 2H), 7.69 (d, J=8.6, 2H), 7.09 (t, J=55.3, 1H), 2.40 (s, 3H). MS (DCI$^+$) m/z 210 (M+H).

Example 38E 2-chloro-5-(4-(difluoromethyl)phenyl)-4-methyloxazole

To a solution of Example 38D (4.39 g, 21.0 mmol) in THF (100 mL) at −78° C. was added LiHMDS (1.0 M in THF, 23 ml, 23 mmol) slowly via syringe. The solution was stirred 45 min, and then solid hexachloroethane (5.46 g, 23.1 mmol) was added in one portion. The reaction was allowed to proceed for 24 hr, gradually warming to ambient temperature. The reaction was quenched with half-saturated aq NH$_4$Cl solution, and the product was extracted with Et$_2$O. The combined organic extract was washed with brine, dried (Na$_2$SO$_4$), filtered, and concentrated in vacuo. Flash chromatography (Analogix® Intelliflash 280™; 0% to 20% EtOAc/hexanes eluant; SF40-240 g column) yielded 3.91 g (76%) of the title compound as a white solid. $^1$H NMR (300 MHz, DMSO-d$_6$) δ 7.72 (m, 4H), 7.10 (t, J=55.7, 1H), 2.39 (s, 3H). MS (DCI$^+$) m/z 244 (M+H).

Example 38F 8-(5-(4-(difluoromethyl)phenyl)-4-methyloxazol-2-ylamino)-1,2,3,4-tetrahydronaphthalen-2-ol A mixture of Example 24A (181 mg, 1.11 mmol) and Example 38E (270 mg, 1.11 mmol) in BuOH (5 mL) was heated at 110° C. for 1 hr. The reaction was cooled to ambient temperature, diluted with EtOAc, and poured into aq saturated NaHCO$_3$ solution. The separated organic layer was washed with brine, dried (Na$_2$SO$_4$), filtered, and concentrated in vacuo to approximately 3 mL. Hexane was added to precipitate the product, and the resulting solid was collected by vacuum filtration, washed with hexane and minimal Et$_2$O, and dried in the vacuum oven at 50° C. for 30 min. The result was 312 mg (76%) of the title compound as a pale pink solid. $^1$H NMR (300 MHz, DMSO-d$_6$) δ 9.11 (s, 1H), 7.66-7.52 (m, 5H), 7.10 (t, J=7.8, 1H), 7.03 (t, J=56.0, 1H), 6.88-6.82 (m, 1H), 4.80 (d, J=3.9, 1H), 3.91 (m, 1H), 3.00-2.81 (m, 2H), 2.80-2.66 (m, 1H), 2.56-2.43 (m, 1H), 2.31 (s, 3H), 1.93-1.80 (m, 1H), 1.69-1.53 (m, 1H). MS (ESI$^+$) m/z 371 (M+H).

Example 39

(2R)-8-({5-[4-(difluoromethyl)phenyl]-4-methyl-1,3-oxazol-2-yl}amino)-1,2,3,4-tetrahydronaphthalen-2-ol A mixture of Example 24E (2.40 g, 14.7 mmol) and Example 38E (3.58 g, 14.7 mmol) in BuOH (70 mL) was heated at 120° C. for 1 hr. One drop of trifluoroacetic acid was added and the red solution was heated at reflux for 30 min. The reaction was cooled to ambient temperature and diluted with EtOAc (500 mL). The organic mixture was washed with saturated NaHCO$_3$ solution, washed with brine and dried over Na$_2$SO$_4$, filtered, and concentrated in vacuo to a give brown slurry. The crude product was supported on silica gel and chromatographed (Analogix® SF40-115G, 50%-100% EtOAc/CH$_2$Cl$_2$ eluant, 70 mL/min) which yielded both pure and impure lots. The chromatography was repeated on the impure material (Analogix® SF25-60G column, 50%-100% EtOAc/CH$_2$Cl$_2$ eluant, 35 mL/min) with similar results. The remaining impure material was triturated with 1:1 Et$_2$O/hexanes in a sonicator, and the resulting solid was collected by filtration, washed with 1:1 Et$_2$O/hexanes, and vacuum dried. This material was combined with the pure lots from the chromatographies to afford 3.66 g (67%) of the title compound as a tan powder. $^1$H NMR (300 MHz, CH$_3$OH-d$_4$) δ 7.66-7.53 (m, 4H), 7.39 (d, J=7.8, 1H), 7.14 (t, J=7.8, 1H), 6.96 (d, J=9.1, 1H), 6.74 (t, J=56.3, 1H), 4.12-4.01 (m, 1H), 3.1-2.78 (m, 3H), 2.60 (dd, J=16.8, 7.9 1H), 2.32 (s, 3H), 2.09-1.97 (m, 1H), 1.83-1.67 (m, 1H). MS (ESI$^+$) m/z 371 (M+H).

Example 40

8-({4-methyl-5-[4-(pentafluoro-lambda~6~sulfanyl)phenyl]-1,3-oxazol-2-yl}amino)-1,2,3,4-tetrahydronaphthalen-2-ol

Example 40A 4-(Pentafluorothio)benzaldehyde

A solution of 4-iodophenylsulfur pentafluoride (250 mg, 0.757 mmol) in acetonitrile (10 mL) was added to a 100 mL pressure bottle containing tetrakis(triphenylphosphine)palladium(0) (43.8 mg, 0.038 mmol), hexamethylphosphoramide (1.25 mL, 7.18 mmol), and poly(methylhydrosiloxane) (1.0 mL, 0.76 mmol). The reaction was pressurized with carbon monoxide (50 psi), and stirred for 20 hr at 80° C. The mixture was cooled to ambient temperature, water (100 mL) was added, and the product was extracted with Et$_2$O (2×100 mL). The organic layer was washed with brine and dried over Na$_2$SO$_4$, filtered, and concentrated in vacuo to a yellow oil. The crude product was chromatographed on silica gel (Analogix® SF10-8G column, 0%-25% EtOAc/hexanes, 10 mL/min) to give 151 mg (86%) of the title compound as a colorless liquid. $^1$H NMR (300 MHz, DMSO-d$_6$) δ 10.12 (s, 1H), 8.21-8.08 (m, 4H).

Example 40B 4-methyl-5-(4-(pentafluorothio)phenyl)oxazole

A mixture of 1-(1-isocyanoethylsulfonyl)-4-methylbenzene (138 mg, 0.659 mmol), Example 40A (151 mg, 0.650 mmol), and K$_2$CO$_3$ (183 mg, 1.32 mmol) in MeOH (5 mL) was heated at reflux for 3 hr, then cooled and stirred overnight at ambient temperature. Water (50 mL) was added and the product was extracted with EtOAc (50 mL). The organic layer was washed with brine and dried over Na$_2$SO$_4$, filtered, and concentrated in vacuo. The crude product was chromatographed on silica gel (Analogix® SF10-8G column, 0%-35% EtOAc/hexanes, 10 mL/min) to afford 117 mg (63%) of the title compound as a colorless oil. $^1$H NMR (300 MHz, CH$_3$OH-d$_4$) δ 8.23 (s, 1H), 7.98-7.91 (m, 2H), 7.84 (d, J=9.0, 2H), 2.47 (s, 3H). MS (DCI$^+$) m/z 286 (M+H).

Example 40C 2-chloro-4-methyl-5-(4-(pentafluorothio)phenyl)oxazole

A solution of Example 40B (117 mg, 0.41 mmol) in THF (4 mL) was cooled to −75° C. for 5 min. LiHMDS (1.0 M in THF, 0.56 mL, 0.56 mmol) was added dropwise and the resulting yellow solution was stirred at −75° C. for 25 min. Solid hexachloroethane (200 mg, 0.845 mmol) was added and the reaction mixture was stirred overnight at ambient temperature. A solution of saturated aqueous NH$_4$Cl solution (50 mL) was added and the product was extracted with 50 mL EtOAc. The separated organic layer was washed with brine and dried over Na$_2$SO$_4$, filtered, and concentrated to a light yellow residue. Chromatography on silica gel (Analogix® SF10-8G column, 0%-35% EtOAc/hexanes, 10 mL/min) gave 85 mg (65%) of the title compound as a white solid. $^1$H NMR (300 MHz, CH$_3$OH-d$_4$) δ 7.98-7.91 (m, 2H), 7.79 (d, J=8.6, 2H), 2.44 (s, 3H). MS (DCI$^+$) m/z 320 (M+H).

Example 40D 8-(4-methyl-5-(4-(pentafluorothio)phenyl)oxazol-2-ylamino)-1,2,3,4-tetrahydronaphthalen-2-ol A mixture of Example 24A (44 mg, 0.27 mmol) and Example 40C (82 mg, 0.26 mmol) in BuOH (3 mL) was heated at reflux for 1 hr. The reaction was cooled to ambient temperature, diluted with 50 mL EtOAc, and washed with saturated NaHCO$_3$ solution, washed with brine and dried over Na$_2$SO$_4$, filtered, and concentrated in vacuo. The resulting purple solid was supported on silica gel and chromatographed (Analogix® SF10-8G column, 50%-100% EtOAc/CH$_2$Cl$_2$, 12 mL/min) to yield 89 mg (78%) of the title compound as a white solid. $^1$H NMR (300 MHz, DMSO-d$_6$) δ 9.25 (s, 1H), 7.93 (d, J=9.1, 2H), 7.63 (d, J=8.8, 2H), 7.53 (d, J=7.1, 1H), 7.11 (t, J=7.8, 1H), 6.87 (d, J=7.5, 1H), 4.79 (d, J=4.0, 1H), 3.98-3.85 (m, 1H), 3.00-2.81 (m, 2H), 2.81-2.66 (m, 1H), 2.56-2.44 (m, 1H), 2.33 (s, 3H), 1.94-1.81 (m, 1H), 1.69-1.54 (m, 1H). MS (ESI$^+$) m/z 447 (M+H).

Example 41

(2R)-8-{[5-(4-chloro-3-fluorophenyl)-4-methyl-1,3-oxazol-2-yl]amino}-1,2,3,4-tetrahydronaphthalen-2-ol A mixture of Example 24E (2.97 g, 18.2 mmol) and Example 37B (4.47 g, 18.2 mmol) in BuOH (90 mL) was heated to reflux. After 1 hr the reaction mixture was cooled to ambient temperature and diluted with EtOAc (500 mL). The organic solution was washed with saturated NaHCO$_3$ solution, washed with brine and dried over Na$_2$SO$_4$, filtered, and concentrated in vacuo to a beige solid. Trituration with 1:1 Et$_2$O/hexanes gave a gray solid that was collected by filtration, and then supported on silica gel and eluted with 50%-100% EtOAc/CH$_2$Cl$_2$ (Analogix® SF40-80G column, 65 mL/min flow rate) to yield 4.98 g (74%) of the title compound as a beige solid. $^1$H NMR (300 MHz, DMSO-d$_6$) δ 9.13 (s, 1H), 7.63 (t, J=8.2, 1H), 7.55 (d, J=7.3, 1H), 7.38 (dd, J=10.9, 2.0, 1H), 7.31 (dd, J=8.4, 1.9, 1H), 7.10 (t, J=7.8, 1H), 6.86 (d, J=7.0, 1H), 4.80 (d, J=4.0, 1H), 3.98-3.85 (m, 1H), 2.99-2.81 (m, 2H), 2.81-2.65 (m, 1H), 2.55-2.41 (m, 1H), 2.28 (s, 3H), 1.93-1.81 (m, 1H), 1.69-1.53 (m, 1H). MS (ESI$^+$) m/z 373 (M+H).

Example 42

(2R)-8-{[5-(4-bromo-3-fluorophenyl)-4-methyl-1,3-oxazol-2-yl]amino}-1,2,3,4-tetrahydronaphthalen-2-ol Example 29C (2.7 g) was dissolved in (50/50) ethanol/hexane (1 g/200 mL after addition of minimal Et$_2$NH and sonication), loaded on a Chiralpak AD-H SFC (3 cm ID×25 cm) preparative chiral HPLC column (20 mL/injection), and eluted with ethanol/hexane (50/50) at 40° C. with a flow rate of 30 mL/min. The early eluting peak was collected and the solvent evaporated to afford 1.18 g (87%) of the title compound as a pale gray solid. Analytical chiral HPLC (Chiralpak AD-H 4.6 mm ID×25 cm, 40% methanol in supercritical CO$_2$ (200 bar), 40° C., 3 mL/min) showed the isolated material to have 98.9% ee. $^1$H NMR (300 MHz, DMSO-d$_6$) δ 9.13 (s, 1H), 7.79-7.70 (m, 1H), 7.55 (d, J=7.9, 1H), 7.35 (dd, J=10.4, 1.9, 1H), 7.25 (dd, J=8.5, 2.0, 1H), 7.10 (t, J=7.8, 1H), 6.86 (d, J=7.4, 1H), 4.80 (d, J=4.0, 1H), 3.99-3.85 (m, 1H), 2.99-2.81 (m, 2H), 2.80-2.66 (m, 1H), 2.55-2.41 (m, 1H), 2.28 (s, 3H), 1.94-1.80 (m, 1H), 1.69-1.53 (m, 1H). MS (ESI$^+$) m/z 417/419 (M+H). [□]$_D$=+4.0° (c 0.3, MeOH).

Example 43

(2R)-8-({4-ethyl-5-[4-(trifluoromethyl)phenyl]-1,3-oxazol-2-yl}amino)-1,2,3,4-tetrahydronaphthalen-2-ol

Example 43A 4-ethyl-5-(4-(trifluoromethyl)phenyl)oxazole

A mixture of 4-(trifluoromethyl)benzaldehyde (3.60 mL, 27.0 mmol), 1-(1-isocyanopropylsulfonyl)-4-methylbenzene (6.02 g, 27.0 mmol), and K$_2$CO$_3$ (4.47 g, 32.4 mmol) in MeOH (100 mL) was heated to reflux. After 1.5 hr the reaction mixture was cooled to ambient temperature, and the volatiles evaporated at reduced pressure. The residue was partitioned between Et$_2$O (100 mL) and H$_2$O (100 mL). The separated aqueous phase was extracted with Et$_2$O. The combined organic extract was washed with brine, dried (MgSO$_4$), filtered, and concentrated in vacuo. Chromatography on silica gel (Analogix® Intelliflash 280™; SF40-150 g column; 10% to 30% EtOAc/hexanes eluant, 30 min) afforded 5.75 g (88%) of the title compound as a pale yellow oil. $^1$H NMR (300 MHz, DMSO-d$_6$) δ 8.44 (s, 1H), 7.90-7.78 (m, 4H), 2.79 (q, J=7.5, 2H), 1.23 (t, J=7.5, 3H). MS (DCI$^+$) m/z 242 (M+H).

Example 43B 2-chloro-4-ethyl-5-(4-(trifluoromethyl)phenyl)oxazole

LiHMDS (1.0 M in THF, 26 mL, 26 mmol) was added dropwise to a solution of Example 43A (5.75 g, 23.8 mmol) in THF (100 mL) at −78° C. After 30 min solid hexachloroethane (6.21 g, 26.2 mmol) was added in one portion, and the reaction mixture was allowed to proceed for 18 hr with gradual warming to ambient temperature. The reaction was quenched with saturated aq NH$_4$Cl solution (50 mL), and the mixture was partitioned between H$_2$O and Et$_2$O. The aqueous phase was extracted once with Et$_2$O, and the combined organic extract was washed with brine, dried (Na$_2$SO$_4$), filtered, and concentrated in vacuo. The crude product was purified on silica gel (Analogix® Intelliflash 280™; SF40-150 g column; 100% hexane 7 min, then 0% to 20% EtOAc/hexanes eluant, 23 min) which yielded 6.23 g (95%) of the title compound as a pale yellow oil. $^1$H NMR (300 MHz, DMSO-d$_6$) δ 7.87 (d, J=8.5, 2H), 7.79 (d, J=8.5, 2H), 2.77 (q, J=7.5, 2H), 1.23 (t, J=7.5, 3H). MS (DCI$^+$) m/z 276 (M+H).

Example 43C (R)-8-(4-ethyl-5-(4-(trifluoromethyl)phenyl)oxazol-2-ylamino)-1,2,3,4-tetrahydronaphthalen-2-ol A mixture of Example 24E (3.69 g, 22.6 mmol) and Example 43B (6.23 g, 22.6 mmol) in BuOH (75 mL) was heated at 110° C. for 2 hr. p-Toluenesulfonic acid monohydrate (0.430 g, 2.26 mmol) was then added and heating was continued for 1.5 hr. The reaction mixture was cooled to ambient temperature, diluted with EtOAc, and quenched with aq saturated NaHCO$_3$ solution. The separated organic phase was washed with saturated NaHCO$_3$ solution and brine, dried (Na$_2$SO$_4$), filtered, and concentrated in vacuo to approximately 50 mL. Hexanes (70 mL) was added to precipitate the product, which was collected by vacuum filtration, washed with Et$_2$O:hexanes (1:1), and dried under vacuum at ambient temperature overnight. The result was 5.63 g (62%) of the title compound as a white solid. $^1$H NMR (300 MHz, DMSO-d$_6$) δ 9.21 (s, 1H), 7.77 (d, J=8.4, 2H), 7.64 (d, J=8.3, 2H), 7.55 (d, J=7.0, 1H), 7.11 (t, J=7.8, 1H), 6.86 (d, J=7.0, 1H), 4.79 (d, J=3.9, 1H), 3.99-3.86 (m, 1H), 2.99-2.82 (m, 2H), 2.80-2.67 (m, 1H), 2.70 (q, J=7.5, 2H), 2.56-2.44 (m, 1H), 1.93-1.81 (m, 1H), 1.69-1.54 (m, 1H), 1.22 (t, J=7.5, 3H). MS (ESI$^+$) m/z 403 (M+H).

Example 44

8-{[5-(5-bromopyridin-2-yl)-4-ethyl-1,3-oxazol-2-yl]amino}-1,2,3,4-tetrahydronaphthalen-2-ol

Example 44A 5-(5-bromopyridin-2-yl)-4-ethyloxazole

A mixture of 1-(1-isocyanopropylsulfonyl)-4-methylbenzene (1.98 g, 8.87 mmol), 5-bromopicolinaldehyde (1.65 g, 8.87 mmol), and $K_2CO_3$ (1.47 g, 10.6 mmol) in MeOH (45 mL) was heated at reflux overnight. The reaction was cooled to ambient temperature and concentrated in vacuo. Water was added to the residue and the product was extracted with EtOAc. The combined organic extract was washed with brine, dried ($Na_2SO_4$), filtered, and concentrated in vacuo. The crude product was chromatographed on silica gel (Analogix® 25×60 column, 10%-50% EtOAc/hexanes) to yield 1.97 g (88%) of the title compound. $^1$H NMR (300 MHz, $CDCl_3$) δ 8.68 (dd, J=2.4, 0.5, 1H), 7.89-7.82 (m, 2H), 7.55-7.49 (m, 1H), 3.06 (q, J=7.5, 2H), 1.29 (t, J=7.5, 3H). MS ($DCI^+$) m/z 253/255 (M+H).

Example 44B 5-(5-bromopyridin-2-yl)-2-chloro-4-ethyloxazole

LiHMDS (1.0 M in THF, 8.5 mL, 8.5 mmol) was added dropwise to a solution of Example 44A (1.97 g, 7.78 mmol) in THF (26 mL) at −78° C. After 30 min solid hexachloroethane (1.84 g, 7.78 mmol) was added in one portion and the reaction mixture was stirred while warming to ambient temperature overnight. The reaction was diluted with water and extracted with EtOAc. The organic extract was washed with water and brine, dried over $Na_2SO_4$, filtered, and concentrated in vacuo. Chromatography on silica gel (Analogix® Intelliflash 280™; SF25-120 g column; 100% hexane 0-5 min, then 0% to 25% EtOAc/hexanes eluant, 5-40 min) afforded 1.99 g (89%) of the title compound as a yellow oil that solidified on standing. $^1$H NMR (300 MHz, $CDCl_3$) δ 8.67 (dd, J=2.4, 0.6, 1H), 7.86 (dd, J=8.5, 2.4, 1H), 7.47 (dd, J=8.5, 0.6, 1H), 3.02 (q, J=7.5, 2H), 1.27 (t, J=7.5, 3H). MS ($DCI^+$) m/z 287/289 (M+H).

Example 44C 8-(5-(5-bromopyridin-2-yl)-4-ethyloxazol-2-ylamino)-1,2,3,4-tetrahydronaphthalen-2-ol A mixture of Example 24A (0.401 g, 2.46 mmol) and Example 44B (0.777 g, 2.70 mmol) in BuOH (10 mL) was heated at reflux for 3 hr. The solvent was evaporated at reduced pressure and the residue was dissolved in $CH_2Cl_2$/EtOAc. The organic solution was washed with saturated $NaHCO_3$ solution resulting in the formation of a yellow precipitate. The solid was collected by filtration, washed with $Et_2O$, and air-dried. The result was 392 mg (39%) of the title compound. $^1$H NMR (300 MHz, $CH_3OH-d_4$) δ 8.59 (dd, J=2.4, 0.7, 1H), 7.91 (dd, J=8.7, 2.4, 1H), 7.42-7.36 (m, 2H), 7.15 (t, J=7.8, 1H), 6.97 (d, J=7.6, 1H), 4.13-4.01 (m, 1H), 3.10-2.77 (m, J=7.5, 3H), 2.92 (q, J=7.5, 2H), 2.60 (dd, J=16.6, 7.9, 1H), 2.08-1.96 (m, 1H), 1.83-1.68 (m, 1H), 1.21 (t, J=7.5, 3H). MS ($ESI^+$) m/z 414/416 (M+H).

Example 45

8-({5-[3-chloro-4-(trifluoromethyl)phenyl]-4-methyl-1,3-oxazol-2-yl}amino)-1,2,3,4-tetrahydronaphthalen-2-ol

Example 45A 3-chloro-4-(trifluoromethyl)benzaldehyde

Diisobutylaluminum hydride (1.0 M in toluene, 28 mL, 28 mmol) was added slowly via syringe to a solution of 3-chloro-4-(trifluoromethyl)benzonitrile (3.79 g, 18.4 mmol) in THF (50 mL) at 0° C. The reaction was allowed to proceed for 2 hr, then warmed to ambient temperature and stirred an additional 2 hr. The reaction was then cooled to 0° C., and quenched with 3 M aq HCl (75 mL). The mixture was allowed to warm to ambient temperature, and stirred vigorously for 1.5 hr. The mixture was then transferred to a separatory funnel and diluted with $Et_2O$. The separated organic phase was dried over $Na_2SO_4$, filtered, and concentrated in vacuo. Flash chromatography (Analogix® Intelliflash 280™; 15% EtOAc/hexanes eluant; SF40-150 g column) yielded 2.84 g (74%) of the title compound as a colorless oil. $^1$H NMR (300 MHz, DMSO-$d_6$) δ 10.09 (s, 1H), 8.21 (s, 1H), 8.12 (d, J=8.1, 1H), 8.07-8.02 (m, 1H).

Example 45B 5-(3-chloro-4-(trifluoromethyl)phenyl)-4-methyloxazole

A mixture of Example 45A (2.84 g, 13.6 mmol), 1-(1-isocyanoethylsulfonyl)-4-methylbenzene (2.85 g, 13.6 mmol), and $K_2CO_3$ (2.26 g, 16.3 mmol) in MeOH (70 mL) was heated to reflux. After 2 hr the reaction mixture was cooled to ambient temperature, and the volatiles were evaporated at reduced pressure. The residue was partitioned between $Et_2O$ and $H_2O$. The separated aqueous layer was extracted with $Et_2O$, and the combined organic phase was washed with brine, dried ($Na_2SO_4$), filtered, and concentrated in vacuo. Flash chromatography (Analogix® Intelliflash 280; 10% to 30% EtOAc/hexanes eluant; SF40-150 g column) yielded 3.04 g (85%) of the title compound as a white solid. $^1$H NMR (300 MHz, DMSO-$d_6$) δ 8.48 (s, 1H), 7.96 (d, J=8.4, 1H), 7.87 (s, 1H), 7.78 (dd, J=8.3, 0.8, 1H), 2.43 (s, 3H). MS ($DCI^+$) m/z 262 (M+H).

Example 45C 2-chloro-5-(3-chloro-4-(trifluoromethyl)phenyl)-4-methyloxazole

LiHMDS (1.0 M in THF, 13 ml, 13 mmol) was added slowly via syringe to a solution of Example 45B (3.04 g, 11.6 mmol) in THF (50 mL) at −78° C. The solution was stirred 45 min, and then solid hexachloroethane (4.13 g, 17.4 mmol) was added in one portion. The reaction was allowed to proceed for 12 hr with gradual warming to ambient temperature. The reaction was quenched with half-saturated aq $NH_4Cl$ solution, and the product was extracted with $Et_2O$. The combined organic extract was washed with brine, dried ($Na_2SO_4$), filtered, and concentrated in vacuo. The crude product was purified by flash chromatography (Analogix® Intelliflash 280™; 0% to 20% EtOAc/hexanes eluant; SF40-150 g column) to afford 3.02 g (88%) of the title compound as a white solid. $^1$H NMR (300 MHz, DMSO-d$_6$) δ 7.97 (d, J=8.4, 1H), 7.86 (s, 1H), 7.75 (d, J=8.3, 1H), 2.42 (s, 3H). MS (DCI$^+$) m/z 296 (M+H).

Example 45D 8-(5-(3-chloro-4-(trifluoromethyl)phenyl)-4-methyloxazol-2-ylamino)-1,2,3,4-tetrahydronaphthalen-2-ol A mixture of Example 24A (136 mg, 0.834 mmol) and Example 45C (247 mg, 0.834 mmol) in BuOH (3.5 mL) was heated to 110° C. After 1 hr the solution was cooled to ambient temperature, diluted with EtOAc, and washed with saturated aq NaHCO$_3$ solution and brine, dried (Na$_2$SO$_4$), filtered, and concentrated to approximately 2 mL during which the product precipitatee. Hexanes (10-15 mL) was added to complete the product precipitation, which was collected by vacuum filtration. The solid was washed with hexanes and minimal Et$_2$O, and dried under vacuum at 50° C. overnight to provide 224 mg (64%) of the title compound as a light grey solid. $^1$H NMR (300 MHz, DMSO-d$_6$) δ 9.29 (s, 1H), 7.88 (d, J=8.5, 1H), 7.64 (s, 1H), 7.61-7.52 (m, 2H), 7.11 (t, J=7.8, 1H), 6.88 (d, J=7.4, 1H), 4.80 (d, J=4.0, 1H), 3.99-3.86 (m, 1H), 2.99-2.82 (m, 2H), 2.80-2.66 (m, 1H), 2.56-2.44 (m, 1H), 2.34 (s, 3H), 1.94-1.81 (m, 1H), 1.69-1.54 (m, 1H). MS (ESI$^+$) m/z 423 (M+H).

Example 46

8-({4-ethyl-5-[2-fluoro-4-(trifluoromethyl)phenyl]-1,3-oxazol-2-yl}amino)-1,2,3,4-tetrahydronaphthalen-2-ol

Example 46A 4-ethyl-5-(2-fluoro-4-(trifluoromethyl)phenyl)oxazole

A mixture of 1-(1-isocyanopropylsulfonyl)-4-methylbenzene (1.55 g, 6.94 mmol), 2-fluoro-4-(trifluoromethyl)benzaldehyde (0.95 mL, 6.9 mmol), and K$_2$CO$_3$ (1.15 g, 8.33 mmol) in MeOH (35 mL) was heated at reflux overnight. The reaction was cooled to ambient temperature and the volatiles evaporated at reduced pressure. The residue was diluted with water and the product extracted with EtOAc. The combined organic extract was washed with water and brine, dried (Na$_2$SO$_4$), filtered, and concentrated in vacuo. The crude product was chromatographed on silica gel (Analogix® 40×150 column, 10%-70% EtOAc/hexanes) to yield 0.89 g (50%) of the title compound. $^1$H NMR (300 MHz, CDCl$_3$) δ 7.95 (s, 1H), 7.67-7.60 (m, 1H), 7.53-7.48 (m, 1H), 7.47-7.42 (m, 1H), 2.67 (qd, J=7.5, 1.6, 2H), 1.29 (t, J=7.5, 3H). MS (DCI$^+$) m/z 260 (M+H).

Example 46B 2-chloro-4-ethyl-5-(2-fluoro-4-(trifluoromethyl)phenyl)oxazole

LiHMDS (1.0 M in THF, 6.1 mL, 6.1 mmol) was added to Example 46A (1.44 g, 5.56 mmol) in THF (19 mL) at −78° C. After 30 min solid hexachloroethane (1.32 g, 5.56 mmol) was added in one portion and the reaction mixture was stirred while warming to ambient temperature overnight. The reaction was then diluted with water and the product was extracted with EtOAc. The organic extract was washed with water and brine, dried (Na$_2$SO$_4$), filtered, and concentrated in vacuo. The crude product was chromatographed on silica gel (Analogix® 25×80 column, 0-5 min 100% hexanes; 5-40 min 0%-40% EtOAc/hexanes) to yield 460 mg (28%) of the title compound as a yellow oil that solidified on standing. $^1$H NMR (300 MHz, CDCl$_3$) δ 7.65-7.55 (m, 1H), 7.54-7.41 (m, 2H), 2.62 (qd, J=7.5, 1.7, 2H), 1.27 (t, J=7.5, 3H). MS (DCI$^+$) m/z 294 (M+H).

Example 46C 8-(4-ethyl-5-(2-fluoro-4-(trifluoromethyl)phenyl)oxazol-2-ylamino)-1,2,3,4-tetrahydronaphthalen-2-ol Example 24A (0.207 g, 1.27 mmol) and Example 46B (0.410 g, 1.40 mmol) were taken up in BuOH (5 mL), followed by addition of 1 drop of trifluoroacetic acid. The reaction was heated at 11 0° C. for several hr, and then 1 drop of concentrated HCl was added. After heating at 11 0° C. an additional 3 hrs the reaction mixture was cooled to ambient temperature and concentrated in vacuo. The residue was triturated with EtOAc and the solid filtered. The filtrate was then concentrated in vacuo and the residue was sonicated with Et$_2$O, and the resulting solid was collected by filtration to afford 172 mg (32%) of the title compound as a white solid. $^1$H NMR (300 MHz, CH$_3$OH-d$_4$) δ 7.72-7.63 (m, 1H), 7.59-7.50 (m, 2H), 7.41 (d, J=7.9, 1H), 7.14 (t, J=7.8, 1H), 6.95 (d, J=7.6, 1H), 4.12-4.01 (m, 1H), 3.10-2.92 (m, 2H), 2.91-2.77 (m, 1H), 2.66-2.49 (m, 3H), 2.08-1.96 (m, 1H), 1.83-1.68 (m, 1H), 1.22 (t, J=7.5, 3H). MS (ESI$^+$) m/z 421 (M+H).

Example 47

8-{[5-(4-bromophenyl)-4-ethyl-1,3-oxazol-2-yl]amino}-1,2,3,4-tetrahydronaphthalen-2-ol

Example 47A 5-(4-bromophenyl)-4-ethyloxazole

A mixture of 1-(1-isocyanopropylsulfonyl)-4-methylbenzene (1.21 g, 5.40 mmol), 4-bromobenzaldehyde (1 g, 5 mmol), and K$_2$CO$_3$ (0.896 g, 6.49 mmol) in MeOH (27 mL) was heated at reflux overnight. The reaction was cooled to ambient temperature and the solvent was evaporated at reduced pressure. The residue was partitioned between water and EtOAc. The separated organic phase was washed with water and brine, dried (Na$_2$SO$_4$), filtered, and concentrated in vacuo. The crude product was dissolved in minimal toluene, loaded on silica gel, and eluted with 2 column volumes of hexane, then 10% to 50% EtOAc/hexanes. The result was 1.27 g (93%) of the title compound. $^1$H NMR (300 MHz, CDCl$_3$) δ 7.84 (s, 1H), 7.60-7.54 (m, 2H), 7.49-7.43 (m, 2H), 2.78 (q, J=7.5, 2H), 1.32 (t, J=7.6, 3H). MS (DCI$^+$) m/z 252/254 (M+H).

Example 47B 5-(4-bromophenyl)-2-chloro-4-ethyloxazole

LiHMDS (1.0 M in THF, 5.5 mL, 5.5 mmol) was added to Example 47A (1.27 g, 5.04 mmol) in THF (17 mL) at −78° C. After 30 min solid hexachloroethane (1.19 g, 5.04 mmol) was added in one portion and the reaction mixture was stirred while warming to ambient temperature overnight. The reaction was then diluted with water and the product was extracted with EtOAc. The organic extract was washed with water and brine, dried (Na$_2$SO$_4$), filtered, and concentrated in vacuo. The crude product was chromatographed on silica gel (Analogix® 25×60 column, 0-3 min 100% hexanes; 3-30 min 5%-40% EtOAc/hexanes) to yield 1.22 g (85%) of the title compound as a yellow oil that solidified on standing. $^1$H NMR (300 MHz, CDCl$_3$) δ 7.59-7.54 (m, 2H), 7.43-7.37 (m, 2H), 2.72 (q, J=7.5, 2H), 1.29 (t, J=7.4, 3H). MS (DCI$^+$) m/z 286/288 (M+H).

Example 47C 8-(5-(4-bromophenyl)-4-ethyloxazol-2-ylamino)-1,2,3,4-tetrahydronaphthalen-2-ol A mixture of Example 24A (0.627 g, 3.84 mmol) and Example 47B (1.21 g, 4.22 mmol) in BuOH (15 mL) was heated at 110° C. for 2.5 hr. The reaction was cooled to ambient temperature and the solvent evaporated. The resulting solid was dissolved in EtOAc/CH$_2$Cl$_2$ and washed with saturated NaHCO$_3$ solution and water, washed with brine and dried over Na$_2$SO$_4$, filtered, and concentrated in vacuo until a slurry formed. Et$_2$O was added and the solid collected by filtration. The solid was then triturated with Et$_2$O/EtOAc (9:1), collected by filtration and air-dried to yield 475 mg (30%) of the title compound. $^1$H NMR (300 MHz, DMSO-d$_6$) δ 9.08 (s, 1H), 7.65-7.59 (m, 2H), 7.56 (d, J=8.0, 1H), 7.43-7.36 (m, 2H), 7.10 (t, J=7.8, 1H), 6.84 (d, J=7.4, 1H), 4.79 (d, J=3.9, 1H), 3.98-3.85 (m, 1H), 2.99-2.80 (m, 2H), 2.80-2.69 (m, 1H), 2.63 (q, J=7.5, 2H), 2.55-2.42 (m, 1H), 1.93-1.79 (m, 1H), 1.68-1.52 (m, 1H), 1.20 (t, J=7.5, 3H). MS (ESI$^+$) m/z 413/415 (M+H).

Example 48

(2R)-8-({4-ethyl-5-[2-fluoro-4-(trifluoromethyl)phenyl]-1,3-oxazol-2-yl}amino)-1,2,3,4-tetrahydronaphthalen-2-ol Example 46C (140 mg) was dissolved in methanol and loaded on a Chiralpak AD (21.1 mm×250 mm) preparative chiral HPLC column (1.5 mL/injection, 35 mg/mL), and eluted in supercritical CO$_2$ (100 bar) with methanol as the modifier (gradient: 10% for 1 min, ramp 2.8%/min to 50%, hold 4 min) under supercritical fluid chromatography (SFC) conditions at 35° C. with a flow rate of 40 mL/min. Pure fractions of the early eluting peak were pooled and the solvent evaporated to afford the title compound (30 mg) as a white solid. Analytical chiral HPLC (Chiralpak AD-H 4.6 mm×25 mm, methanol (gradient: 5% for 1 min, ramp 5.7%/min to 50%, total runtime 10 min) in supercritical CO$_2$ (100 bar), 35° C., 4 mL/min) showed the isolated material to be in >99% ee. $^1$H NMR (300 MHz, DMSO-d$_6$) δ 9.23 (s, 1H), 7.78 (d, J=10.6, 1H), 7.73-7.62 (m, 2H), 7.51 (d, J=7.9, 1H), 7.10 (t, J=7.8, 1H), 6.86 (d, J=7.3, 1H), 4.79 (d, J=3.9, 1H), 3.98-3.85 (m, 1H), 3.00-2.81 (m, 2H), 2.80-2.66 (m, 1H), 2.58-2.43 (m, 3H), 1.92-1.80 (m, 1H), 1.69-1.52 (m, 1H), 1.18 (t, J=7.4, 3H). MS (ESI$^+$) m/z 421 (M+H).

Example 49

(2S)-8-({4-ethyl-5-[2-fluoro-4-(trifluoromethyl)phenyl]-1,3-oxazol-2-yl}amino)-1,2,3,4-tetrahydronaphthalen-2-ol Example 46C (140 mg) was dissolved in methanol and loaded on a Chiralpak AD (21.1 mm×250 mm) preparative chiral HPLC column (1.5 mL/injection, 35 mg/mL), and eluted in supercritical CO$_2$ (100 bar) with methanol as the modifier (gradient: 10% for 1 min, ramp 2.8%/min to 50%, hold 4 min) under supercritical fluid chromatography (SFC) conditions at 35° C. with a flow rate of 40 mL/min. Pure fractions of the late eluting peak were pooled and the solvent evaporated to afford the title compound (30 mg) as a white solid. Analytical chiral HPLC (Chiralpak AD-H 4.6 mm×25 mm, methanol (gradient: 5% for 1 min, ramp 5.7%/min to 50%, total runtime 10 min) in supercritical CO$_2$ (100 bar), 35° C., 4 mL/min) showed the isolated material to be in >97% ee. $^1$H NMR (300 MHz, DMSO-d$_6$) δ 9.24 (s, 1H), 7.78 (d, J=10.7, 1H), 7.73-7.61 (m, 2H), 7.52 (d, J=7.4, 1H), 7.10 (t, J=7.8, 1H), 6.86 (d, J=7.5, 1H), 4.79 (d, J=3.9, 1H), 3.99-3.84 (m, 1H), 3.00-2.81 (m, 2H), 2.80-2.66 (m, 1H), 2.60-2.41 (m, 3H), 1.93-1.81 (m, 1H), 1.69-1.53 (m, 1H), 1.18 (t, J=7.7, 3H). MS (ESI$^+$) m/z 421 (M+H).

Example 50

(2S)-8-({4-ethyl-5-[4-(trifluoromethyl)phenyl]-1,3-oxazol-2-yl}amino)-1,2,3,4-tetrahydronaphthalen-2-ol A mixture of Example 25B (2.22 g, 13.6 mmol), Example 43B (3.75 g, 13.6 mmol), and p-toluenesulfonic acid (0.129 g, 0.680 mmol) in BuOH (45 mL) was heated at 110° C. for 2 hr. The reaction was cooled to ambient temperature, diluted with ethyl acetate, and washed with saturated NaHCO$_3$ solution and water, washed with brine and dried over Na$_2$SO$_4$, filtered, and concentrated in vacuo to a volume of approximately 25 mL resulting in a thick slurry. The mixture was dilute with 1:1 ether/hexanes and sonicated. The solid was collected by filtration, washed with 1:1 ether/hexanes and air-dried to afford 2.83 g (52%) of the title compound as an off-white solid. $^1$H NMR (300 MHz, DMSO-d$_6$) δ 9.21 (s, 1H), 7.78 (d, J=8.4, 2H), 7.64 (d, J=8.3, 2H), 7.56 (d, J=7.9, 1H), 7.11 (t, J=7.8, 1H), 6.86 (d, J=7.4, 1H), 4.80 (d, J=3.9, 1H), 3.99-3.86 (m, 1H), 3.00-2.81 (m, 2H), 2.80-2.70 (m, 1H), 2.70 (q, J=7.5, 2H), 2.57-2.43 (m, 1H), 1.93-1.80 (m, 1H), 1.69-1.53 (m, 1H), 1.22 (t, J=7.5, 3H). MS (DCI$^+$) m/z 403 (M+H). [□]$_D$=−4.2° (c 1, MeOH).

Example 51

5-({4-methyl-5-[4-(trifluoromethyl)phenyl]-1,3-oxazol-2-yl}amino)chroman-3-ol

Example 51A 2-allyl-3-bromophenol

A mixture of 1-(allyloxy)-3-bromobenzene (3.53 g, 16.6 mmol) and Et$_2$NPh (7.4 mL) was heated in a 220° C. oil bath. After 5 hr, the reaction mixture was cooled to room temperature, diluted with EtOAc (80 mL), and washed with 2N aq HCl (3×20 mL), water (2×20 mL), brine (10 mL), dried over Na$_2$SO$_4$, filtered, and concentrated in vacuo. Flash chromatography (0%-10% EtOAc/hexanes) gave 1.64 g (47%) of the title compound as the late eluting component, and 1.19 g (34%) of 2-allyl-5-bromophenol. $^1$HNMR (300 MHz, CDCl$_3$) δ 7.17 (dd, J=8.0, 1.1, 1H), 6.97 (t, J=8.0, 1H), 6.77 (dd, J=8.0, 1.0, 1H), 6.04-5.90 (m, 1H), 5.15 (t, J=1.7, 1H), 5.13-5.07 (m, 2H), 3.63 (dt, J=6.0, 1.6, 2H).

Example 51B 3-bromo-2-(oxiran-2-ylmethyl)phenyl acetate

A solution of Example 51A (500 mg, 2.35 mmol), triethylamine (0.50 mL, 3.52 mmol), and acetic anhydride (0.27 mL, 2.82 mmol) in CH$_2$Cl$_2$ (5 mL) was stirred at room temperature. After 2 hr the reaction mixture was diluted with CH$_2$Cl$_2$, washed with 2N aq HCl (2×10 mL) and saturated NaHCO$_3$ solution (10 mL), dried over Na$_2$SO$_4$, filtered, and concentrated in vacuo. The crude product (599 mg, 2.35 mmol) was dissolved in CHCl$_3$ (6 mL) and mCPBA (789 mg, 3.52 mmol) was added. The clear solution was heated in a 50° C. oil bath for 85 min. The reaction was cooled to room temperature, diluted with CH$_2$Cl$_2$, washed with saturated NaHCO$_3$ solution, dried over Na$_2$SO$_4$, filtered, and concentrated in vacuo. Flash chromatography (0%-50% EtOAc/hexanes) gave 615 mg (97%) of the title compound. $^1$H NMR (300 MHz, DMSO-d$_6$) δ 7.55 (dd, J=7.9, 1.1, 1H), 7.28 (t, J=8.0, 1H), 7.19 (dd, J=8.1, 1.3, 1H), 3.07-2.96 (m, 2H), 2.93-2.83 (m, 1H), 2.72-2.67 (m, 1H), 2.52-2.46 (m, 1H), 2.31 (s, 3H). MS (ESI$^+$) m/z 288/290 (M+NH$_4$).

Example 51C 5-bromochroman-3-yl acetate

A mixture of Example 51B (607 mg, 2.24 mmol) and sodium iodide (168 mg, 1.12 mmol) in acetone (3 mL) was heated to 55° C. After 2 h, the reaction mixture was cooled to room temperature and water and CH$_2$Cl$_2$ were added. The separated aqueous phase was extracted with CH$_2$Cl$_2$, and the combined organic extract was dried over Na$_2$SO$_4$, filtered, and concentrated in vacuo. Flash chromatography (0%-25% EtOAc/hexanes) gave 415 mg (68%) of the title compound as a clear oil. $^1$H NMR (300 MHz, DMSO-d$_6$) δ 7.20 (dd, J=7.9, 1.2, 1H), 7.09 (t, J=8.1, 1H), 6.86 (dd, J=8.2, 1.1, 1H), 5.28-5.21 (m, 1H), 4.22 (ddd, J=11.8, 3.5, 2.3, 1H), 4.15-4.07 (m, 1H), 3.06 (dd, J=17.8, 5.1, 1H), 2.75 (dt, J=17.8, 2.4, 1H), 2.01 (s, 3H).

Example 51D 5-(diphenylmethyleneamino)chroman-3-yl acetate

Example 51C (404 mg, 1.49 mmol), Pd(OAc)$_2$ (16.7 mg, 0.075 mmol), BINAP (186 mg, 0.298 mmol), and Cs$_2$CO$_3$ (1214 mg, 3.73 mmol) were combined in toluene (4 mL). While bubbling N$_2$ through the mixture for 10 min, benzophenone imine (0.50 mL, 2.98 mmol) was added and the red mixture was heated to 100° C. After 6 hr, the reaction mixture was cooled to ambient temperature, filtered, and the filter cake washed with CH$_2$Cl$_2$. The filtrate was concentrated in vacuo and the crude product was purified by flash chromatography (0%-25% EtOAc/hexanes) to yield 518 mg (94%) of the title compound. $^1$H NMR (300 MHz, DMSO-d$_6$) δ 7.77-7.62 (m, 2H), 7.61-7.43 (m, 3H), 7.36-7.28 (m, 3H), 7.18-7.08 (m, 2H), 6.81 (t, J=8.0, 1H), 6.36 (dd, J=8.2, 1.0, 1H), 6.03 (dd, J=7.8, 1.1, 1H), 5.20-5.12 (m, 1H), 4.18-3.96 (m, 2H), 2.89 (dd, J=17.5, 5.0, 1H), 2.62 (d, J=17.7, 1H), 2.00 (s, J=4.8, 3H). MS (ESI$^+$) m/z 372 (M+H).

Example 51E 5-aminochroman-3-ol

A solution of Example 51D (504 mg, 1.36 mmol) in THF (5 mL) was stirred at room temperature, followed by addition of 6N aq HCl (3.4 mL, 6.8 mmol). After 10 min water (20 mL) and CH$_2$Cl$_2$ (10 mL) were added and the layers separated. The aqueous layer was washed with CH$_2$Cl$_2$ (5 mL). The aqueous layer was then neutralized with saturated NaHCO$_3$ solution and extracted with CH$_2$Cl$_2$ (3×20 mL). The combined organic layers were dried (Na$_2$SO$_4$), filtered, and concentrated in vacuo. The residue was taken up in MeOH (5 mL) and K$_2$CO$_3$ (938 mg, 6.78 mmol) was added. After 20 min CH$_2$Cl$_2$ (50 mL) was added and the mixture was filtered and concentrated in vacuo. The crude product was purified by flash chromatography (50%-100% EtOAc/hexanes) to afford 145 mg (65%) of the title compound. $^1$H NMR (300 MHz, DMSO-d$_6$) δ 6.73 (t, J=8.0, 1H), 6.18 (dd, J=7.9, 1.1, 1H), 5.98 (dd, J=8.1, 1.0, 1H), 5.06 (d, J=4.2, 1H), 4.81 (bs, 2H), 4.01-3.92 (m, 2H), 3.63 (dd, J=11.0, 8.1, 1H), 2.64 (dd, J=16.9, 6.2, 1H), 2.23 (dd, J=16.1, 6.7, 1H). MS (ESI$^+$) m/z 166 (M+H).

Example 51F 5-(4-methyl-5-(4-(trifluoromethyl)phenyl)oxazol-2-ylamino)chroman-3-ol A solution of Example 51E (143 mg, 0.866 mmol), Example 12B (272 mg, 1.04 mmol), and p-toluenesulfonic acid monohydrate (21 mg, 0.1 1 mmol) in isopropanol (3.5 mL) was heated in a 60° C. oil bath for 20 min, then the temperature was increased to 80° C. After 4 hr, the reaction mixture was cooled to ambient temperature, diluted with CH$_2$Cl$_2$, and washed with saturated NaHCO$_3$ solution. The organic layer was dried (Na$_2$SO$_4$), filtered, and concentrated in vacuo to approximately 10 mL total volume upon which a white solid was observed to precipitate. Hexanes (~10 mL) was added, and the solid was collected by filtration, washed with 1:1 CH$_2$Cl$_2$/hexanes, and dried in a vacuum oven at 50° C. giving 215 mg product. The filtrate was purified by flash chromatography (50%-100% EtOAc/hexanes) giving an additional 15 mg product. The isolated solids were combined to afford 230 mg (68%) of the title compound as a white solid. $^1$H NMR (300 MHz, DMSO-d$_6$) δ 9.31 (s, 1H), 7.78 (d, J=8.5, 2H), 7.67 (d, J=8.3, 2H), 7.37 (dd, J=8.0, 1.0, 1H), 7.08 (t, J=8.1, 1H), 6.54 (dd, J=8.1, 0.9, 1H), 5.14 (d, J=3.9, 1H), 4.09-3.98 (m, 2H), 3.79 (dd, J=10.9, 7.4, 1H), 2.91 (dd, J=16.3, 5.0, 1H), 2.56 (dd, J=16.6, 6.3, 1H), 2.34 (s, 3H). MS (ESI$^+$) m/z 391 (M+H).

Example 52

(2S)-8-({4-(difluoromethyl)-5-[4-(trifluoromethyl)phenyl]-1,3-oxazol-2-yl}amino)-1,2,3,4-tetrahydronaphthalen-2-ol Example 52A Ethyl 5-(4-(trifluoromethyl)phenyl)oxazole-4-carboxylate Triethylamine (10.0 mL, 71.9 mmol) was added to a solution of 4-(trifluoromethyl)benzoyl chloride (5.0 g, 24.0 mmol) in THF (50 mL) at 0° C. Ethyl 2-isocyanoacetate (2.9 mL, 26.4 mmol) was added dropwise and the mixture was warmed to ambient temperature. After 3.5 days the reaction mixture was partitioned between EtOAc (100 mL) and H$_2$O (100 mL). The separated aqueous phase was extracted with EtOAc, and the combined organic layer was washed with brine, dried (Na$_2$SO$_4$), filtered, and concentrated in vacuo. Chromatography on silica gel (Analogix® Intelliflash 280™; SF40-150 g column; 20% to 50% EtOAc/hexanes eluant, 30 min) yielded 4.30 g (63%) of the title compound as a yellow solid. $^1$H NMR (300 MHz, DMSO-d$_6$) δ 8.66 (s, 1H), 8.18 (d, J=8.2, 2H), 7.92 (d, J=8.3, 2H), 4.31 (q, J=7.1, 2H), 1.28 (t, J=7.0, 3H). MS (DCI$^+$) m/z 286 (M+H).

Example 52B 5-(4-(trifluoromethyl)phenyl)oxazole-4-carbaldehyde

A solution of Example 52A (2.08 g, 7.29 mmol) in THF (20 mL) was cooled to −78° C. Diisobutylaluminum hydride (1.0 M in toluene, 14.6 mL, 14.6 mmol) was added slowly via syringe, and the reaction mixture was allowed to proceed 1 hr, then warmed to −20° C. After an additional 1 hr the reaction mixture was quenched with 1 N aq HCl, and the mixture was partitioned between Et$_2$O and saturated aq NH$_4$Cl solution. The separated aqueous phase was extracted with EtOAc, and the combined organic layer was washed with 3 N aq HCl and brine, dried (Na$_2$SO$_4$), filtered, and concentrated in vacuo. The crude product was purified on silica gel (Analogix® Intelliflash 280™; SF40-150 g column; 15% to 55% EtOAc/hexanes, 30 min) to give 1.26 g (72%) of the title compound as a pale yellow solid. $^1$H NMR (300 MHz, DMSO-d$_6$) δ 10.07 (s, 1H), 8.75 (s, 1H), 8.30 (d, J=8.1, 2H), 7.97 (d, J=8.2, 2H). MS (DCI$^+$) m/z 259 (M+NH$_4$).

Example 52C 4-(dimethoxymethyl)-5-(4-(trifluoromethyl)phenyl)oxazole

A solution of Example 52B (1.26 g, 5.22 mmol) in CH$_2$Cl$_2$ (5 mL) was cooled to −78° C. after which the starting material was observed to precipitate. Methoxytrimethylsilane (1.44 mL, 10.5 mmol) and trimethylsilyltrifluoromethane sulfonate (0.047 mL, 0.261 mmol) were added and the reaction mixture was allowed to proceed for 24 hr with gradual warming to ambient temperature. The reaction was quenched with saturated aq NaHCO$_3$ solution (10 mL), then diluted with EtOAc (50 mL) and H$_2$O (30 mL). The separated aqueous phase was extracted with EtOAc, and the combined organic extract was washed with brine, dried (Na$_2$SO$_4$), filtered, and concentrated in vacuo. The result was 1.42 g (95%) of the title compound as a yellow oil. $^1$H NMR (300 MHz, DMSO-d$_6$) δ 8.53 (s, 1H), 7.98 (d, J=8.7, 2H), 7.87 (d, J=8.4, 2H), 5.55 (s, 1H), 3.34 (s, 6H). MS (DCI$^+$) m/z 288 (M+H).

Example 52D 2-chloro-4-(dimethoxymethyl)-5-(4-(trifluoromethyl)phenyl)oxazole

LiHMDS (1.0 M in THF, 5.4 mL, 5.4 mmol) was added slowly to a solution of Example 52C (1.42 g, 4.94 mmol) in THF (20 mL) at −78° C. After 30 min solid hexachloroethane (1.29 g, 5.44 mmol) was added in one portion, and the reaction mixture was allowed to proceed for 5.5 hr with gradual warming to 5° C. The reaction was quenched with saturated aq NH$_4$Cl solution (10 mL), and the mixture was partitioned between H$_2$O and Et$_2$O. The aqueous phase was extracted once with Et$_2$O, and the combined organic extract was washed with brine, dried (Na$_2$SO$_4$), filtered, and concentrated in vacuo. The result was 1.83 g (115%) of the title compound as a dark yellow oil. $^1$H NMR (300 MHz, DMSO-d$_6$) δ 7.94 (d, J=8.5, 2H), 7.88 (d, J=8.8, 2H), 5.53 (s, 1H), 3.33 (s, 6H). MS (DCI$^+$) m/z 339 (M+NH$_4$).

Example 52E 2-chloro-5-(4-(trifluoromethyl)phenyl)oxazole-4-carbaldehyde

A mixture of Example 52D (1.59 g, 4.94 mmol) and oxalic acid (0.71 g, 7.9 mmol) in THF (16 mL)/water (8 mL) was stirred at ambient temperature for 2 hr. Additional oxalic acid (0.71 g, 7.9 mmol) and THF (16 mL) were added and the reaction mixture was stirred for 2 additional hr. HCl (4 N in dioxane, 5 mL) was then added and the reaction mixture was stirred 16 hr at ambient temperature, and then quenched by addition of saturated aq Na$_2$CO$_3$ solution (10 mL). The mixture was partitioned between Et$_2$O and H$_2$O, and the separated aqueous phase was extracted with Et$_2$O. The combined organic extract was washed with brine, dried (Na$_2$SO$_4$), filtered, and concentrated in vacuo. The crude product was purified on silica gel (Analogix® Intelliflash 280™; SF25-120 g column; 100% hexane 7 min, then 0% to 20% EtOAc/hexanes eluant, 23 min) which yielded 1.13 g (83%) of the title compound as a white solid. $^1$H NMR (300 MHz, DMSO-d$_6$) δ 9.98 (s, 1H), 8.27-8.21 (m, 2H), 7.97 (dd, J=9.0, 0.6, 2H). MS (DCI$^+$) m/z 293 (M+NH$_4$).

Example 52F 2-chloro-4-(difluoromethyl)-5-(4-(trifluoromethyl)phenyl)oxazole

To a solution of Example 52E (1.13 g, 4.10 mmol) in CH$_2$Cl$_2$ (12 mL) at 0° C. was added [bis(2-methoxyethyl)amino]sulfur trifluoride (1.1 mL, 6.2 mmol). The reaction was allowed to proceed for 3 hr, then H$_2$O (25 mL) was added and the phases were separated. The aqueous phase was extracted with CH$_2$Cl$_2$, and the combined organic phase was washed with brine, dried (Na$_2$SO$_4$), filtered, and concentrated in vacuo. Purification on silica gel (Analogix® Intelliflash 280™; SF25-80 g column; 5% EtOAc/hexanes eluant) afforded 1.04 g (85%) of the title compound as a colorless oil. $^1$H NMR (300 MHz, DMSO-d$_6$) δ 7.95 (d, J=8.5, 2H), 7.88 (d, J=8.5, 2H), 7.30 (t, J=52.5, 1H).

Example 52G (S)-8-(4-(difluoromethyl)-5-(4-(trifluoromethyl)phenyl)oxazol-2-ylamino)-1,2,3,4-tetrahydronaphthalen-2-ol A mixture of Example 25B (253 mg, 1.55 mmol), Example 52F (461 mg, 1.55 mmol), and p-toluenesulfonic acid monohydrate (29 mg, 0.16 mmol) in 2-propanol (5 mL) was heated at 100° C. for 1 hr, then the heat was increased to 120° C., and stirring was continued for 7 hr. The reaction was cooled to ambient temperature, diluted with EtOAc (30 mL), and washed with 1 N aq HCl, saturated aq NaHCO$_3$ solution, brine, dried (Na$_2$SO$_4$), filtered, and concentrated in vacuo to approximately 5 mL. Hexane (13 mL) was added slowly and the flask was swirled for 5 min. The resulting solid was collected by vacuum filtration, washed with hexane and minimal Et$_2$O, and dried in the vacuum oven at 50° C. for 30 min. This material was then chromatographed on silica gel (Analogix® Intelliflash 280™; SF25-80 g column; 50% to 70% EtOAc/hexanes eluant, 30 min; loaded w/EtOAc) which afforded 144 mg (22%) of the title compound as a white solid. $^1$H NMR (300 MHz, DMSO-d$_6$) δ 9.57 (s, 1H), 7.87 (d, J=8.5, 2H), 7.76 (d, J=8.3, 2H), 7.50 (d, J=7.9, 1H), 7.17 (t, J=52.8, 1H), 7.14 (t, J=7.8, 1H), 6.92 (d, J=7.5, 1H), 4.82 (d, J=3.9, 1H), 3.99-3.86 (m, 1H), 3.01-2.82 (m, 2H), 2.82-2.67 (m, 1H), 2.57-2.45 (m, 1H), 1.94-1.80 (m, 1H), 1.69-1.53 (m, 1H). MS (ESI$^+$) m/z 425 (M+H).

Example 53

(2R)-8-({4-(difluoromethyl)-5-[4-(trifluoromethyl) phenyl]-1,3-oxazol-2-yl}amino)-1,2,3,4-tetrahydronaphthalen-2-ol Example 24E (303 mg, 1.86 mmol), Example 52F (552 mg, 1.86 mmol), and p-toluenesulfonic acid monohydrate (35 mg, 0.18 mmol) were combined in BuOH (5 mL), and the reaction mixture was heated to 120° C. After 5 hr the mixture was cooled to ambient temperature, diluted with EtOAc, and washed with 1 M aq HCl and saturated aq NaHCO$_3$ solution. The separated organic phase was washed with brine, dried over Na$_2$SO$_4$, filtered, and concentrated in vacuo to a wet yellow solid. Hexane (~40 mL) was added and the solid was collected by filtration. The crude solid was purified by chromatography on silica gel (Analogix® Intelliflash 280™; SF25-80 g column; 50% to 70% EtOAc/hexanes eluant, 30 min) to afford 312 mg (40%) of the title compound as a white solid. $^1$H NMR (300 MHz, DMSO-d$_6$) δ 9.57 (s, 1H), 7.87 (d, J=8.5, 2H), 7.76 (d, J=8.2, 2H), 7.50 (d, J=7.9, 1H), 7.17 (t, J=52.8, 1H), 7.14 (t, J=7.8, 1H), 6.92 (d, J=7.5, 1H), 4.81 (d, J=3.9, 1H), 3.99-3.86 (m, 1H), 3.00-2.82 (m, 2H), 2.82-2.67 (m, 1H), 2.57-2.45 (m, 1H), 1.95-1.81 (m, 1H), 1.70-1.54 (m, 1H). MS (ESI$^+$) m/z 425 (M+H).

Example 54

(2R)-8-({5-[4-(difluoromethyl)phenyl]-4-ethyl-1,3-oxazol-2-yl}amino)-1,2,3,4-tetrahydronaphthalen-2-ol

Example 54A 5-(4-(difluoromethyl)phenyl)-4-ethyloxazole

A mixture of 1-(1-isocyanopropylsulfonyl)-4-methylbenzene (5.13 g, 22.9 mmol), Example 38C (3.59 g, 22.9 mmol), and K$_2$CO$_3$ (3.81 g, 27.6 mmol) in MeOH (115 mL) was heated at reflux overnight. The reaction was cooled to ambient temperature and the solvent evaporated. Water was added to the residue and the product was extracted with EtOAc. The combined organic extract was washed with brine, dried over Na$_2$SO$_4$, filtered, and concentrated in vacuo. The crude product was filtered through silica gel with Et$_2$O/EtOAc (1:1) as eluent to yield 4.96 g (97%) of the title compound as a light yellow oil. $^1$H NMR (300 MHz, CDCl$_3$) δ 7.86 (s, 1H), 7.69 (d, J=8.6, 2H), 7.58 (d, J=8.6, 2H), 6.67 (t, J=56.7, 1H), 2.82 (q, J=7.5, 2H), 1.34 (t, J=7.5, 3H). MS (DCI$^+$) m/z 224 (M+H).

Example 54B 2-chloro-5-(4-(difluoromethyl)phenyl)-4-ethyloxazole

LiHMDS (1.0 M in THF, 24 mL, 24 mmol) was added to a solution of Example 54A (4.90 g, 21.9 mmol) in THF (73 mL) at −78° C. The reaction was stirred at −78° C. for 30 min, and then solid hexachloroethane (5.20 g, 21.9 mmol) was added in one portion. The reaction was allowed to stir overnight while warming to room temperature. The reaction was quenched with water and the product extracted with EtOAc. The combined organic extract was washed with water and brine, and filtered through celite. The filtrate was dried over Na$_2$SO$_4$, filtered and concentrated in vacuo. The crude product was dissolved in toluene and loaded on silica gel (Analogix® 25×115 column), and eluted with 2 column lengths of hexanes then 5% to 50% EtOAc/hexanes. The result was 4.1 g (73%) of the title compound as a pale yellow oil. $^1$H NMR (300 MHz, CDCl$_3$) δ 7.63 (d, J=8.5, 2H), 7.58 (d, J=8.7, 2H), 6.68 (t, J=56.5, 1H), 2.77 (q, J=7.5, 2H), 1.31 (t, J=7.5, 3H). MS (DCI$^+$) m/z 258 (M+H).

Example 54C (R)-8-(5-(4-(difluoromethyl)phenyl)-4-ethyloxazol-2-ylamino)-1,2,3,4-tetrahydronaphthalen-2-ol A mixture of Example 24E (1.27 g, 7.76 mmol), Example 54B (2.00 g, 7.76 mmol), and p-toluenesulfonic acid monohydrate (0.074 g, 0.388 mmol) in BuOH (25 mL) was heated at 110° C. for 1.5 hr. The reaction was cooled to ambient temperature, and washed with saturated NaHCO$_3$ solution and water, and then brine during which a solid formed. The solid was collected by filtration, washed with water and hexane:Et$_2$O (1:1), and air-dried to yield 1.82 g (61%) of the title compound as an off-white solid. $^1$H NMR (300 MHz, DMSO-d$_6$) δ 9.13 (s, 1H), 7.66-7.53 (m, 5H), 7.11 (t, J=7.8, 1H), 7.04 (t, J=56.1, 1H), 6.85 (d, J=7.4, 1H), 4.80 (d, J=3.9, 1H), 3.99-3.86 (m, 1H), 2.99-2.81 (m, 2H), 2.80-2.68 (m, 1H), 2.68 (q, J=7.5, 2H), 2.56-2.43 (m, 1H), 1.94-1.79 (m, 1H), 1.69-1.53 (m, 1H), 1.21 (t, J=7.5, 3H). MS (ESI$^+$) m/z 385 (M+H).

Example 55

(2S)-8-({5-[4-(difluoromethyl)phenyl]-4-ethyl-1,3-oxazol-2-yl}amino)-1,2,3,4-tetrahydronaphthalen-2-ol A mixture of Example 25B (1.44 g, 8.81 mmol), Example 54B (2.27 g, 8.81 mmol), and p-toluenesulfonic acid monohydrate (0.084 g, 0.440 mmol) in BuOH (29 mL) was heated at 110° C. for 1.5 hours. The reaction was cooled to ambient temperature, and washed with saturated NaHCO$_3$ solution and water, and then brine during which a solid formed. The solid was collected by filtration, washed with water and hexane:Et$_2$O (1:1), and air-dried to provide 1.14 g (34%) of the title compound as an off-white solid. $^1$HNMR (300 MHz, DMSO-d$_6$) δ 9.14 (s, 1H), 7.65-7.54 (m, 5H), 7.10 (t, J=7.8, 1H), 7.04 (t, J=56.2, 1H), 6.85 (d, J=7.2, 1H), 4.80 (d, J=4.0, 1H), 3.99-3.86 (m, 1H), 2.99-2.80 (m, 2H), 2.80-2.69 (m, 1H), 2.71 (q, J=7.5, 2H), 2.56-2.44 (m, 1H), 1.93-1.81 (m, 1H), 1.69-1.53 (m, 1H), 1.21 (t, J=7.5, 3H). MS (ESI$^+$) m/z 385 (M+H).

Example 56

2-{[(7R)-7-hydroxy-5,6,7,8-tetrahydronaphthalen-1-yl]amino}-5-[4-(trifluoromethyl)phenyl]-1,3-oxazole-4-carbonitrile

Example 56A 5-(4-(trifluoromethyl)phenyl)oxazole

The title compound was prepared according to the procedure of Example 1B, substituting 4-(trifluoromethyl)benzaldehyde for 3-fluoro-4-(trifluoromethyl)benzaldehyde and substituting p-toluenesulfonylmethyl isocyanide for 1-(1-isocyanoethylsulfonyl)-4-methylbenzene.

Example 56B 4-bromo-5-(4-(trifluoromethyl)phenyl)oxazole

The title compound was prepared according to the procedure of Example 5B, substituting Example 56A for Example 5A

Example 56C 5-(4-(trifluoromethyl)phenyl)oxazole-4-carbonitrile

A mixture of Example 56B (500 mg, 1.71 mmol), dicyanozinc (221 mg, 1.88 mmol), and $Pd(Ph_3P)_4$ (101 mg, 0.087 mmol) in DMF (3 mL) was heated in a microwave reactor to 160° C. for 6 min. The reaction mixture was cooled to ambient temperature, diluted with water (50 mL) and extracted with EtOAc. The combined organic extracts were filtered through celite, and the filtrate was washed with water and brine, dried ($Na_2SO_4$), filtered, and concentrated in vacuo. An identical reaction was then performed using Example 56B (1.0 g, 3.4 mmol), dicyanozinc (442 mg, 3.77 mmol), and $Pd(Ph_3P)_4$ (198 mg, 0.171 mmol) in DMF (6 mL). The crude product from both reactions was combined and purified by chromatography on silica gel (25% EtOAc/hexanes) to afford 980 mg (80%) of the title compound as a white solid. $^1$H NMR (300 MHz, $CDCl_3$) δ 8.10 (dd, J=8.9, 0.7, 2H), 8.00 (s, 1H), 7.81 (dd, J=8.7, 0.5, 2H). MS ($DCI^+$) m/z 256 ($M+NH_4$).

Example 56D 2-chloro-5-(4-(trifluoromethyl)phenyl)oxazole-4-carbonitrile

LiHMDS (1.0 M in THF, 4.5 mL, 4.5 mmol) was added dropwise to a solution of Example 56C (0.980 g, 4.11 mmol) in THF (13 mL) at −78° C. After 30 min solid hexachloroethane (0.974 g, 4.11 mmol) was added in one portion. The reaction was allowed to warm to room temperature while stirring overnight during which a solid formed. The mixture was diluted with hexanes and water, and filtered. The filtrate was diluted with EtOAc, and the phases separated. The organic phase was washed with water and brine, dried ($Na_2SO_4$), filtered, and concentrated in vacuo. The crude product was dissolved in toluene, loaded on silica gel, and eluted with 1 column length of hexanes and then 0% to 30% EtOAc:hexanes to afford 0.51 g (46%) of the title compound as a yellow milky oil. $^1$H NMR (300 MHz, $CDCl_3$) δ 8.05 (d, J=8.2, 2H), 7.81 (d, J=8.3, 2H).

Example 56E (R)-2-(7-hydroxy-5,6,7,8-tetrahydronaphthalen-1-ylamino)-5-(4-(trifluoromethyl)phenyl)oxazole-4-carbonitrile A mixture of Example 24E (0.305 g, 1.87 mmol), Example 56D (0.51 g, 1.87 mmol), and p-toluenesulfonic acid monohydrate (0.018 g, 0.094 mmol) in isopropanol (6 mL) was heated at reflux for 2 hr. The reaction was cooled to ambient temperature, diluted with EtOAc, and washed with saturated $NaHCO_3$ solution and water, washed with brine and dried over $Na_2SO_4$, filtered, and concentrated in vacuo. The crude product was triturated with $Et_2O$. The resulting solid was collected by filtration, loaded on silica gel (Analogix® 25×40 column) and eluted with 10% MeOH/$CH_2Cl_2$ to afford 78 mg (10%) of the title compound as a white solid. $^1$H NMR (300 MHz, DMSO-$d_6$) δ 9.90 (s, 1H), 7.98 (d, J=8.6, 2H), 7.92 (d, J=8.5, 2H), 7.45 (d, J=7.0, 1H), 7.15 (t, J=7.8, 1H), 6.95 (d, J=7.0, 1H), 4.83 (d, J=4.0, 1H), 3.99-3.86 (m, 1H), 3.00-2.83 (m, 2H), 2.83-2.68 (m, 1H), 2.57-2.43 (m, 1H), 1.95-1.81 (m, 1H), 1.70-1.54 (m, 1H). MS ($DCI^+$) m/z 400 (M+H).

Example 57

(2R)-8-{[5-(5-bromopyridin-2-yl)-4-methyl-1,3-oxazol-2-yl]amino}-1,2,3,4-tetrahydronaphthalen-2-ol

Example 57A 5-(5-bromopyridin-2-yl)-4-methyloxazole

A mixture of 5-bromopicolinaldehyde (7.80 g, 41.9 mmol), 1-(1-isocyanoethylsulfonyl)-4-methylbenzene (8.78 g, 41.9 mmol), and $K_2CO_3$ (7.53 g, 54.5 mmol) in MeOH (150 mL) was heated at reflux for 3 hr. The reaction was then cooled to room temperature, the MeOH was evaporated at reduced pressure, and the crude material was partitioned between EtOAc and water. The separated aqueous layer was extracted twice with EtOAc. The combined organic extract was washed twice with water, dried over $Na_2SO_4$, filtered, and concentrated in vacuo. The crude material was chromatographed on silica gel (Analogix® SF65-600 column, 0% to 50% EtOAc/hexane) to afford 7.32 g (73%) of the title compound as a yellow solid. $^1$H NMR (300 MHz, DMSO-$d_6$) δ 8.78 (dd, J=2.4, 0.6, 1H), 8.44 (s, 1H), 8.15 (dd, J=8.5, 2.4, 1H), 7.64 (dd, J=8.5, 0.6, 1H), 2.50 (s, 3H). MS ($DCI^+$) m/z 239/241 (M+H).

Example 57B 5-(5-bromopyridin-2-yl)-2-chloro-4-methyloxazole

A solution of Example 57A (7.32 g, 30.6 mmol) in THF (150 mL) was cooled to −78° C., and treated carefully with LiHMDS (1 M in THF, 37 mL, 37 mmol). The mixture was stirred at −78° C. for 20 minutes, then was treated all at once with hexachloroethane (14.5 g, 61.2 mmol). The flask was removed from the cold bath, and the reaction mixture was stirred overnight at room temperature. After this time, the mixture was diluted with $Et_2O$ and washed with saturated $NH_4Cl$ solution and water, dried over $Na_2SO_4$, filtered, and concentrated in vacuo. The crude product was chromatographed on silica gel (100% hexane, then 0% to 20% EtOAc/hexane) to afford 7.44 g (89%) of the title compound as a pale yellow solid. $^1$H NMR (300 MHz, $CDCl_3$) δ 8.68 (d, J=2.4, 1H), 7.87 (dd, J=8.4, 2.4, 1H), 7.48 (dd, J=8.7, 0.7, 1H), 2.57 (s, 3H). MS ($DCI^+$) m/z 273/275 (M+H).

Example 57C 8-(5-(5-bromopyridin-2-yl)-4-methyloxazol-2-ylamino)-1,2,3,4-tetrahydronaphthalen-2-ol A mixture of Example 24A (3.58 g, 21.9 mmol) and Example 57B (6.0 g, 21.9 mmol) in BuOH (75 mL) was heated at 110° C. for 2 hr. The mixture was cooled to room temperature and diluted with EtOAc. The organic solution was washed three times with saturated $NaHCO_3$ solution and once with water and once with brine, dried over $Na_2SO_4$, filtered, and concentrated in vacuo. The crude product was triturated with hexane, and the solid was collected by filtration, washed with additional hexane, and air-dried to afford 6.86 g (78%) of the title compound. $^1$H NMR (300 MHz, DMSO-$d_6$) δ 9.26 (s, 1H), 8.65 (dd, J=2.4, 0.7, 1H), 8.05 (dd, J=8.7, 2.4, 1H), 7.53 (d, J=7.9, 1H), 7.33 (d, J=8.7, 1H), 7.11 (t, J=7.8, 1H), 6.87 (d, J=7.3, 1H), 4.80 (d, J=3.9, 1H), 3.99-3.85 (m, 1H), 2.99-2.82 (m, 2H), 2.81-2.66 (m, 1H), 2.56-2.43 (m, 1H), 2.41 (s, 3H), 1.94-1.80 (m, 1H), 1.70-1.53 (m, 1H). MS (ESI$^+$) m/z 400 (M+H).

Example 57D (R)-8-(5-(5-bromopyridin-2-yl)-4-methyloxazol-2-ylamino)-1,2,3,4-tetrahydronaphthalen-2-ol Example 57C (8.4 g) was dissolved in ethanol, loaded on a Chiralpak AD-H SFC (3 cm ID×25 cm) preparative chiral HPLC column (4.5 mL/injection), and eluted with 40% ethanol (containing 1% isopropylamine) in supercritical $CO_2$ (120 bar) under supercritical fluid chromatography (SFC) conditions at 40° C. with a flow rate of 40 gram/min. The early eluting peak was collected and the solvent evaporated to afford 1.98 g (24%) of the title compound as a brown solid. Analytical chiral HPLC (Chiralpak AD-H 4.6 mm ID×25 cm, 40% ethanol (w/1% isopropylamine) in supercritical $CO_2$ (200 bar), 40° C., 3 mL/min) showed the isolated material to have 100% ee. $^1$H NMR (300 MHz, DMSO-$d_6$) δ 9.30 (s, 1H), 8.66 (d, J=2.4, 1H), 8.06 (dd, J=8.6, 2.4, 1H), 7.53 (d, J=7.4, 1H), 7.33 (d, J=8.6, 1H), 7.11 (t, J=7.8, 1H), 6.87 (d, J=7.4, 1H), 4.83 (d, J=3.9, 1H), 4.00-3.83 (m, 1H), 3.01-2.81 (m, 2H), 2.80-2.66 (m, 1H), 2.56-2.44 (m, 1H), 2.41 (s, 3H), 1.94-1.80 (m, 1H), 1.70-1.51 (m, 1H). MS (ESI$^+$) m/z 400/402 (M+H). [□]$_D$=+6.7° (c 0.3, MeOH).

Example 58

(2R)-8-({5-[2,3-difluoro-4-(trifluoromethyl)phenyl]-4-methyl-1,3-oxazol-2-yl}amino)-1,2,3,4-tetrahydronaphthalen-2-ol Example 58A 5-(2,3-difluoro-4-(trifluoromethyl)phenyl)-4-methyloxazole A mixture of 1-(1-isocyanoethylsulfonyl)-4-methylbenzene (1 0.0 g, 47.8 mmol), 2,3-difluoro-4-(trifluoromethyl)benzaldehyde (9.68 g, 46.1 mmol), and $K_2CO_3$ (13.1 g, 95.0 mmol) in MeOH (240 mL) was heated to reflux. After 2 hr, the reaction mixture was cooled to ambient temperature, water (700 mL) was added, and the product was extracted with EtOAc (700 mL). The organic layer was washed with brine and dried over $Na_2SO_4$, filtered, and concentrated to an orange oil. The crude product was purified by chromatography on silica gel in five batches (Analogix® SF40-240G column, 100% $CH_2Cl_2$, 65 mL/min) to afford 7.22 g (60%) of the title compound as a light yellow liquid. $^1$H NMR (300 MHz, DMSO-$d_6$) δ 8.56 (s, 1H), 7.78-7.69 (m, 1H), 7.68-7.59 (m, 1H), 2.30 (d, J=2.5, 3H). MS (DCI$^+$) m/z 264 (M+H).

Example 58B 2-chloro-5-(2,3-difluoro-4-(trifluoromethyl)phenyl)-4-methyloxazole

Example 58A (7.22 g, 27.4 mmol) was dissolved in THF (130 mL) and cooled to −75° C. for 15 min. LiHMDS (1.0 M in THF, 36 mL, 36 mmol) was added in portions, and the orange solution was stirred at −75° C. for 30 min. Solid hexachloroethane (13.0 g, 54.9 mmol) was added, and the reaction mixture was stirred overnight while warming to ambient temperature. Water (500 mL) was added and the product was extracted with 1:1 EtOAc/hexanes (2×500 mL). The combined organic extract was washed with brine and dried over $Na_2SO_4$, filtered, and concentrated to an orange slurry. The crude product was chromatographed on silica gel (Analogix® SF65-200G column, 0%-15% EtOAc/hexanes, 75 mL/min) to yield 7.79 g (95%) of the title compound as a light yellow liquid. $^1$H NMR (300 MHz, DMSO-$d_6$) δ 7.79-7.71 (m, 1H), 7.68-7.59 (m, 1H), 2.28 (d, J=2.5, 3H). MS (DCI$^+$) m/z 298 (M+H).

Example 58C (2R)-8-(5-(2,3-difluoro-4-(trifluoromethyl)phenyl)-4-methyloxazol-2-ylamino)-1,2,3,4-tetrahydronaphthalen-2-ol A mixture of Example 24E (3.76 g, 23.0 mmol) and Example 58B (6.83 g, 22.9 mmol) in BuOH (115 mL) was heated at reflux for 70 min. The reaction was cooled to ambient temperature and combined with the reaction mixture from an identical reaction that employed Example 24E (494 mg, 3.03 mmol) and Example 58B (898 mg, 3.02 mmol) in BuOH (15 mL). The combined reaction mixture was diluted with EtOAc (700 mL), and washed with saturated $NaHCO_3$ solution, washed with brine and dried over $Na_2SO_4$, filtered, and concentrated to a brown solid. The crude product was purified by chromatography on silica gel in three batches (Analogix® SF40-150G column, 50%-100% EtOAc/$CH_2Cl_2$, 70 mL/min) to yield 7.80 g (71%) of the title compound as a beige solid. $^1$H NMR (300 MHz, DMSO-$d_6$) δ 9.35 (s, 1H), 7.71-7.60 (m, 1H), 7.52-7.43 (m, 2H), 7.11 (t, J=7.8, 1H), 6.88 (d, J=7.5, 1H), 4.80 (d, J=3.9, 1H), 3.98-3.84 (m, 1H), 3.00-2.81 (m, 2H), 2.80-2.65 (m, 1H), 2.56-2.43 (m, 1H), 2.21 (d, J=3.0, 3H), 1.94-1.79 (m, 1H), 1.70-1.52 (m, 1H). MS (ESI$^+$) m/z 425 (M+H). [□]$_D$=+4.8° (c 1.0, MeOH).

Example 59

(2R)-8-{[5-(4-bromophenyl)-4-ethyl-1,3-oxazol-2-yl]amino}-1,2,3,4-tetrahydronaphthalen-2-ol Example 47C (425 mg) was dissolved in methanol and loaded on a Chiralpak AD (21.1 mm×250 mm) preparative chiral HPLC column (1.5 mL/injection, 35 mg/mL), and eluted in supercritical $CO_2$ (100 bar) with methanol as the modifier (gradient: 10% for 1 min, ramp 4%/min to 50%, total runtime 20 min) under supercritical fluid chromatography (SFC) conditions at 35° C. with a flow rate of 40 mL/min. Pure fractions of the early eluting component were pooled and concentrated in vacuo to give 36 mg (17%) of the title compound as a white solid. Analytical chiral HPLC (Chiralpak AD-H 4.6 mm×25 mm, methanol (gradient: 5% for 1 min, ramp 5.7%/min to 50%, total runtime 10 min) in supercritical $CO_2$ (100 bar), 35° C., 4 mL/min) detected a single peak for the isolated material, (>99% ee). $^1$H NMR (300 MHz, DMSO-$d_6$) δ 9.07 (s, 1H), 7.67-7.59 (m, 2H), 7.56 (d, J=7.3, 1H), 7.44-7.36 (m, 2H), 7.10 (t, J=7.8, 1H), 6.84 (d, J=7.3, 1H), 4.79 (d, J=3.9, 1H), 3.99-3.85 (m, 1H), 2.99-2.81 (m, 2H), 2.81-2.67 (m, 1H), 2.63 (q, J=7.5, 2H), 2.55-2.42 (m, 1H), 1.93-1.80 (m, 1H), 1.70-1.51 (m, 1H), 1.20 (t, J=7.5, 3H). MS (ESI$^+$) m/z 413/415 (M+H).

Example 60

(2S)-8-{[5-(4-bromophenyl)-4-ethyl-1,3-oxazol-2-yl]amino}-1,2,3,4-tetrahydronaphthalen-2-ol Example 47C (425 mg) was dissolved in methanol and loaded on a Chiralpak AD (21.1 mm×250 mm) preparative chiral HPLC column (1.5 mL/injection, 35 mg/mL), and eluted in supercritical $CO_2$ (100 bar) with methanol as the modifier (gradient: 10% for 1 min, ramp 4%/min to 50%, total runtime 20 min) under supercritical fluid chromatography (SFC) conditions at 35° C. with a flow rate of 40 mL/min. Pure fractions of the late eluting component were pooled and concentrated in vacuo to give 36 mg (17%) of the title compound as a white solid. Analytical chiral HPLC (Chiralpak AD-H 4.6 mm×25 mm, methanol (gradient: 5% for 1 min, ramp 5.7%/min to 50%, total runtime 10 min) in supercritical $CO_2$ (100 bar), 35° C., 4 mL/min) detected a single peak for the isolated material, (>99% ee). $^1$H NMR (300 MHz, DMSO-$d_6$) δ 9.07 (s, 1H), 7.62 (d, J=8.6, 2H), 7.56 (d, J=7.7, 1H), 7.40 (d, J=8.6, 2H), 7.10 (t, J=7.8, 1H), 6.84 (d, J=7.4, 1H), 4.79 (d, J=3.9, 1H), 3.98-3.85 (m, 1H), 2.99-2.80 (m, 2H), 2.80-2.67 (m, 1H), 2.63 (q, J=7.4, 2H), 2.55-2.43 (m, 1H), 1.93-1.80 (m, 1H), 1.69-1.53 (m, 1H), 1.20 (t, J=7.5, 3H). MS (ESI$^+$) m/z 413/415 (M+H).

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I)

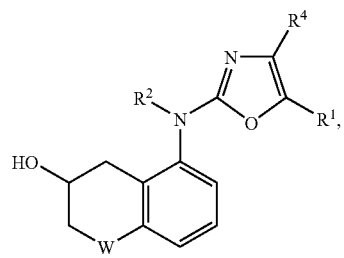

(I)

or a pharmaceutically acceptable salt, thereof, wherein
W is $CH_2$ or O;
$R^1$ is phenyl, a monocyclic heteroaryl, or a monocyclic cycloalkenyl, a monocyclic cycloalkyl, each of which is independently unsubstituted or substituted with 1, 2, 3, 4, or 5 substituents as represented by $R^3$, wherein each $R^3$ is independently alkyl, alkenyl, alkynyl, —$NO_2$, —CN, halogen, —$OR^a$, —$OC(O)R^a$, —$SR^a$, —$SF_5$, —$S(O)R^b$, —$S(O)_2R^b$, —$S(O)_2N(R^a)(R^c)$, —$N(R^a)(R^c)$, —$N(R^c)C(O)R^a$, —$N(R^c)S(O)_2R^b$, —$N(R^c)C(O)N(R^a)(R^c)$, —$N(R^c)S(O)_2N(R^a)(R^c)$, —$C(O)R^a$, —$C(O)O(R^a)$, —$C(O)N(R^a)(R^c)$, —$(CR^eR^f)_m$—CN, haloalkyl, or a monocyclic cycloalkyl that is optionally substituted with 1, 2, 3, or 4 substituents independently selected from the group consisting of alkyl, haloalkyl and halogen;
$R^a$, at each occurrence, is independently hydrogen, alkyl, or haloalkyl;
$R^b$, at each occurrence, is independently alkyl or haloalkyl;
$R^c$, at each occurrence, is independently hydrogen, alkyl, or haloalkyl;
$R^e$ and $R^f$ are each independently hydrogen, alkyl, or haloalkyl;
m is 1, 2, or 3;
$R^2$ is hydrogen or alkyl; and
$R^4$ is methyl, ethyl, $C_1$-$C_2$ haloalkyl, or —CN.

2. The compound according to claim 1 or a pharmaceutically acceptable salt thereof, wherein $R^2$ is hydrogen.

3. The compound according to claim 2 or a pharmaceutically acceptable salt thereof, wherein $R^1$ is optionally substituted phenyl.

4. The compound according to claim 2 or a pharmaceutically acceptable salt thereof, wherein $R^1$ is optionally substituted heteroaryl.

5. The compound according to claim 3 or a pharmaceutically acceptable salt thereof, wherein the phenyl is optionally substituted with 1, 2, or 3 substituents independently selected from the group consisting of alkyl, alkenyl, —CN, halogen, —$OR^a$, —$SF_5$, —$S(O)_2R^b$, haloalkyl, —$(CR^eR^f)_m$—CN, and an optionally substituted monocyclic cycloalkyl.

6. The compound according to claim 1 of formula (Ia) or a pharmaceutically acceptable salt thereof

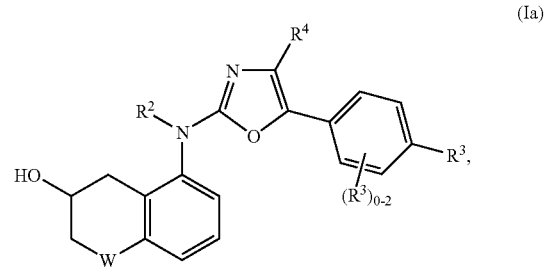

(Ia)

wherein W, $R^2$, $R^3$, and $R^4$ are as set forth in claim 1.

7. The compound according to claim 6 or a pharmaceutically acceptable salt thereof wherein $R^2$ is hydrogen.

8. The compound according to claim 7 or a pharmaceutically acceptable salt thereof wherein each $R^3$ is independently selected from the group consisting of alkyl, alkenyl, —CN, halogen, —$OR^a$, —$SF_5$, —$S(O)_2R^b$, haloalkyl, —$(CR^eR^f)_m$—CN, and an optionally substituted monocyclic cycloalkyl.

9. The compound according to claim 1 selected from the group consisting of
8-({5-[3-fluoro-4-(trifluoromethyl)phenyl]-4-methyl-1,3-oxazol-2-yl}amino)-1,2,3,4-tetrahydronaphthalen-2-ol;
8-({5-[3,4-bis(trifluoromethyl)phenyl]-4-methyl-1,3-oxazol-2-yl}amino)-1,2,3,4-tetrahydronaphthalen-2-ol;
8-({5-[2,4-bis(trifluoromethyl)phenyl]-4-methyl-1,3-oxazol-2-yl}amino)-1,2,3,4-tetrahydronaphthalen-2-ol;
8-({5-[2-methoxy-4-(trifluoromethyl)phenyl]-4-methyl-1,3-oxazol-2-yl}amino)-1,2,3,4-tetrahydronaphthalen-2-ol;
8-({5-[2-fluoro-4-(trifluoromethyl)phenyl]-4-methyl-1,3-oxazol-2-yl}amino)-1,2,3,4-tetrahydronaphthalen-2-ol;

8-({5-[2,3-difluoro-4-(trifluoromethyl)phenyl]-4-methyl-1,3-oxazol-2-yl}amino)-1,2,3,4-tetrahydronaphthalen-2-ol;
8-[(4-methyl-5-thien-3-yl-1,3-oxazol-2-yl)amino]-1,2,3,4-tetrahydronaphthalen-2-ol;
8-[(4-methyl-5-thien-2-yl-1,3-oxazol-2-yl)amino]-1,2,3,4-tetrahydronaphthalen-2-ol;
8-({4-methyl-5-[4-(trifluoromethoxy)phenyl]-1,3-oxazol-2-yl]amino}-1,2,3,4-tetrahydronaphthalen-2-ol;
8-{[5-(4-tert-butylphenyl)-4-methyl-1,3-oxazol-2-yl]amino}-1,2,3,4-tetrahydronaphthalen-2-ol;
8-{[4-methyl-5-(4-methylphenyl)-1,3-oxazol-2-yl]amino}-1,2,3,4-tetrahydronaphthalen-2-ol;
8-({4-methyl-5-[4-(trifluoromethyl)phenyl]-1,3-oxazol-2-yl]amino)-1,2,3,4-tetrahydronaphthalen-2-ol;
8-{[5-(4-chlorophenyl)-4-methyl-1,3-oxazol-2-yl]amino}-1,2,3,4-tetrahydronaphthalen-2-ol;
8-{[5-(4-methoxyphenyl)-4-methyl-1,3-oxazol-2-yl]amino}-1,2,3,4-tetrahydronaphthalen-2-ol;
4-{2-[(7-hydroxy-5,6,7,8-tetrahydronaphthalen-1-yl)amino]-4-methyl-1,3-oxazol-5-yl} benzonitrile;
8-{[5-(4-bromophenyl)-4-methyl-1,3-oxazol-2-yl]amino}-1,2,3,4-tetrahydronaphthalen-2-ol;
8-{[5-(3,4-dichlorophenyl)-4-methyl-1,3-oxazol-2-yl]amino}-1,2,3,4-tetrahydronaphthalen-2-ol;
8-{[5-(4-fluorophenyl)-4-methyl-1,3-oxazol-2-yl]amino}-1,2,3,4-tetrahydronaphthalen-2-ol;
8-{[5-(4-chloro-2-methylphenyl)-4-methyl-1,3-oxazol-2-yl]amino}-1,2,3,4-tetrahydronaphthalen-2-ol;
8-{[5-(4-bromo-2-fluorophenyl)-4-methyl-1,3-oxazol-2-yl]amino}-1,2,3,4-tetrahydronaphthalen-2-ol;
(2R)-8-({4-methyl-5-[4-(trifluoromethyl)phenyl]-1,3-oxazol-2-yl}amino)-1,2,3,4-tetrahydronaphthalen-2-ol;
(2S)-8-({4-methyl-5-[4-(trifluoromethyl)phenyl]-1,3-oxazol-2-yl}amino)-1,2,3,4-tetrahydronaphthalen-2-ol;
8-({4-methyl-5-[6-(trifluoromethyl)pyridin-3-yl]-1,3-oxazol-2-yl}amino)-1,2,3,4-tetrahydronaphthalen-2-ol;
(2R)-8-({5-[2-fluoro-4-(trifluoromethyl)phenyl]-4-methyl-1,3-oxazol-2-yl}amino)-1,2,3,4-tetrahydronaphthalen-2-ol;
(2S)-8-({5-[2-fluoro-4-(trifluoromethyl)phenyl]-4-methyl-1,3-oxazol-2-yl}amino)-1,2,3,4-tetrahydronaphthalen-2-ol;
8-{[5-(4-bromo-3-fluorophenyl)-4-methyl-1,3-oxazol-2-yl]amino}-1,2,3,4-tetrahydronaphthalen-2-ol;
8-{[5-(3-fluoro-4-methylphenyl)-4-methyl-1,3-oxazol-2-yl]amino}-1,2,3,4-tetrahydronaphthalen-2-ol;
8-({4-methyl-5-[5-(trifluoromethyl)-2-furyl]-1,3-oxazol-2-yl}amino)-1,2,3,4-tetrahydronaphthalen-2-ol;
8-({5-[(4R)-4-isopropenylcyclohex-1-en-1-yl]-4-methyl-1,3-oxazol-2-yl}amino)-1,2,3,4-tetrahydronaphthalen-2-ol;
8-{[5-(5-ethylthien-2-yl)-4-methyl-1,3-oxazol-2-yl]amino}-1,2,3,4-tetrahydronaphthalen-2-ol;
(2R)-8-({4-methyl-5-[5-(trifluoromethyl)pyridin-2-yl]-1,3-oxazol-2-yl}amino)-1,2,3,4-tetrahydronaphthalen-2-ol;
2-(4-{2-[(7-hydroxy-5,6,7,8-tetrahydronaphthalen-1-yl)amino]-4-methyl-1,3-oxazol-5-yl}phenyl)-2-methylpropanenitrile;
8-{[5-(4-cyclopropyl-3-fluorophenyl)-4-methyl-1,3-oxazol-2-yl]amino}-1,2,3,4-tetrahydronaphthalen-2-ol;
8-{[5-(4-chloro-3-fluorophenyl)-4-methyl-1,3-oxazol-2-yl]amino}-1,2,3,4-tetrahydronaphthalen-2-ol;
8-({5-[4-(difluoromethyl)phenyl]-4-methyl-1,3-oxazol-2-yl}amino)-1,2,3,4-tetrahydronaphthalen-2-ol;
(2R)-8-({5-[4-(difluoromethyl)phenyl]-4-methyl-1,3-oxazol-2-yl}amino)-1,2,3,4-tetrahydronaphthalen-2-ol;
8-({4-methyl-5-[4-(pentafluoro-lambda~6~sulfanyl)phenyl]-1,3-oxazol-2-yl}amino)-1,2,3,4-tetrahydronaphthalen-2-ol;
(2R)-8-{[5-(4-chloro-3-fluorophenyl)-4-methyl-1,3-oxazol-2-yl]amino}-1,2,3,4-tetrahydronaphthalen-2-ol;
(2R)-8-{[5-(4-bromo-3-fluorophenyl)-4-methyl-1,3-oxazol-2-yl]amino}-1,2,3,4-tetrahydronaphthalen-2-ol;
(2R)-8-({4-ethyl-5-[4-(trifluoromethyl)phenyl]-1,3-oxazol-2-yl}amino)-1,2,3,4-tetrahydronaphthalen-2-ol;
8-{[5-(5-bromopyridin-2-yl)-4-ethyl-1,3-oxazol-2-yl]amino}-1,2,3,4-tetrahydronaphthalen-2-ol;
8-({5-[3-chloro-4-(trifluoromethyl)phenyl]-4-methyl-1,3-oxazol-2-yl}amino)-1,2,3,4-tetrahydronaphthalen-2-ol;
8-({4-ethyl-5-[2-fluoro-4-(trifluoromethyl)phenyl]-1,3-oxazol-2-yl}amino)-1,2,3,4-tetrahydronaphthalen-2-ol;
8-{[5-(4-bromophenyl)-4-ethyl-1,3-oxazol-2-yl]amino}-1,2,3,4-tetrahydronaphthalen-2-ol;
(2R)-8-({4-ethyl-5-[2-fluoro-4-(trifluoromethyl)phenyl]-1,3-oxazol-2-yl}amino)-1,2,3,4-tetrahydronaphthalen-2-ol;
(2S)-8-({4-ethyl-5-[2-fluoro-4-(trifluoromethyl)phenyl]-1,3-oxazol-2-yl}amino)-1,2,3,4-tetrahydronaphthalen-2-ol;
(2S)-8-({4-ethyl-5-[4-(trifluoromethyl)phenyl]-1,3-oxazol-2-yl}amino)-1,2,3,4-tetrahydronaphthalen-2-ol;
5-({4-methyl-5-[4-(trifluoromethyl)phenyl]-1,3-oxazol-2-yl}amino)chroman-3-ol;
(2S)-8-({4-(difluoromethyl)-5-[4-(trifluoromethyl)phenyl]-1,3-oxazol-2-yl}amino)-1,2,3,4-tetrahydronaphthalen-2-ol;
(2R)-8-({4-(difluoromethyl)-5-[4-(trifluoromethyl)phenyl]-1,3-oxazol-2-yl}amino)-1,2,3,4-tetrahydronaphthalen-2-ol;
(2R)-8-({5-[4-(difluoromethyl)phenyl]-4-ethyl-1,3-oxazol-2-yl}amino)-1,2,3,4-tetrahydronaphthalen-2-ol;
(2S)-8-({5-[4-(difluoromethyl)phenyl]-4-ethyl-1,3-oxazol-2-yl}amino)-1,2,3,4-tetrahydronaphthalen-2-ol;
2-{[(7R)-7-hydroxy-5,6,7,8-tetrahydronaphthalen-1-yl]amino}-5-[4-(trifluoromethyl)phenyl]-1,3-oxazole-4-carbonitrile;
(2R)-8-{[5-(5-bromopyridin-2-yl)-4-methyl-1,3-oxazol-2-yl]amino}-1,2,3,4-tetrahydronaphthalen-2-ol;
(2R)-8-({5-[2,3-difluoro-4-(trifluoromethyl)phenyl]-4-methyl-1,3-oxazol-2-yl}amino)-1,2,3,4-tetrahydronaphthalen-2-ol;
(2R)-8-{[5-(4-bromophenyl)-4-ethyl-1,3-oxazol-2-yl]amino}-1,2,3,4-tetrahydronaphthalen-2-ol; and
(2S)-8-{[5-(4-bromophenyl)-4-ethyl-1,3-oxazol-2-yl]amino}-1,2,3,4-tetrahydronaphthalen-2-ol; or
a pharmaceutically acceptable salt thereof.

10. A pharmaceutical composition comprising a therapeutically effective amount of a compound of formula (I) according to claim 1, or a pharmaceutically acceptable salt thereof, and a pharmaceutically acceptable carrier.

11. The pharmaceutical composition according to claim 10 further comprising one or more analgesic agents selected from the group consisting of a nonsteroidal anti-inflammatory drug (NSAID) and acetaminophen, or a combination thereof.

12. The pharmaceutical composition of claim 11 wherein the nonsteroidal anti-inflammatory drug is ibuprofen.

13. A method for treating pain in a mammal in need of such treatment, comprising administering a therapeutically effective amount of a compound of formula (I) according to claim 1, or a pharmaceutically acceptable salt thereof.

14. The method according to claim 13 further comprising the step of co-administering with one or more analgesic agents selected from the group consisting of nonsteroidal anti-inflammatory drug (NSAID) and acetaminophen, or a combination thereof.

15. The method according to claim 14 wherein the nonsteroidal anti-inflammatory drug is ibuprofen.

* * * * *

UNITED STATES PATENT AND TRADEMARK OFFICE
CERTIFICATE OF CORRECTION

| | |
|---|---|
| PATENT NO. | : 7,998,993 B2 |
| APPLICATION NO. | : 12/256931 |
| DATED | : August 16, 2011 |
| INVENTOR(S) | : Richard J. Perner |

It is certified that error appears in the above-identified patent and that said Letters Patent is hereby corrected as shown below:

Column 79 part of Claim 9, Line 9 please revise – "azol-2-yl]amino}-1,2,3,4-" to read as --azol-2-yl}amino)-1,2,3,4- --

Column 79 Part of Claim 9, Line 15 please revise – "2-yl]amino}-1,2,3,4-" to read as --2-yl}amino)-1,2,3,4- --

Signed and Sealed this
First Day of May, 2012

David J. Kappos
*Director of the United States Patent and Trademark Office*